US011976289B2

(12) United States Patent
Lu et al.

(10) Patent No.: US 11,976,289 B2
(45) Date of Patent: May 7, 2024

(54) ABIOTIC STRESS TOLERANT PLANTS AND METHODS

(71) Applicants: PIONEER OVERSEAS CORPORATION, Johnston, IA (US); SINOBIOWAY BIO-AGRICULTURE GROUP CO. LTD., Beijing (CN)

(72) Inventors: Guihua Lu, San Diego, CA (US); Guokui Wang, Beijing (CN); Guanfan Mao, Beijing (CN); Yu Zhang, Beijing (CN); Changgui Wang, Beijing (CN); Guangwu Chen, Beijing (CN); Yang Gao, Beijing (CN)

(73) Assignees: PIONEER OVERSEAS CORPORATION; SINOBIOWAY BIO-AGRICULTURE GROUP CO. LTD.

( * ) Notice: Subject to any disclaimer, the term of this patent is extended or adjusted under 35 U.S.C. 154(b) by 100 days.

(21) Appl. No.: 17/595,447

(22) PCT Filed: May 22, 2019

(86) PCT No.: PCT/CN2019/087911

§ 371 (c)(1),
(2) Date: Nov. 17, 2021

(87) PCT Pub. No.: WO2020/232661

PCT Pub. Date: Nov. 26, 2020

(65) Prior Publication Data

US 2022/0186245 A1 Jun. 16, 2022

(51) Int. Cl.
*C12N 15/82* (2006.01)
*C07K 14/415* (2006.01)

(52) U.S. Cl.
CPC ........ *C12N 15/8273* (2013.01); *C07K 14/415* (2013.01)

(58) Field of Classification Search
None
See application file for complete search history.

(56) References Cited

U.S. PATENT DOCUMENTS

2004/0123343 A1* 6/2004 La Rosa .............. C07K 14/415 800/278
2016/0145631 A1 5/2016 Cellectis

FOREIGN PATENT DOCUMENTS

| | | | |
|---|---|---|---|
| CN | 101486757 | 7/2009 | |
| CN | 105483118 | 4/2016 | |
| WO | 2005021723 | 3/2005 | |
| WO | WO-2005021723 A2 * | 3/2005 | ........... C07K 14/415 |
| WO | 2010134654 | 11/2010 | |
| WO | 2019085961 | 5/2019 | |

OTHER PUBLICATIONS

Guo et al., 2004, Protein tolerance to random amino acid change, Proceedings of the National Academy of Sciences, 101:9205--9210 (Year: 2004) (Year: 2014) (Year: 2014).*
UniProt, Q10FW9_ORYSJ, 2006, https://www.uniprot.org/uniprotkb/Q10FW9/entry (Year: 2006).*
UniProt, I1R045_ORYGL, 2012, https://www.uniprot.org/uniprotkb/I1R045/entry (Year: 2012).*
NCBI GenBank. "Predicted:Oryza sativa Japonica group small ubiquitin-related modifier 1-like(LOC4324359), NCBI Reference Sequence Accession No. XM_015765444.2" NCBI GenBank, Aug. 7, 2018.
Rice Genome Annotation Project Funded by the NSF. "Rice Locus Identifier search" Feb. 6, 2013.
International Search Report and Written Opinion for PCT/CN2019/087911, dated Feb. 28, 2020.

* cited by examiner

*Primary Examiner* — Anne Kubelik
*Assistant Examiner* — Aleksandar Radosavljevic

(57) ABSTRACT

Isolated polynucleotides and polypeptides, and recombinant DNA constructs are useful for conferring improved drought tolerance and yield. Compositions (such as plants or seeds) comprise these recombinant DNA constructs; and methods utilize these recombinant DNA constructs. The recombinant DNA constructs comprise a polynucleotide operably linked to a promoter that is functional in a plant, wherein said polynucleotides encode drought tolerance polypeptides.

12 Claims, No Drawings

Specification includes a Sequence Listing.

ABIOTIC STRESS TOLERANT PLANTS AND METHODS

REFERENCE TO SEQUENCE LISTING SUBMITTED ELECTRONICALLY

The official copy of the sequence listing is submitted electronically via EFS-Web as an ASCII formatted sequence listing with a file named RTS22593O_SeqListing.txt created on Oct. 26, 2021 and having a size of 240 kilobytes and is filed concurrently with the specification. The sequence listing comprised in this ASCII formatted document is part of the specification and is herein incorporated by reference in its entirety.

FIELD

The field of the disclosure relates to plant breeding and genetics and, particularly, relates to improving tolerance to abiotic stress in plants.

BACKGROUND

Stresses to plants may be caused by both biotic and abiotic agents. For example, biotic causes of stress include infection with pathogen, insect feeding, and parasitism by another plant such as mistletoe. Abiotic stresses include, for example, excessive or insufficient available water, temperature extremes, and synthetic chemicals such as herbicides.

Abiotic stress is the primary cause of crop loss worldwide, causing average yield losses more than 50% for major crops (Boyer, J. S. (1982) *Science* 218:443-448; Bray, E. A. et al. (2000) In Biochemistry and Molecular Biology of Plants, edited by Buchannan, B. B. et al., Amer. Soc. Plant Biol., pp. 1158-1249).

Accordingly, there is a need to develop compositions and methods that increase tolerance to abiotic stress in plants. This invention provides such compositions and methods.

SUMMARY

The following embodiments are among those encompassed by the disclosure:

In one embodiment, the present disclosure includes an isolated polynucleotide, encoding a polypeptide with amino acid sequence of at least 90% sequence identity to SEQ ID NO: 3, 6, 9, 12, 15, 18, 21 or 24, wherein increased expression of the polynucleotide in a plant enhances drought tolerance. In certain embodiments, the isolated polynucleotide encodes the amino acid sequence of SEQ ID NO: 3, 6, 9, 12, 15, 18, 21 or 24. In certain embodiments, the isolated polynucleotide comprises the nucleotide sequence of SEQ ID NO: 1, 2, 4, 5, 7, 8, 10, 11, 13, 14, 16, 17, 19, 20, 22 or 23. In certain embodiments, increased expression of the polynucleotide in a plant enhances grain yield under drought conditions.

The present disclosure also provides a recombinant DNA construct comprising an isolated polynucleotide operably linked to at least one heterologous regulatory element, wherein the polynucleotide encodes a polypeptide with amino acid sequence of at least 90% sequence identity to SEQ ID NO: 3, 6, 9, 12, 15, 18, 21 or 24.

The present disclosure further provides a modified plant or seed having increased expression or activity of at least one polynucleotide encoding a polypeptide with amino acid sequence of at least 90% sequence identity to SEQ ID NO: 3, 6, 9, 12, 15, 18, 21 or 24. In certain embodiments, the modified plant or seed comprises in its genome a recombinant DNA construct comprising a polynucleotide operably linked to at least one heterologous regulatory element, wherein the polynucleotide encodes a polypeptide with amino acid sequence of at least 90% sequence identity to SEQ ID NO: 3, 6, 9, 12, 15, 18, 21 or 24. In certain embodiments, the modified plant exhibits improved drought tolerance and increased grain yield when grown under drought conditions compared to a control plant.

In certain embodiments, the modified plant or seed comprises a targeted genetic modification at a genomic locus comprising a polynucleotide encoding a polypeptide with amino acid sequence of at least 90% sequence identity to SEQ ID NO: 3, 6, 9, 12, 15, 18, 21 or 24, wherein the targeted genetic modification increase the expression and/or activity of the polypeptide. In certain embodiments, the modified plant exhibits improved drought tolerance and increased grain yield when grown under drought conditions compared to a control plant.

In certain embodiments, the plant is selected from the group consisting of rice, maize, soybean, sunflower, sorghum, canola, wheat, alfalfa, cotton, barley, millet, sugar cane and switchgrass.

Also provided are methods for increasing drought tolerance in a plant, the method comprising increasing the expression of at least one polynucleotide encoding a polypeptide with amino acid sequence of at least 90% sequence identity to SEQ ID NO: 3, 6, 9, 12, 15, 18, 21 or 24. Wherein the obtained plant exhibits increased drought tolerance when compared to the control plant.

In certain embodiments, the method for increasing drought tolerance comprises: (a) introducing into a regenerable plant cell a recombinant DNA construct comprising a polynucleotide operably linked to at least one heterologous regulatory element, wherein the polynucleotide encodes a polypeptide having an amino acid sequence of at least 80% sequence identity, when compared to SEQ ID NO: 3, 6, 9, 12, 15, 18, 21 or 24; and (b) generating the plant, wherein the plant comprises in its genome the recombinant DNA construct.

In certain embodiments, the method for increasing drought tolerance comprises: (a) introducing into a regenerable plant cell a targeted genetic modification at a genomic locus comprising a polynucleotide encoding a polypeptide having an amino acid sequence of at least 80% sequence identity, when compared to SEQ ID NO: 3, 6, 9, 12, 15, 18, 21 or 24; and (b) generating the plant, wherein the plant comprises in its genome the introduced genetic modification and has increased expression and/or activity of the polypeptide. In certain embodiments, the targeted genetic modification is introduced using a genome modification technique selected from the group consisting of a polynucleotide-guided endonuclease, CRISPR-Cas endonucleases, base editing deaminases, a zinc finger nuclease, a transcription activator-like effector nuclease (TALEN), an engineered site-specific meganucleases, or an Argonaute. In certain embodiments, the targeted genetic modification is present in (a) the coding region; (b) a non-coding region; (c) a regulatory sequence; (d) an untranslated region; or (e) any combination of (a)-(d) of the genomic locus that encodes a polypeptide comprising an amino acid sequence that is at 80% sequence identity, when compared to SEQ ID NO: 3, 6, 9, 12, 15, 18, 21 or 24.

BRIEF DESCRIPTION OF THE DRAWINGS AND SEQUENCE LISTING

The disclosure can be more fully understood from the following detailed description and the accompanying Sequence Listing which form a part of this application. The sequence descriptions and sequence listing attached hereto comply with the rules governing nucleotide and amino acid sequence disclosures in patent applications as set forth in 37 C.F.R. §§ 1.821 and 1.825. The sequence descriptions comprise the three letter codes for amino acids as defined in 37 C.F.R. §§ 1.821 and 1.825, which are incorporated herein by reference.

TABLE 1

Sequence Listing Description

| Source species | Clone Designation | SEQ ID NO: (Nucleotide) | SEQ ID NO: (Amino Acid) |
|---|---|---|---|
| *Oryza sativa* | OsDN-DTP8 | 1, 2 | 3 |
| *Oryza sativa* | OsKIK1 | 4, 5 | 6 |
| *Oryza sativa* | OsRWDD1 | 7, 8 | 9 |
| *Oryza sativa* | OsUFD1 | 10, 11 | 12 |
| *Oryza sativa* | OsPPR2 | 13, 14 | 15 |
| *Oryza sativa* | OsSAUR28-1 | 16, 17 | 18 |
| *Oryza sativa* | OsHYS1 | 19, 20 | 21 |
| *Oryza sativa* | OsFBID1 | 22, 23 | 24 |
| Artificial | Primers | 25-50 | n/a |
| *Oryza sativa* | DN-DTP8 paralog | 51 | 52 |
| *Oryza sativa* | KIK1 paralog | 53 | 54 |
| *Zea mays* | KIK1 homolog | 55 | 56 |
| *Sorghum bicolor* | KIK1 homolog | 57 | 58 |
| *Arabidopsis* | KIK1 homolog | 59 | 60 |
| *Glycine max* | KIK1 homolog | 61 | 62 |
| *Oryza sativa* | RWDD1 paralog | 63 | 64 |
| *Zea mays* | RWDD1 homolog | 65 | 66 |
| *Sorghum bicolor* | RWDD1 homolog | 67 | 68 |
| *Arabidopsis* | RWDD1 homolog | 69 | 70 |
| *Glycine max* | RWDD1 homolog | 71 | 72 |
| *Oryza sativa* | UFD1 paralog | 73 | 74 |
| *Zea mays* | UFD1 homolog | 75 | 76 |
| *Sorghum bicolor* | UFD1 homolog | 77 | 78 |
| *Arabidopsis* | UFD1 homolog | 79 | 80 |
| *Glycine max* | UFD1 homolog | 81 | 82 |
| *Oryza sativa* | PPR2 paralog | 83 | 84 |
| *Zea mays* | PPR2 homolog | 85 | 86 |
| *Sorghum bicolor* | PPR2 homolog | 87 | 88 |
| *Arabidopsis* | PPR2 homolog | 89 | 90 |
| *Glycine max* | PPR2 homolog | 91 | 92 |
| *Zea mays* | SAUR28-1 homolog | 93 | 94 |
| *Sorghum bicolor* | SAUR28-1 homolog | 95 | 96 |
| *Arabidopsis* | SAUR28-1 homolog | 97 | 98 |
| *Glycine max* | SAUR28-1 homolog | 99 | 100 |
| *Oryza sativa* | HYS1 paralog | 101 | 102 |
| *Zea mays* | HYS1 homolog | 103 | 104 |
| *Sorghum bicolor* | HYS1 homolog | 105 | 106 |
| *Arabidopsis* | HYS1 homolog | 107 | 108 |
| *Glycine max* | HYS1 homolog | 109 | 110 |
| *Oryza sativa* | FBID1 paralog | 111 | 112 |

DETAILED DESCRIPTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants; reference to "a cell" includes one or more cells and equivalents thereof known to those skilled in the art, and so forth.

Definitions

As used herein, "increased drought tolerance" of a plant refers to any measurable improvement in a physiological or physical characteristic, such as yield, as measured relative to a reference or control plant when grown under drought conditions. Typically, when a plant comprising a recombinant DNA construct or DNA modification in its genome exhibits increased drought tolerance relative to a reference or control plant, the reference or control plant does not comprise in its genome the recombinant DNA construct or DNA modification.

"Increased paraquat tolerance" of a plant is measured relative to a reference or control plant and reflects ability of the plant to survive with less physiological or physical deterioration than a reference or control plant after treated with paraquat solution. In general, tolerance to relative low level of paraquat can be used as a marker of abiotic stress tolerance, such as drought tolerance.

"Agronomic characteristic" is a measurable parameter including but not limited to: greenness, grain yield, growth rate, total biomass or rate of accumulation, fresh weight at maturation, dry weight at maturation, fruit yield, seed yield, total plant nitrogen content, fruit nitrogen content, seed nitrogen content, nitrogen content in a vegetative tissue, total plant free amino acid content, fruit free amino acid content, seed free amino acid content, free amino acid content in a vegetative tissue, total plant protein content, fruit protein content, seed protein content, protein content in a vegetative tissue, drought tolerance, nitrogen uptake, root lodging, harvest index, stalk lodging, plant height, ear height, ear length, salt tolerance, tiller number, panicle size, early seedling vigor and seedling emergence under low temperature stress.

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

A "control", "control plant" or "control plant cell" or the like provides a reference point for measuring changes in phenotype of a subject plant or plant cell in which genetic alteration, such as transformation, has been affected as to a gene of interest. For example, a control plant may be a plant having the same genetic background as the subject plant except for the genetic alteration that resulted in the subject plant or cell.

"Plant" includes reference to whole plants, plant organs, plant tissues, seeds and plant cells and progeny of the same. Plant cells include, without limitation, cells from seeds, suspension cultures, embryos, meristematic regions, callus tissues, leaves, roots, shoots, gametophytes, sporophytes, pollen, and microspores.

"Progeny" comprises any subsequent generation of a plant.

"Modified plant" includes reference to a plant which comprises within its genome a heterologous polynucleotide or modified gene or promoter. For example, the heterologous polynucleotide is stably integrated within the genome such that the polynucleotide is passed on to successive generations. The heterologous polynucleotide may be integrated into the genome alone or as part of a recombinant DNA construct.

"Heterologous" with respect to sequence means a sequence that originates from a foreign species, or, if from the same species, is substantially modified from its native form in composition and/or genomic locus by deliberate human intervention.

"Polynucleotide", "nucleic acid sequence", "nucleotide sequence", and "nucleic acid fragment" are used interchangeably and refer to a polymer of RNA or DNA that is single- or double-stranded, optionally containing synthetic, non-natural or altered nucleotide bases. Nucleotides (usually found in their 5'-monophosphate form) are referred to by their single-letter designation as follows: "A" for adenylate or deoxyadenylate, "C" for cytidylate or deoxycytidylate, and "G" for guanylate or deoxyguanylate for RNA or DNA, respectively; "U" for uridylate; "T" for deoxythymidylate; "R" for purines (A or G); "Y" for pyrimidines (C or T); "K" for G or T; "H" for A or C or T; "I" for inosine; and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, and sulfation, gamma-carboxylation of glutamic acid residues, hydroxylation and ADP-ribosylation.

"Recombinant DNA construct" refers to a combination of nucleic acid fragments that are not normally found together in nature. Accordingly, a recombinant DNA construct may comprise regulatory elements and coding sequences that are derived from different sources, or regulatory elements and coding sequences derived from the same source, but arranged in a manner different than that normally found in nature.

"Regulatory elements" refer to nucleotide sequences located upstream (5' non-coding sequences), within, or downstream (3' non-coding sequences) of a coding sequence, and influencing the transcription, RNA processing or stability, or translation of the associated coding sequence. Regulatory elements may include, but are not limited to, promoters, translation leader sequences, introns, and polyadenylation recognition sequences. The terms "regulatory sequence" and "regulatory element" and "regulatory region" are used interchangeably herein.

"Promoter" refers to a nucleic acid fragment capable of controlling transcription of another nucleic acid fragment. "Promoter functional in a plant" is a promoter capable of controlling transcription of genes in plant cells whether its origin is from a plant cell or not. "Tissue-specific promoter" and "tissue-preferred promoter" refers to a promoter that is expressed predominantly but not necessarily exclusively in one tissue or organ, but that may also be expressed in one specific cell or cell type. "Developmentally regulated promoter" is a promoter whose activity is determined by developmental events.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

As used herein "increased", "increase", or the like refers to any detectable increase in an experimental group (e.g., plant with a DNA modification described herein) as compared to a control group (e.g., wild-type plant that does not comprise the DNA modification). Accordingly, increased expression of a protein comprises any detectable increase in the total level of the protein in a sample and can be determined using routine methods in the art such as, for example, Western blotting and ELISA.

As used herein, "yield" refers to the amount of agricultural production harvested per unit of land, and may include reference to bushels per acre or kilograms per mu of a crop at harvest, as adjusted for grain moisture (e.g., typically 15% for maize, 13.5% for rice). Grain moisture is measured in the grain at harvest. The adjusted test weight of grain is determined to be the weight in pounds per bushel or grams per plant, adjusted for grain moisture level at harvest.

As used herein, "sequence identity" or "identity" in the context of two polynucleotides or polypeptide sequences refer to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, California).

As used herein, "percentage of sequence identity" is calculated by determining the number of positions at which the identical nucleic acid base or amino acid residue occurs in both sequences to yield the number of matched positions, dividing the number of matched positions by the total number of positions in the window of comparison, and multiplying the result by 100.

Unless stated otherwise, multiple alignments of the sequences provided herein are performed using the Clustal V method of alignment (Higgins and Sharp. (1989) *CABIOS.* 5:151-153) with the default parameters (GAP PENALTY=10, GAP LENGTH PENALTY=10). Default parameters for pairwise alignments and calculation of percent identity of amino acid sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Compositions:

A. Polynucleotides and Polypeptides

The present disclosure provides polynucleotides encoding the following polypeptides:

One aspect of the disclosure provides a polynucleotide encoding a polypeptide comprising an amino acid sequence that is at least 80% identical (e.g. 81%, 82%, 83%, 84%, 85%, 86%, 87%, 88%, 89%, 90%, 91%, 92%, 93%, 94%, 95%, 96%, 97%, 98%, 99%, or 100%) to the amino acid sequence of any one of SEQ ID NO: 3 (OsDN-DTP8), SEQ ID NO: 6 (OsKIK1), SEQ ID NO: 9 (OsRWDD1), SEQ ID NO: 12 (OsUFD1), SEQ ID NO: 15 (OsPPR2), SEQ ID NO: 18 (OsSAUR28-1), SEQ ID NO: 21 (OsHYS1) and SEQ ID NO: 24 (OsFBID1).

"OsDN-DTP8" refers to a rice polypeptide that confers drought tolerance phenotype when overexpressed. The OsDN-DTP8 polypeptide (SEQ ID NO: 3) is encoded by the coding sequence (CDS) (SEQ ID NO: 2) or nucleotide sequence (SEQ ID NO: 1) at rice gene locus LOC_Os09g04650.1, which is annotated as "Expressed protein" in TIGR. "DN-DTP8 polypeptide" refers herein to the OsDN-DTP8 polypeptide and its paralogs (e.g., SEQ ID NO: 52 encoded by SEQ ID NO: 51) or homologs from other organisms.

"OsKIK1" refers to a rice polypeptide that confers drought tolerance phenotype when overexpressed. The OsKIK1 polypeptide (SEQ ID NO: 6) is encoded by the coding sequence (CDS) (SEQ ID NO: 5) or nucleotide sequence (SEQ ID NO: 4) at rice gene locus LOC_Os07g36570.1, which is annotated as "KI domain interacting kinase 1, putative, expressed" in TIGR. "KIK1 polypeptide" refers herein to the OsKIK1 polypeptide and its paralogs (e.g., SEQ ID NO: 54 encoded by SEQ ID NO: 53) and homologs from other organisms, such as maize (SEQ ID NO: 56 encoded by SEQ ID NO: 55), sorghum (SEQ ID NO: 58 encoded by SEQ ID NO: 57), *Arabidopsis* (SEQ ID NO: 60 encoded by SEQ ID NO: 59), or soybean (SEQ ID NO: 62 encoded by SEQ ID NO: 61).

"OsRWDD1" refers to a rice polypeptide that confers drought tolerance phenotype when overexpressed. The OsRWDD1 polypeptide (SEQ ID NO: 9) is encoded by the coding sequence (CDS) (SEQ ID NO: 8) or nucleotide sequence (SEQ ID NO: 7) at rice gene locus LOC_Os02g46740.1, which is annotated as "RWD domain containing protein, expressed" in TIGR. "RWDD1 polypeptide" refers herein to the OsRWDD1 polypeptide and its paralogs (e.g., SEQ ID NO: 64 encoded by SEQ ID NO: 63) and homologs from other organisms, such as maize (SEQ ID NO: 66 encoded by SEQ ID NO: 65), sorghum (SEQ ID NO: 68 encoded by SEQ ID NO: 67), *Arabidopsis* (SEQ ID NO: 70 encoded by SEQ ID NO: 69), or soybean (SEQ ID NO: 72 encoded by SEQ ID NO: 71).

"OsUFD1" refers to a rice polypeptide that confers drought tolerance phenotype when overexpressed. The OsUFD1 polypeptide (SEQ ID NO: 12) is encoded by the coding sequence (CDS) (SEQ ID NO: 11) or nucleotide sequence (SEQ ID NO: 10) at rice gene locus LOC_Os01g68940.1, which is annotated as "Ubiquitin family domain containing protein, expressed" in TIGR. "UFD1 polypeptide" refers herein to the OsUFD1 polypeptide and its paralogs (e.g., SEQ ID NO: 74 encoded by SEQ ID NO: 73) and homologs from other organisms, such as maize (SEQ ID NO: 76 encoded by SEQ ID NO: 75), sorghum (SEQ ID NO: 78 encoded by SEQ ID NO: 77), *Arabidopsis* (SEQ ID NO: 80 encoded by SEQ ID NO: 79), or soybean (SEQ ID NO: 82 encoded by SEQ ID NO: 81).

"OsPPR2" refers to a rice polypeptide that confers drought tolerance phenotype when overexpressed. The OsPPR2 polypeptide (SEQ ID NO: 15) is encoded by the coding sequence (CDS) (SEQ ID NO: 14) or nucleotide sequence (SEQ ID NO: 13) at rice gene locus LOC_Os03g06910.1, which is annotated as "PPR repeat containing protein" in TIGR. "PPR2 polypeptide" refers herein to the OsPPR2 polypeptide and its paralogs (e.g., SEQ ID NO: 84 encoded by SEQ ID NO: 83) and homologs from other organisms, such as maize (SEQ ID NO: 86 encoded by SEQ ID NO: 85), sorghum (SEQ ID NO: 88 encoded by SEQ ID NO: 87), *Arabidopsis* (SEQ ID NO: 90 encoded by SEQ ID NO: 89), or soybean (SEQ ID NO: 92 encoded by SEQ ID NO: 91).

"OsSAUR28-1" refers to a rice polypeptide that confers drought tolerance phenotype when overexpressed. The OsSAUR28-1 polypeptide (SEQ ID NO: 18) is encoded by the coding sequence (CDS) (SEQ ID NO: 17) or nucleotide sequence (SEQ ID NO: 16) at rice gene locus LOC_Os06g48860.1, which is annotated as "OsSAUR28-Auxin-responsive SAUR gene family member, expressed" in TIGR. "SAUR28-1 polypeptide" refers herein to the OsSAUR28-1 polypeptide and its paralogs and homologs from other organisms, such as maize (SEQ ID NO: 94 encoded by SEQ ID NO: 93), sorghum (SEQ ID NO: 96 encoded by SEQ ID NO: 95), *Arabidopsis* (SEQ ID NO: 98 encoded by SEQ ID NO: 97), or soybean (SEQ ID NO: 100 encoded by SEQ ID NO: 99).

"OsHYS1" refers to a rice polypeptide that confers drought tolerance phenotype when overexpressed. The OsHYS1 polypeptide (SEQ ID NO: 21) is encoded by the coding sequence (CDS) (SEQ ID NO: 20) or nucleotide sequence (SEQ ID NO: 19) at rice gene locus LOC_Os01g68970.1, which is annotated as "HYS1, putative, expressed" in TIGR. "HYS1 polypeptide" refers herein to the OsHYS1 polypeptide and its paralogs (e.g., SEQ ID NO: 102 encoded by SEQ ID NO: 101) and homologs from other organisms, such as maize (SEQ ID NO: 104 encoded by SEQ ID NO: 103), sorghum (SEQ ID NO: 106 encoded by SEQ ID NO: 105), *Arabidopsis* (SEQ ID NO: 108 encoded by SEQ ID NO: 107), or soybean (SEQ ID NO: 110 encoded by SEQ ID NO: 109).

"OsFBID1" refers to a rice polypeptide that confers drought tolerance phenotype when overexpressed. The OsFBID1 polypeptide (SEQ ID NO: 24) is encoded by the coding sequence (CDS) (SEQ ID NO: 23) or nucleotide sequence (SEQ ID NO: 22) at rice gene locus LOC_Os04g31570.1, which is annotated as "F-box protein interaction domain containing protein, expressed" in TIGR. "FBID1 polypeptide" refers herein to the OsFBID1 polypeptide and its paralogs (e.g., SEQ ID NO: 112 encoded by SEQ ID NO: 111) and homologs from other organisms.

It is understood, as those skilled in the art will appreciate, that the disclosure encompasses more than the specific exemplary sequences. Alterations in a nucleic acid fragment which result in the production of a chemically equivalent amino acid at a given site, but do not affect the functional properties of the encoded polypeptide, are well known in the art. For example, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

B. Recombinant DNA constructs

Also provided are recombinant DNA constructs comprising any of the polynucleotides described herein. In certain embodiments, the recombinant DNA construct further comprises at least one regulatory element. In certain embodiments the at least one regulatory element is a heterologous regulatory element. In certain embodiments, the at least one regulatory element of the recombinant DNA construct comprises a promoter. In certain embodiments, the promoter is a heterologous promoter.

A number of promoters can be used in recombinant DNA constructs of the present disclosure. The promoters can be selected based on the desired outcome, and may include constitutive, tissue-specific, inducible, or other promoters for expression in the host organism.

A "constitutive" promoter is a promoter, which is active under most environmental conditions. Constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) Nature 313:810-812); rice actin (McElroy et al. (1990) Plant Cell 2:163-171); ubiquitin (Christensen et al. (1989) Plant Mol. Biol. 12:619-632 and Christensen et al. (1992) Plant Mol. Biol. 18:675-689); pEMU (Last et al. (1991) Theor. Appl. Genet. 81:581-588); MAS (Velten et al. (1984) EMBO J. 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

A tissue-specific or developmentally-regulated promoter is a DNA sequence which regulates the expression of a DNA sequence selectively in the cells/tissues of a plant, such as in those cells/tissues critical to tassel development, seed set, or both, and which usually limits the expression of such a DNA sequence to the developmental period of interest (e.g. tassel development or seed maturation) in the plant. Any identifiable promoter which causes the desired temporal and spatial expression may be used in the methods of the present disclosure.

Many leaf-preferred promoters are known in the art (Yamamoto et al. (1997) *Plant J.* 12(2):255-265; Kwon et al. (1994) *Plant Physiol.* 105:357-367; Yamamoto et al. (1994) *Plant Cell Physiol.* 35(5):773-778; Gotor et al. (1993) *Plant J.* 3:509-518; Orozco et al. (1993) *Plant Mol. Biol.* 23(6): 1129-1138; and Matsuoka et al. (1993) *Proc. Natl. Acad. Sci. USA* 90(20):9586-9590).

Promoters which are seed or embryo-specific and may be useful in the disclosure include soybean Kunitz trypsin inhibitor (Kti3, Jofuku and Goldberg. (1989) *Plant Cell* 1:1079-1093), convicilin, vicilin, and legumin (pea cotyledons) (Rerie, W. G., et al. (1991) *Mol. Gen. Genet.* 259: 149-157; Newbigin, E. J., et al. (1990) *Planta* 180:461-470; Higgins, T. J. V., et al. (1988) *Plant. Mol. Biol.* 11:683-695), zein (maize endosperm) (Schemthaner, J. P., et al. (1988) *EMBO J.* 7:1249-1255), phaseolin (bean cotyledon) (Segupta-Gopalan, C., et al. (1985) *Proc. Natl. Acad. Sci.* 82:3320-3324), phytohemagglutinin (bean cotyledon) (Voelker, T. et al. (1987) *EMBO J.* 6:3571-3577), B-conglycinin and glycinin (soybean cotyledon) (Chen, Z-L, et al. (1988) *EMBO J.* 7:297-302), glutelin (rice endosperm), hordein (barley endosperm) (Marris, C., et al. (1988) *Plant Mol. Biol.* 10:359-366), glutenin and gliadin (wheat endosperm) (Colot, V., et al. (1987) *EMBO J.* 6:3559-3564). Promoters of seed-specific genes operably linked to heterologous coding regions in chimeric gene constructions maintain their temporal and spatial expression pattern in transgenic plants. Such examples include *Arabidopsis* 2S seed storage protein gene promoter to express enkephalin peptides in *Arabidopsis* and *Brassica napus* seeds (Vanderkerckhove et al. (1989) *Bio/Technology* 7: L929-932), bean lectin and bean beta-phaseolin promoters to express luciferase (Riggs et al. (1989) *Plant Sci.* 63:47-57), and wheat glutenin promoters to express chloramphenicol acetyl transferase (Colot et al. (1987) *EMBO J* 6:3559-3564).

Inducible promoters selectively express an operably linked DNA sequence in response to the presence of an endogenous or exogenous stimulus, for example by chemical compounds (chemical inducers) or in response to environmental, hormonal, chemical, and/or developmental signals. Inducible or regulated promoters include, for example, promoters regulated by light, heat, stress, flooding or drought, phytohormones, wounding, or chemicals such as ethanol, jasmonate, salicylic acid, or safeners.

Also contemplated are synthetic promoters which include a combination of one or more heterologous regulatory elements.

The promoter of the recombinant DNA constructs of the invention can be any type or class of promoter known in the art, such that any one of a number of promoters can be used to express the various polynucleotide sequences disclosed herein, including the native promoter of the polynucleotide sequence of interest. The promoters for use in the recombinant DNA constructs of the invention can be selected based on the desired outcome.

The recombinant DNA constructs of the present disclosure may also include other regulatory elements, including but not limited to, translation leader sequences, introns, and polyadenylation recognition sequences. In certain embodiments, a recombinant DNA construct further comprises an enhancer or silencer.

An intron sequence can be added to the 5' untranslated region, the protein-coding region or the 3' untranslated region to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg. (1988) *Mol. Cell Biol.* 8:4395-4405; Callis et al. (1987) *Genes Dev.* 1:1183-1200).

C. Plants and Plant Cells

Provided are plants, plant cells, plant parts, seed and grain comprising in its genome any of the recombinant DNA constructs described herein, so that the plants, plant cells, plant parts, seed, and/or grain have increased expression of the encoded polypeptide.

Also provided are plants, plant cells, plant parts, seeds, and grain comprising an introduced genetic modification at a genomic locus that encodes a polypeptide comprising an amino acid sequence that is at least 80% identical to an amino acid sequence selected from the group consisting of SEQ ID NOs: 3, 6, 9, 12, 15, 18, 21 or 24. In certain embodiments, the genetic modification increases the activity of the encoded polypeptide. In certain embodiments, the genetic modification increases the level of the encoded polypeptide. In certain embodiments, the genetic modification increases both the level and activity of the encoded polypeptide.

The plant may be a monocotyledonous or dicotyledonous plant, for example, a rice or maize or soybean plant, such as a maize hybrid plant or a maize inbred plant. The plant may also be sunflower, sorghum, canola, wheat, alfalfa, cotton, barley, millet, sugar cane or switchgrass.

In certain embodiments the plant exhibits increased drought tolerance when compared to a control plant. In certain embodiments, the plant exhibits an alteration of at least one agronomic characteristic when compared to the control plant.

One of ordinary skill in the art is familiar with protocols for simulating drought conditions and for evaluating drought tolerance of plants that have been subjected to simulated or naturally-occurring drought conditions. For example, one can simulate drought conditions by giving plants less water than normally required or no water over a period of time, and one can evaluate drought tolerance by looking for differences in physiological and/or physical condition, including (but not limited to) vigor, growth, size, or root length, or in particular, leaf color or leaf area size. Other techniques for evaluating drought tolerance include measuring chlorophyll fluorescence, photosynthetic rates and gas exchange rates.

D. Stacking with Other Traits of Interest

In some embodiments, the inventive polynucleotides disclosed herein are engineered into a molecular stack. Thus, the various host cells, plants, plant cells, plant parts, seeds, and/or grain disclosed herein can further comprise one or more traits of interest. In certain embodiments, the host cell, plant, plant part, plant cell, seed, and/or grain is stacked with any combination of polynucleotide sequences of interest in order to create plants with a desired combination of traits. As used herein, the term "stacked" refers to having multiple traits present in the same plant or organism of interest. For example, "stacked traits" may comprise a molecular stack where the sequences are physically adjacent to each other. A trait, as used herein, refers to the phenotype derived from a particular sequence or groups of sequences. In one embodiment, the molecular stack comprises at least one polynucleotide that confers tolerance to glyphosate. Polynucleotides that confer glyphosate tolerance are known in the art.

In certain embodiments, the molecular stack comprises at least one polynucleotide that confers tolerance to glyphosate and at least one additional polynucleotide that confers tolerance to a second herbicide.

In certain embodiments, the plant, plant cell, seed, and/or grain having an inventive polynucleotide sequence may be stacked with, for example, one or more sequences that confer tolerance to: an ALS inhibitor; an HPPD inhibitor; 2,4-D; other phenoxy auxin herbicides; aryloxyphenoxypropionate herbicides; dicamba; glufosinate herbicides; herbicides which target the protox enzyme (also referred to as "protox inhibitors").

The plant, plant cell, plant part, seed, and/or grain having an inventive polynucleotide sequence can also be combined with at least one other trait to produce plants that further comprise a variety of desired trait combinations. For instance, the plant, plant cell, plant part, seed, and/or grain having an inventive polynucleotide sequence may be stacked with polynucleotides encoding polypeptides having pesticidal and/or insecticidal activity, or a plant, plant cell, plant part, seed, and/or grain having an inventive polynucleotide sequence may be combined with a plant disease resistance gene.

These stacked combinations can be created by any method including, but not limited to, breeding plants by any conventional methodology, or genetic transformation. If the sequences are stacked by genetically transforming the plants, the polynucleotide sequences of interest can be combined at any time and in any order. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference.

Methods:

Provided is a method for increasing drought tolerance and/or increasing grain yield, in a plant, comprising increasing the expression of at least one polynucleotide encoding a polypeptide with amino acid sequence of at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) sequence identity to SEQ ID NO: 3, 6, 9, 12, 15, 18, 21 or 24.

In certain embodiments, the method comprises: (a) expressing in a regenerable plant cell a recombinant DNA construct comprising a regulatory element operably linked to the polynucleotide encoding the polypeptide; and (b) generating the plant, wherein the plant comprises in its genome the recombinant DNA construct. In certain embodiments the regulatory element is a heterologous promoter.

In certain embodiments, the method comprises: (a) introducing in a regenerable plant cell a targeted genetic modification at a genomic locus that encodes the polypeptide; and (b) generating the plant, wherein the level and/or activity of the encoded polypeptide is increased in the plant. In certain embodiments the targeted genetic modification is introduced using a genome modification technique selected from the group consisting of a polynucleotide-guided endonuclease, CRISPR-Cas endonucleases, base editing deaminases, a zinc finger nuclease, a transcription activator-like effector nuclease (TALEN), engineered site-specific meganucleases, or Argonaute. In certain embodiments, the targeted genetic modification is present in (a) the coding region; (b) a non-coding region; (c) a regulatory sequence; (d) an untranslated region; or (e) any combination of (a)-(d) of the genomic locus that encodes a polypeptide comprising an amino acid sequence that is at least 80% identical to an amino acid sequence selected from the group consisting of SEQ ID NOs: 3, 6, 9, 12, 15, 18, 21 or 24.

In certain embodiments the DNA modification is an insertion of one or more nucleotides, preferably contiguous, in the genomic locus. For example, the insertion of an expression modulating element (EME), such as an EME described in PCT/US2018/025446, in operable linkage with the gene. In certain embodiments, the targeted DNA modification may be the replacement of the endogenous polypeptide promoter with another promoter known in the art to have higher expression. In certain embodiments, the targeted DNA modification may be the insertion of a promoter known in the art to have higher expression into the 5'UTR so that expression of the endogenous polypeptide is controlled by the inserted promoter. In certain embodiments, the DNA modification is a modification to optimize Kozak context to increase expression. In certain embodiments, the DNA modification is a polynucleotide modification or SNP at a site that regulates the stability of the expressed protein.

The plant for use in the inventive methods can be any plant species described herein. In certain embodiments, the plant is maize, soybean, or rice.

Various methods can be used to introduce a sequence of interest into a plant, plant part, plant cell, seed, and/or grain. "Introducing" is intended to mean presenting to the plant, plant cell, seed, and/or grain the inventive polynucleotide or resulting polypeptide in such a manner that the sequence gains access to the interior of a cell of the plant. The methods of the disclosure do not depend on a particular method for introducing a sequence into a plant, plant cell, seed, and/or grain, only that the polynucleotide or polypeptide gains access to the interior of at least one cell of the plant.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. Nos. 5,563,055 and 5,981,840), direct gene transfer (Paszkowski et al. (1984) *EMBO J.* 3:2717-2722), and ballistic particle acceleration (see, for example, U.S. Pat. Nos. 4,945,050; 5,879,918; 5,886,244; and, 5,932,782; Tomes et al. (1995) in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783; and, 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature (London)* 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, New York), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

In other embodiments, the inventive polynucleotides disclosed herein may be introduced into plants by contacting plants with a virus or viral nucleic acids. Generally, such methods involve incorporating a nucleotide construct of the disclosure within a DNA or RNA molecule. It is recognized that the inventive polynucleotide sequence may be initially synthesized as part of a viral polyprotein, which later may be processed by proteolysis in vivo or in vitro to produce the desired recombinant protein. Further, it is recognized that promoters disclosed herein also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221; herein incorporated by reference.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present disclosure provides transformed seed (also referred to as "transgenic seed") having a polynucleotide disclosed herein, for example, as part of an expression cassette, stably incorporated into their genome.

Transformed plant cells which are derived by plant transformation techniques, including those discussed above, can be cultured to regenerate a whole plant which possesses the transformed genotype (i.e., an inventive polynucleotide), and thus the desired phenotype, such as increased yield. For transformation and regeneration of maize see, Gordon-Kamm et al., *The Plant Cell,* 2:603-618 (1990).

Various methods can be used to introduce a genetic modification at a genomic locus that encodes a polypeptide disclosed herein into the plant, plant part, plant cell, seed, and/or grain. In certain embodiments the targeted DNA modification is through a genome modification technique selected from the group consisting of a polynucleotide-guided endonuclease, CRISPR-Cas endonucleases, base editing deaminases, zinc finger nuclease, a transcription activator-like effector nuclease (TALEN), engineered site-specific meganuclease, or Argonaute.

In some embodiments, the genome modification may be facilitated through the induction of a double-stranded break (DSB) or single-strand break, in a defined position in the genome near the desired alteration. DSBs can be induced using any DSB-inducing agent available, including, but not limited to, TALENs, meganucleases, zinc finger nucleases, Cas9-gRNA systems (based on bacterial CRISPR-Cas systems), guided cpf1 endonuclease systems, and the like. In some embodiments, the introduction of a DSB can be combined with the introduction of a polynucleotide modification template.

A polynucleotide modification template can be introduced into a cell by any method known in the art, such as, but not limited to, transient introduction methods, transfection, electroporation, microinjection, particle mediated delivery, topical application, whiskers mediated delivery, delivery via cell-penetrating peptides, or mesoporous silica nanoparticle (MSN)-mediated direct delivery.

The polynucleotide modification template can be introduced into a cell as a single stranded polynucleotide molecule, a double stranded polynucleotide molecule, or as part of a circular DNA (vector DNA). The polynucleotide modification template can also be tethered to the guide RNA and/or the Cas endonuclease.

A "modified nucleotide" or "edited nucleotide" refers to a nucleotide sequence of interest that comprises at least one alteration when compared to its non-modified nucleotide sequence. Such "alterations" include, for example: (i) replacement of at least one nucleotide, (ii) a deletion of at least one nucleotide, (iii) an insertion of at least one nucleotide, or (iv) any combination of (i)-(iii).

The term "polynucleotide modification template" includes a polynucleotide that comprises at least one nucleotide modification when compared to the nucleotide sequence to be edited. A nucleotide modification can be at least one nucleotide substitution, addition or deletion. Optionally, the polynucleotide modification template can further comprise homologous nucleotide sequences flanking the at least one nucleotide modification, wherein the flanking homologous nucleotide sequences provide sufficient homology to the desired nucleotide sequence to be edited.

The process for editing a genomic sequence combining DSB and modification templates generally comprises: providing to a host cell, a DSB-inducing agent, or a nucleic acid encoding a DSB-inducing agent, that recognizes a target sequence in the chromosomal sequence and is able to induce a DSB in the genomic sequence, and at least one polynucleotide modification template comprising at least one nucleotide alteration when compared to the nucleotide sequence to be edited. The polynucleotide modification template can further comprise nucleotide sequences flanking the at least one nucleotide alteration, in which the flanking sequences are substantially homologous to the chromosomal region flanking the DSB.

The endonuclease can be provided to a cell by any method known in the art, for example, but not limited to, transient introduction methods, transfection, microinjection, and/or topical application or indirectly via recombination constructs. The endonuclease can be provided as a protein or as a guided polynucleotide complex directly to a cell or indirectly via recombination constructs. The endonuclease can be introduced into a cell transiently or can be incorporated into the genome of the host cell using any method known in the art. In the case of a CRISPR-Cas system, uptake of the endonuclease and/or the guided polynucleotide into the cell can be facilitated with a Cell Penetrating Peptide (CPP) as described in WO2016073433 published May 12, 2016.

In addition to modification by a double strand break technology, modification of one or more bases without such double strand break are achieved using base editing technology, see e.g., Gaudelli et al., (2017) Programmable base editing of A*T to G*C in genomic DNA without DNA cleavage. Nature 551(7681):464-471; Komor et al., (2016) Programmable editing of a target base in genomic DNA without double-stranded DNA cleavage, Nature 533(7603): 420-4.

These fusions contain dCas9 or Cas9 nickase and a suitable deaminase, and they can convert e.g., cytosine to uracil without inducing double-strand break of the target DNA. Uracil is then converted to thymine through DNA replication or repair. Improved base editors that have targeting flexibility and specificity are used to edit endogenous locus to create target variations and improve grain yield. Similarly, adenine base editors enable adenine to inosine change, which is then converted to guanine through repair or replication. Thus, targeted base changes i.e., C·G to T·A conversion and A·T to G·C conversion at one more location made using appropriate site-specific base editors.

In an embodiment, base editing is a genome editing method that enables direct conversion of one base pair to another at a target genomic locus without requiring double-stranded DNA breaks (DSBs), homology-directed repair (HDR) processes, or external donor DNA templates. In an embodiment, base editors include (i) a catalytically impaired CRISPR-Cas9 mutant that are mutated such that one of their nuclease domains cannot make DSBs; (ii) a single-strand-specific cytidine/adenine deaminase that converts C to U or A to G within an appropriate nucleotide window in the single-stranded DNA bubble created by Cas9; (iii) a uracil glycosylase inhibitor (UGI) that impedes uracil excision and downstream processes that decrease base editing efficiency and product purity; and (iv) nickase activity to cleave the non-edited DNA strand, followed by cellular DNA repair processes to replace the G-containing DNA strand.

As used herein, a "genomic region" is a segment of a chromosome in the genome of a cell that is present on either side of the target site or, alternatively, also comprises a portion of the target site. The genomic region can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800. 5-2900, 5-3000, 5-3100 or more bases such that the genomic region has sufficient homology to undergo homologous recombination with the corresponding region of homology.

TAL effector nucleases (TALEN) are a class of sequence-specific nucleases that can be used to make double-strand breaks at specific target sequences in the genome of a plant or other organism (Miller et al. (2011) Nature Biotechnology 29:143-148).

Endonucleases are enzymes that cleave the phosphodiester bond within a polynucleotide chain. Endonucleases include restriction endonucleases, which cleave DNA at specific sites without damaging the bases, and meganucleases, also known as homing endonucleases (HEases), which like restriction endonucleases, bind and cut at a specific recognition site, however the recognition sites for meganucleases are typically longer, about 18 bp or more (patent application PCT/US12/30061, filed on Mar. 22, 2012). Meganucleases have been classified into four families based on conserved sequence motifs, the families are the LAGLIDADG, GIY-YIG, H-N-H, and His-Cys box families. These motifs participate in the coordination of metal ions and hydrolysis of phosphodiester bonds. HEases are notable for their long recognition sites, and for tolerating some sequence polymorphisms in their DNA substrates. The naming convention for meganuclease is similar to the convention for other restriction endonuclease. Meganucleases are also characterized by prefix F-, I-, or PI- for enzymes encoded by free-standing ORFs, introns, and inteins, respectively. One step in the recombination process involves polynucleotide cleavage at or near the recognition site. The cleaving activity can be used to produce a double-strand break. For reviews of site-specific recombinases and their recognition sites, see, Sauer (1994) Curr Op Biotechnol 5:521-7; and Sadowski (1993) FASEB 7:760-7. In some examples the recombinase is from the Integrase or Resolvase families.

Zinc finger nucleases (ZFNs) are engineered double-strand break inducing agents comprised of a zinc finger DNA binding domain and a double-strand-break-inducing agent domain. Recognition site specificity is conferred by the zinc finger domain, which typically comprising two, three, or four zinc fingers, for example having a C2H2 structure, however other zinc finger structures are known and have been engineered. Zinc finger domains are amenable for designing polypeptides which specifically bind a selected polynucleotide recognition sequence. ZFNs include an engineered DNA-binding zinc finger domain linked to a non-specific endonuclease domain, for example nuclease domain from a Type IIs endonuclease such as FokI. Additional functionalities can be fused to the zinc-finger binding domain, including transcriptional activator domains, transcription repressor domains, and methylases. In some examples, dimerization of nuclease domain is required for cleavage activity. Each zinc finger recognizes three consecutive base pairs in the target DNA. For example, a 3-finger domain recognized a sequence of 9 contiguous nucleotides, with a dimerization requirement of the nuclease, two sets of zinc finger triplets are used to bind an 18 nucleotide recognition sequence.

Genome editing using DSB-inducing agents, such as Cas9-gRNA complexes, has been described, for example in U.S. Patent Application US 2015-0082478 A1, published on Mar. 19, 2015, WO2015/026886 A1, published on Feb. 26, 2015, WO2016007347, published on Jan. 14, 2016, and WO201625131, published on Feb. 18, 2016, all of which are incorporated by reference herein.

EXAMPLES

The following are examples of specific embodiments of some aspects of the invention. The examples are offered for illustrative purposes only and are not intended to limit the scope of the invention in any way.

Example 1

Cloning and Vector Construction of Drought Tolerance Genes

A binary construct that contains four multimerized enhancers elements derived from the Cauliflower Mosaic Virus 35S (CaMV 35S) promoter was used, and the rice activation tagging population was developed from four japonica (*Oryza sativa* ssp. *Japonica*) varieties (Zhonghua 11, Chaoyou 1, Taizhong 65 and Nipponbare), which were transformed by *Agrobacteria*-mediated transformation method as described by Lin and Zhang ((2005) *Plant Cell Rep.* 23:540-547). The transgenic lines generated were developed and the transgenic seeds were harvested to form the rice activation tagging population.

Drought tolerance tagging lines (ATLs) were confirmed in repeated field experiments and their T-DNA insertion loci were determined. The genes near by the left border and right border of the T-DNA were cloned and the functional genes were recapitulated by field screens. Only the recapitulated functional genes are showed herein. And based on LOC IDs of these genes shown in Table 2, primers were designed for cloning the rice drought tolerance genes OsDN-DTP8, OsKIK1, OsRWDD1, OsUFD1, OsPPR2, OsSAUR28-1, OsHYS1, OsFBID1.

TABLE 2

| Rice gene names, Gene IDs (from TIGR) and Construct IDs | | |
|---|---|---|
| Gene name | LOC ID | Construct ID |
| OsDN-DTP8 | LOC_Os09g04650.1 | DP1130 |
| OsKIK1 | LOC_Os07g36570.1 | DP0808 |
| OsRWDD1 | LOC_Os02g46740.1 | DP0828 |
| OsUFD1 | LOC_Os01g68940.1 | DP0903 |
| OsPPR2 | LOC_Os03g06910.1 | DP0839 |
| OsSAUR28-1 | LOC_Os06g48860.1 | DP1122 |
| OsHYS1 | LOC_Os01g68970.1 | DP0984 |
| OsFBID1 | LOC_Os04g31570.1 | DP0893 |

PCR amplified products were extracted after the agarose gel electrophoresis using a column kit and then ligated with TA cloning vectors. The sequences and orientation in these constructs were confirmed by sequencing. Each gene was cloned into a plant binary construct.

Example 2

Transformation and Gene Expression Analysis of Transgenic Rice Lines

Zhonghua 11 (*Oryza sativa* L.) were transformed with either a vector prepared in Example 1 or an empty vector (DP0158) by *Agrobacteria*-mediated transformation as described by Lin and Zhang ((2005) *Plant Cell Rep.* 23:540-547). Transgenic seedlings ($T_0$) generated in the transformation laboratory were transplanted in field to get $T_1$ seeds. The $T_1$ and subsequent $T_2$ seeds were screened to confirm transformation and positively identified transgenic seeds were used in the following trait screens.

The gene expression levels in the leaves of the transgenic rice plants were determined by RT-PCR. Primers were designed for the RT-PCR for OsDN-DTP8, OsRWDD1, OsUFD1, OsSAUR28-1 and OsHYS1 genes in the over-expression transgenic rice. The level of expression in ZH11-TC (tissue cultured ZH11 rice) was set at 1.00, and the expression levels in the DP1130, DP0828, DP0903 and DP1121-transgenic rice plants were compared to ZH11-TC. The level of expression in DP0158 was set at 1.00, and the expression levels in the DP0984-transgenic rice plants were compared to DP0158. Gene expression was normalized based on the EF-1α mRNA levels, and the results from the gene expression analysis are provided in Table 3 below.

TABLE 3

| Relative Expression Level Fold Increase in Transgenic Rice Plants | | |
|---|---|---|
| Gene name | Construct ID | Relative Expression Level Fold Increase |
| OsDN-DTP8 | DP1130 | From 181.97 to 439.88 |
| OsRWDD1 | DP0828 | From 1.51 to 593.71 |
| OsUFD1 | DP0903 | From 10.62 to 414.52 |
| OsSAUR28-1 | DP1122 | From 8.64 to 98.90 |
| OsHYS1 | DP0984 | From 0.80 to 57.45 |

Example 3

Characterization of the Transgenic Rice Plants

The transgenic rice plants from Example 2 and ZH11-TC and DP0158 rice plants were tested for: (a) drought tolerance, (b) paraquat tolerance.

$T_2$ seeds from the plants of Example 2 were sterilized by 800 ppm carbendazol for 8 hours at 32° C. and washed 3-5 time, soaked in water for 16 hours at 32° C., and germinated for 18 hours at 35-37° C. in an incubator. Germinated seeds were used as follows for each test:

(a) drought tolerance—germinated seeds were planted in a seedbed field. At 3-leaf stage, the seedlings were transplanted into the testing field with 4 replicates and 10 plants per replicate for each transgenic line, and the 4 replicates were planted in the same block. ZH11-TC and DP0158 seedlings were nearby the transgenic lines in the same block, and were used as controls in the statistical analysis. The rice plants were managed by normal practice using pesticides and fertilizers. Watering was stopped at the panicle initiation stage, so as to give drought stress at flowering stage depending on the weather conditions (temperature and humidity). The soil water content was measured every 4 days at about 10 sites per block using TDR30 (Spectrum Technologies, Inc.). Plant phenotypes were observed and recorded during the experiments. The phenotypes include heading date, leaf rolling degree, drought sensitivity and drought tolerance. Special attention was paid to leaf rolling degree at noontime. At the end of the growing season, six representative plants of each transgenic line were harvested from the middle of the row per line, and grain yield per plant was measured. The grain yield data were statistically analyzed using mixed linear model.

(b) paraquat tolerance—germinated seeds were placed in a tube with a hole at the bottom, and water cultured at 30° C. for 5 days till one-leaf and one-terminal bud stage. Uniform seedlings about 3.5-4 cm in height were selected for paraquat testing. Randomized block design was used in this experiment. There were five blocks, each of which has 16×12 holes. Each transgenic line was placed in one row (12 plants/line), and ZH11-TC and DP0158 seedlings were placed in 3 rows (3×12 plants) randomly in one block. Then the seedlings were treated with 0.8 μM paraquat solution for 7 days at 10 h day/14 h night, and the treated seedlings first encountered dark and took up the paraquat solution which was changed every two days. After treated for 7 days, the green seedlings were counted. Those seedlings that maintain green in whole without damage were considered as paraquat tolerant seedling; those with bleached leaves or stem were not considered as paraquat tolerant seedling.

Tolerance rate was used as a parameter for this trait screen, which is the percentage of plants which kept green and showed tolerant phenotype over the total plant number. The data was analyzed using a statistic model of "Y~seg+line (seg)+rep+error", random effect of "rep", Statistic Method of "SAS® PROC GLIMMIX".

The results from these studies are provided in Table 4, which provides the combined data of the transgenic lines for each of the constructs.

TABLE 4

Agronomic Characteristics of the Transgenic Rice Plants

| No | Construct ID | Avg. yield per plant under field drought conditions (g/plant) | Paraquat Tolerance rate (%) |
|---|---|---|---|
| 1 | ZH11-TC | 4.59 ± 0.66 | |
| | DP0158 | 3.98 ± 0.66 | |
| | DP1130 | 6.11 ± 0.55 [a, b] | |
| 2 | ZH11-TC | 4.29 ± 0.94 | |
| | DP0158 | 3.49 ± 0.94 | |
| | DP0808 | 7.43 ± 1.00 [a, b] | |
| 3 | ZH11-TC | 3.01 ± 1.14 | 63% |
| | DP0158 | 2.74 ± 1.14 | 66% |
| | DP0828 | 4.59 ± 0.96 [a, b] | 80% [m, n] |
| 4 | ZH11-TC | 5.50 ± 1.42 | |
| | DP0158 | 4.44 ± 1.42 | |
| | DP0903 | 7.17 ± 1.33 [a, b] | |
| 5 | ZH11-TC | 1.57 ± 0.59 | 64% |
| | DP0158 | 2.02 ± 0.59 | 63% |
| | DP0839 | 2.94 ± 0.52 [a, b] | 82% [m, n] |
| 6 | ZH11-TC | 4.44 ± 0.89 | 31% |
| | DP0158 | 3.90 ± 0.87 | 39% |
| | DP1122 | 5.90 ± 0.86 [a, b] | 44% [m] |
| 7 | ZH11-TC | 4.97 ± 1.91 | |
| | DP0158 | 4.49 ± 1.91 | |
| | DP0984 | 7.16 ± 1.81 [a, b] | |
| 8 | ZH11-TC | 6.13 ± 0.95 | |
| | DP0158 | 5.15 ± 1.09 | |
| | DP0893 | 9.52 ± 1.06 [a, b] | |

[a] P ≤ 0.1 compared to ZH11-TC control in field;
[b] P ≤ 0.1 compared to DP0158 control in field.
[m] P ≤ 0.1 compared to ZH11-TC control in Lab;
[n] P ≤ 0.1 compared to DP0158 control in Lab.

DP1130-transgenic rice plants were tested three times in Hainan field in three years. All of them showed that the average yield per plant of DP1130-transgenic rice increased under field drought conditions compared to the controls. As shown in Table 4, twelve lines were tested, and three lines observed good seed setting rate in Hainan field. The yield of 8 lines showed significantly increased (P<0.1) than that of DP0158 control, and the yield of 6 lines showed significantly increased than that of ZH11-TC control. The average yield per plant of these 12 lines is 33% and 54% higher than that of ZH11-TC and DP0158 controls, respectively. These data show that OsDN-DTP8 is a rice drought tolerance gene.

DP0808-transgenic rice plants were tested two times in Hainan in two years. All of them showed that the average yield per plant of DP0808-transgenic rice increased under field drought conditions compared to the controls. As shown in Table 4, six lines were tested in Hainan field. The yield of 4 lines showed significantly increased yield (P<0.1) than that of DP0158 and ZH11-TC controls. The average yield per plant of these 6 lines is 73% and 113% higher than that of ZH11-TC and DP0158 controls, respectively. These data show that OsKIK1 is a rice drought tolerance gene.

DP0828-transgenic rice plants were tested three times in Ningxia and Hainan in three years. All of them showed that the average yield per plant of DP0828-transgenic rice increased under field drought conditions compared to the controls. As shown in Table 4, twelve lines were tested in Hainan field. The yield of 8 lines showed significantly increased (P<0.1) than that of DP0158 control, and the yield of 5 lines showed significantly increased than that of ZH11-TC control. The average yield per plant of these 12 lines is 52% and 68% higher than that of ZH11-TC and DP0158 controls, respectively. The DP0828-transgenic rice plants were also tested two times in paraquat assays. Consistent results were obtained. In the second experiment, the average paraquat tolerance rate of all DP0828-transgenic lines (80%) was significantly greater than that of ZH11-TC (63%) and DP0158 (66%) controls at the construct level. At the transgenic line level, seven OsRWDD1 transgenic lines had significantly greater tolerance rates than that of ZH11-TC control and six lines had significantly greater tolerance rates than DP0158 control (Table 4). These results demonstrate that OsRWDD1 transgenic rice plants had enhanced drought tolerance and paraquat tolerance compared to both controls. OsRWDD1 functions in enhancing drought tolerance and paraquat tolerance or antioxidative ability of transgenic plants.

DP0903-transgenic rice plants were tested three times in Ningxia and Hainan in two years. Two of them showed that the average yield per plant of DP0903-transgenic rice increased under field drought conditions compared to the controls. As shown in Table 4, eight lines were tested in Hainan field. The yield of 8 lines showed significantly increased (P<0.1) than that of DP0158 control, and the yield of 4 lines showed significantly increased than that of ZH11-TC control. The average yield per plant of these 8 lines is 30% and 61 higher than that of ZH11-TC and DP0158 controls, respectively. These results demonstrate that OsUFD1 transgenic rice plants had enhanced drought tolerance.

DP0839-transgenic rice plants were tested three times in Ningxia and Hainan in three years. Two of them showed that the average yield per plant of DP0839-transgenic rice increased under field drought conditions compared to the controls. As shown in Table 4, twelve lines were tested in Hainan field. The yield of 6 lines showed significantly increased (P<0.1) than that of DP0158 control, and the yield of 7 lines showed significantly increased than that of ZH11-TC control. The average yield per plant of these 12 lines is 87% and 46% higher than that of ZH11-TC and DP0158 controls, respectively. The DP0839-transgenic rice plants were also tested two times in paraquat assays. Consistent results were obtained. In the first experiment, the average paraquat tolerance rate of all DP0839-transgenic lines (82%) was significantly greater than that of ZH11-TC (64%) and DP0158 (63%) controls at the construct level. At the transgenic line level, six OsPPR2 transgenic lines had significantly greater tolerance rates than that of ZH11-TC and DP0158 controls (Table 4). These results demonstrate that OsPPR2 transgenic rice plants had enhanced drought tolerance and paraquat tolerance compared to both controls. OsPPR2 functions in enhancing drought tolerance and paraquat tolerance or antioxidative ability of transgenic plants.

DP1122-transgenic rice plants were tested three times in Ningxia and Hainan in two years. All of them showed that the average yield per plant of DP1122-transgenic rice increased under field drought conditions compared to the controls. As shown in Table 4, seven lines were tested in Hainan field. The yield of 4 lines showed significantly increased (P<0.1) than that of DP0158 and ZH11-TC controls, and were observed good seed setting rate in field. The average yield per plant of these 7 lines is 33% and 51% A higher than that of ZH11-TC and DP0158 controls, respectively. The DP1122-transgenic rice plants were also tested two times in paraquat assays. Consistently results were obtained. In the first experiment, the average paraquat tolerance rate of nine DP1121-transgenic lines (44%) was significantly greater than that of ZH11-TC (31%) and greater than that of DP0158 (39%) at construct level. At transgenic line level, three of nine OsSAUR28-1 transgenic lines had significantly greater tolerance rates than that of ZH11-TC and DP0158 controls (Table 4). These results demonstrate that OsSAUR28-1 transgenic rice plants had enhanced drought tolerance and paraquat tolerance compared to both controls. OsSAUR28-1 functions in enhancing drought tolerance and paraquat tolerance or antioxidative ability of transgenic plants.

DP0984-transgenic rice plants were tested three times in Ningxia and Hainan in three years. Two of them showed that the average yield per plant of DP0984-transgenic rice increased under field drought conditions compared to the controls. As shown in Table 4, twelve lines were tested, and five of them were observed good seed setting rate in Hainan field. The yield of 10 lines showed significantly increased (P<0.1) than that of DP0158 and 9 lines showed significantly increased than that of ZH11-TC. The average yield per plant of these 12 lines is 44% and 59% higher than that of ZH11-TC and DP0158 controls, respectively. These results demonstrate that OsHYS1 transgenic rice plants had enhanced drought tolerance.

DP0893-transgenic rice plants were tested three times in Ningxia and Hainan in three years. Two of them showed that the average yield per plant of DP0893-transgenic rice increased under field drought conditions compared to the controls. As shown in Table 4, six lines were tested in Hainan field. The yield of 6 lines showed significantly increased (P<0.1) than that of DP0158 and 5 lines showed significantly increased than that of ZH11-TC. The average yield per plant of these 6 lines is 55% and 85% higher than that of ZH11-TC and DP0158 controls, respectively. These results demonstrate that OsFBID1 transgenic rice plants had enhanced drought tolerance.

Taken together, these results indicate that OsDN-DTP8, OsKIK1, OsRWDD1, OsUFD1, OsPPR2, OsSAUR28-1, OsHYS1 and OsFBID1 transgenic rice plants have increased tolerance to drought conditions compared to control plants.

Example 4

Transformation and Evaluation of Maize with Rice Drought Tolerance Genes

Maize plants will be transformed with one of the polynucleotides encoding the polypeptides described herein or a corresponding homolog from maize, *Arabidopsis*, or other species. Expression of the gene in the maize transformation vector can be under control of a constitutive promoter such as the maize ubiquitin promoter (Christensen et al. (1989) *Plant Mol. Biol.* 12:619-632 and Christensen et al. (1992) *Plant Mol. Biol.* 18:675-689) or under control of another promoter, such as a stress-responsive promoter or a tissue-preferred promoter. The recombinant DNA construct can be introduced into maize cells by particle bombardment substantially as described in International Patent Publication WO 2009/006276. Alternatively, maize plants can be transformed with the recombinant DNA construct by *Agrobacterium*-mediated transformation substantially as described by Zhao et al. in *Meth. Mol. Biol.* 318:315-323 (2006) and in Zhao et al., *Mol. Breed.* 8:323-333 (2001) and U.S. Pat. No. 5,981,840 issued Nov. 9, 1999.

Progeny of the regenerated plants, such as $T_1$ plants, can be subjected to a soil-based drought stress. Using image analysis, plant area, volume, growth rate and color can be measured at multiple times before and during drought stress. Significant delay in wilting or leaf area reduction, a reduced yellow-color accumulation, and/or an increased growth rate during drought stress, relative to a control, will be considered evidence that the gene functions in maize to enhance drought tolerance.

Example 5

Laboratory Drought Screening of Rice Drought Tolerance Genes in *Arabidopsis*

To understand whether rice drought tolerance genes can improve dicot plants' drought tolerance, or other traits, the rice expression vectors described herein can be transformed into *Arabidopsis* (Columbia) using floral dip method by *Agrobacterium* mediated transformation procedure and transgenic plants were identified (Clough, S. T. and Bent, A. F. (1998) *The Plant Journal* 16, 735-743; Zhang, X. et al. (2006) *Nature Protocols* 1: 641-646).

Progeny of the regenerated plants, such as $T_1$ plants, can be subjected to a soil-based drought stress. Using image analysis, plant area, volume, growth rate and color can be measured at multiple times before and during drought stress. Significant delay in wilting or leaf area reduction, a reduced yellow-color accumulation, and/or an increased growth rate during drought stress, relative to a control, will be considered evidence that the gene functions in dicot plants to enhance drought tolerance.

What is claimed is:

1. A modified plant or seed comprising a polynucleotide encoding a polypeptide comprising an amino acid sequence that is at least 97% identical to SEQ ID NO: 3 operably linked to at least one heterologous regulatory element wherein the modified plant or seed comprises an increased expression of the polypeptide and improved drought tolerance as compared to a control plant.

2. The plant of claim 1, wherein the plant comprises in its genome a recombinant DNA construct comprising the polynucleotide operably linked to the at least one heterologous regulatory element.

3. The plant of claim 1, wherein the plant comprises a targeted genetic modification at a genomic locus comprising a polynucleotide sequence encoding a polypeptide with an amino acid sequence of at least 97% sequence identity to SEQ ID NO: 3, thereby increasing expression of the polypeptide as compared to a control plant not comprising the targeted genetic modification.

4. The plant of claim 1, wherein said plant is selected from the group consisting of rice, maize, soybean, sunflower, sorghum, canola, wheat, alfalfa, cotton, barley, millet, sugar cane and switchgrass.

5. A method of increasing drought tolerance in a plant, the method comprising:

(a) introducing in a regenerable plant cell a recombinant DNA construct comprising a regulatory element operably liked to a polynucleotide encoding a polypeptide comprising an amino acid sequence having at least 97% sequence identity to SEQ ID NO: 3; and (b) generating the plant, wherein the plant comprises in its genome the recombinant DNA construct and has increased expression and/or activity of the polypeptide as compared to a control plant not comprising the recombinant DNA construct and wherein the plant has increased drought tolerance as compared to the control plant.

6. A method of increasing drought tolerance in a plant, the method comprising:

(a) introducing in a regenerable plant cell a targeted genetic modification at a genomic locus that encodes the polypeptide comprising an amino acid sequence of at least 97% sequence identity compared to SEQ ID NO: 3; and (b) generating the plant, wherein the level and/or activity of the polypeptide is increased in the plant as compared to a control plant not comprising the targeted genetic modification and the plant has increased drought tolerance as compared to the control plant.

7. The method of claim 6, wherein the targeted genetic modification is introduced using an enzyme selected from the group consisting of a polynucleotide-guided endonuclease, CRISPR-Cas endonucleases, base editing deaminases, a zinc finger nuclease, a transcription activator-like effector nuclease (TALEN), and engineered site-specific meganucleases.

8. The method of claim 6, wherein the targeted genetic modification is present in (a) the coding region; (b) a non-coding region; (c) a regulatory sequence; (d) an untranslated region; or (e) any combination of (a)-(d) of the genomic locus that encodes a polypeptide comprising an amino acid sequence that is at least 97% identical to an amino acid sequence selected from the group consisting of SEQ ID NOs: 3.

9. The method of claim 5, wherein the regulatory element is a heterologous promoter.

10. The modified plant or seed of claim 1, wherein the heterologous regulatory element is a heterologous promoter.

11. The method of claim 5, wherein said plant is selected from the group consisting of rice, maize, soybean, sunflower, sorghum, canola, wheat, alfalfa, cotton, barley, millet, sugar cane and switchgrass.

12. The method of claim 6, wherein said plant is selected from the group consisting of rice, maize, soybean, sunflower, sorghum, canola, wheat, alfalfa, cotton, barley, millet, sugar cane and switchgrass.

* * * * *

SEQUENCE LISTING

```
<160> NUMBER OF SEQ ID NOS: 112

<210> SEQ ID NO 1
<211> LENGTH: 382
<212> TYPE: DNA
<213> ORGANISM: Oryza sativa

<400> SEQUENCE: 1

gacgatggag ctctggtgga tttcggcttc ggggagatgg ctgccgggct ccctctcctt     60

cttgcgaacc caacggcggc agcggcgacc aaatgcggcg gctaaggcgg ctgctagctg    120

cggctggaga tcggaacatg acggcaaccc aatggttcat ggcgaggacg gcttccggcg    180

aagtttcggc gcaaggggaa cggcggccgg ggtggagctc gaccttgcgg agccgatgga    240

ggtggcggcg caggaaggag gcagatgagg cggcgtctag ggacggctgg agcggcgccg    300

gcgtttcgag agagaaggag agcgcgggga gagcgtttcc ggcgacggcg gcggacagga    360

cttgagggga tgggtagaag ac                                             382


<210> SEQ ID NO 2
<211> LENGTH: 264
<212> TYPE: DNA
<213> ORGANISM: Oryza sativa

<400> SEQUENCE: 2

atggagctct ggtggatttc ggcttcgggg agatggctgc cgggctccct ctccttcttg     60

cgaacccaac ggcggcagcg gcgaccaaat gcggcggcta aggcggctgc tagctgcggc    120

tggagatcgg aacatgacgg caacccaatg gttcatggcg aggacggctt ccggcgaagt    180

ttcggcgcaa ggggaacggc ggccggggtg gagctcgacc ttgcggagcc gatggaggtg    240

gcggcgcagg aaggaggcag atga                                           264


<210> SEQ ID NO 3
<211> LENGTH: 87
<212> TYPE: PRT
<213> ORGANISM: Oryza sativa

<400> SEQUENCE: 3

Met Glu Leu Trp Trp Ile Ser Ala Ser Gly Arg Trp Leu Pro Gly Ser
1               5                   10                  15

Leu Ser Phe Leu Arg Thr Gln Arg Arg Gln Arg Arg Pro Asn Ala Ala
            20                  25                  30

Ala Lys Ala Ala Ala Ser Cys Gly Trp Arg Ser Glu His Asp Gly Asn
        35                  40                  45

Pro Met Val His Gly Glu Asp Gly Phe Arg Arg Ser Phe Gly Ala Arg
    50                  55                  60

Gly Thr Ala Ala Gly Val Glu Leu Asp Leu Ala Glu Pro Met Glu Val
65                  70                  75                  80
```

Ala Ala Gln Glu Gly Gly Arg
85

<210> SEQ ID NO 4
<211> LENGTH: 2903
<212> TYPE: DNA
<213> ORGANISM: Oryza sativa

<400> SEQUENCE: 4
cgcacacgtg aatacatata ttttctcgcg ccaagaagcc gcgagccctc tagcctctcg 60
cgaacctctc gatcttctcg ccgccatcgt cgtcgtcgtg gtcgatggct tccacggccg 120
ccattgctgc gctcgcgttg gtgttcttcg tgttgctgtg tgtgagagat ggtggcggcg 180
tcgacgcggc ggacacgctg tcgcaggggc agtcgctggg cgcgaacgac atgctggtgt 240
cggcgaacgg cacgttcaag gtggggttct tcacgccggc gggtggcgac ccggggaagg 300
tgtacctcgg ggtgatgtac gcgacgtcga acgtgcagac ggtgatgtgg gtggcgaacc 360
gcgatgcccc cgtgagaacg gcggcggggg ccgcctccgc caccgtgacg ggctccggcg 420
agctgctggt gaaggagggc gaccgcgtcg cgtggcggac gaacgcgtcg gccgcggggc 480
gctccaaaca cacgctgacg atccgcgacg acgggaacct cgtgatctcc ggcagcgacg 540
ccgccggcac ggacgtagag tgggagagct tccaccaccc gacggacacc ttcgtcccgg 600
gcatggagat cgcgctccgg cagaccaacg gcgaccgcac gctgtacacg tcgtggagga 660
gcgacgccga cccggccacc ggcgacttca cgctggggct ggacgcgtcg gcgcagctct 720
acatctggcg gagccagggc ggcaagaact caacctactg gaggtcgggg cagtgggcga 780
gcggcaactt cgtcggcatc ccgtggcggg cgctctacgt ctacggcttc aagttgaacg 840
gcgacccgcc gccgatcgcc ggcgacatgt ccatcgcgtt caccccottc aactcgtcgc 900 tctaccgctt cgtgctccgg ccgaacggcg tcgagacgtg ctacatgctc ctcggctccg 960
gcgactggga gctcgtctgg tcgcagccga ccatcccctg ccaccgctac aacttgtgcg 1020
gcgacaacgc cgagtgcacc gccgacgaca acgagcccat ctgcacctgc ttcacaggtt 1080
ttgagccaaa atctccgcaa gagtacaaca acggcaactg gacgcagggc tgcgtgagga 1140
gcgttccact gacgtgcagc agcgagagga acaacacgac cgccggtggc gccggcgccg 1200
gtggcggcga cgggttcacc gtcatccggg gcgtgaagct gccggacttc gccgtgtggg 1260
gatcgctggt gggcgacgcg aactcgtgcg agaaggcgtg cctgggcaac tgctcatgcg 1320
gggcgtacag ctacagcacc ggcagctgcc tcacctgggg gcaggagctg gtggacatct 1380
tccagttcca aaccggcacc gagggagcga aatacgacct ctacgtcaag gtcccatctt 1440
ctctattaga taaaagctcg gggcgatgga aaaccgttgt cgtcgtcgta gttgtggtcg 1500
tggtggttgt attgctggca tcaggccttc tcatgtggaa gtgcaggaga cgaattaaag 1560
agaaacttgg cattggtagg aaaaaggcac aactcccgtt gctgcgtcct gcgagggatg 1620
caaagcagga tttctcaggg ccagcgcaat ctgaacacga gaaatcagag gagggcaaga 1680
actgcgagct gccgctgttc gcgttcgaga ccttagcgac ggccaccgac aacttcagca 1740
tctcgaacaa gctcggagag ggaggcttcg gccatgtcta caagggaagg ctccctggag 1800
gagaagagat cgcggtgaag aggctgtccc ggagctccgg gcaggggctg gaggagttca 1860
agaacgaggt gatcctgatc gcgaagctgc agcaccgcaa tcttgtcagg ttgctgggat 1920
gctgcatcca gggcgaggag aagatcctgg tgtacgaata catgcccaac aagagcctcg 1980
acgccttcct cttcgatccg gagagaagag ggctcctgga ctggaggacg aggttccaga 2040

```
tcatcgaagg cgtggcgcga gggctcctgt acctccaccg cgactcgagg ctccgcgtgg   2100
tgcaccgcga cctcaaggcc agcaacatcc tcctcgaccg cgacatgaac cccaagatct   2160
ccgacttcgg catggccagg atcttcggcg gcgaccagaa ccaggtcaac accaaccgcg   2220
tcgtcggcac actgggctac atgtcaccgg agtacgcgat ggaggggctc ttctcggtga   2280
ggtcggacgt gtacagcttc ggcatcctca tcctggagat catcacgggc cagaagaaca   2340
gcagcttcca ccacatggag ggctccctca acatcgtcgg ctacgcgtgg cagctgtgga   2400
acggggacag agggcaggag ctgatcgacc cggcgatccg ggggacgtgc cccgcgaagg   2460
aggcgctgcg gtgcgtgcac atggcgctgc tgtgcgtgca ggaccacgcg cacgaccgcc   2520
cggacatccc ctacgtggtg ctcacgctcg gcagcgactc ctccgtgctg cccacgccgc   2580
gcccgccgac gttcacgctg cagtgcacgt cgtcgtcgtc ggggcgggac atgtactaca   2640
gggacaagga ggagtcctac tccgccaacg acctcaccgt caccatgctc caaggcaggt   2700
aggagtgcgt ataccactaa gtacgtctta aaatatagca atttagaact agattggata   2760
tattctagtc caataaatct agataaccat ttttttcaga tttattaaat taagatatat   2820
tttttaaatt attatatttt ggaacggaag gagcagtagg aggttgggtg tacaaaactg   2880
tacatagaca cgaagaaaca cgc                                           2903
```

<210> SEQ ID NO 5
<211> LENGTH: 2598
<212> TYPE: DNA
<213> ORGANISM: Oryza sativa

<400> SEQUENCE: 5

```
atggcttcca cggccgccat tgctgcgctc gcgttggtgt tcttcgtgtt gctgtgtgtg     60
agagatggtg gcggcgtcga cgcggcggac acgctgtcgc aggggcagtc gctgggcgcg    120
aacgacatgc tggtgtcggc gaacggcacg ttcaaggtgg ggttcttcac gccggcgggt    180
ggcgacccgg ggaaggtgta cctcggggtg atgtacgcga cgtcgaacgt gcagacggtg    240
atgtgggtgg cgaaccgcga tgcccccgtg agaacggcgg cgggggccgc ctccgccacc    300
gtgacgggct ccggcgagct gctggtgaag gagggcgacc gcgtcgcgtg gcggacgaac    360
gcgtcggccg cggggcgctc caaacacacg ctgacgatcc gcgacgacgg gaacctcgtg    420
atctccggca gcgacgccgc cggcacggac gtagagtggg agagcttcca ccacccgacg    480
gacaccttcg tcccgggcat ggagatcgcg ctccggcaga ccaacggcga ccgcacgctg    540
tacacgtcgt ggaggagcga cgccgacccg gccaccggcg acttcacgct ggggctggac    600
gcgtcggcgc agctctacat ctggcggagc cagggcggca agaactcaac ctactggagg    660
tcggggcagt gggcgagcgg caacttcgtc ggcatcccgt ggcgggcgct ctacgtctac    720
ggcttcaagt tgaacggcga cccgccgccg atcgccggcg acatgtccat cgcgttcacc    780
cccttcaact cgtcgctcta ccgcttcgtg ctccggccga acggcgtcga gacgtgctac    840
atgctcctcg gctccggcga ctgggagctc gtctggtcgc agccgaccat cccctgccac    900
cgctacaact tgtgcggcga caacgccgag tgcaccgccg acgacaacga gcccatctgc    960
acctgcttca caggttttga gccaaaatct ccgcaagagt acaacaacgg caactggacg   1020
cagggctgcg tgaggagcgt tccactgacg tgcagcagcg agaggaacaa cacgaccgcc   1080
ggtggcgccg gcgccggtgg cggcgacggg ttcaccgtca tccggggcgt gaagctgccg   1140
gacttcgccg tgtggggatc gctggtgggc gacgcgaact cgtgcgagaa ggcgtgcctg   1200
```

```
ggcaactgct catgcggggc gtacagctac agcaccggca gctgcctcac ctgggggcag    1260

gagctggtgg acatcttcca gttccaaacc ggcaccgagg gagcgaaata cgacctctac    1320

gtcaaggtcc catcttctct attagataaa agctcggggc gatggaaaac cgttgtcgtc    1380

gtcgtagttg tggtcgtggt ggttgtattg ctggcatcag gccttctcat gtggaagtgc    1440

aggagacgaa ttaaagagaa acttggcatt ggtaggaaaa aggcacaact cccgttgctg    1500

cgtcctgcga gggatgcaaa gcaggatttc tcagggccag cgcaatctga acacgagaaa    1560

tcagaggagg gcaagaactg cgagctgccg ctgttcgcgt tcgagacctt agcgacggcc    1620

accgacaact tcagcatctc gaacaagctc ggagagggag gcttcggcca tgtctacaag    1680

ggaaggctcc ctggaggaga agagatcgcg gtgaagaggc tgtcccggag ctccgggcag    1740

gggctggagg agttcaagaa cgaggtgatc ctgatcgcga agctgcagca ccgcaatctt    1800

gtcaggttgc tgggatgctg catccagggc gaggagaaga tcctggtgta cgaatacatg    1860

cccaacaaga gcctcgacgc cttcctcttc gatccggaga gaagagggct cctggactgg    1920

aggacgaggt tccagatcat cgaaggcgtg gcgcgagggc tcctgtacct ccaccgcgac    1980

tcgaggctcc gcgtggtgca ccgcgacctc aaggccagca acatcctcct cgaccgcgac    2040

atgaacccca agatctccga cttcggcatg gccaggatct tcggcggcga ccagaaccag    2100

gtcaacacca accgcgtcgt cggcacactg ggctacatgt caccggagta cgcgatggag    2160

gggctcttct cggtgaggtc ggacgtgtac agcttcggca tcctcatcct ggagatcatc    2220

acgggccaga agaacagcag cttccaccac atggagggct ccctcaacat cgtcggctac    2280

gcgtggcagc tgtggaacgg ggacagaggg caggagctga tcgacccggc gatccggggg    2340

acgtgccccg cgaaggaggc gctgcggtgc gtgcacatgg cgctgctgtg cgtgcaggac    2400

cacgcgcacg accgcccgga catcccctac gtggtgctca cgctcggcag cgactcctcc    2460

gtgctgccca cgccgcgccc gccgacgttc acgctgcagt gcacgtcgtc gtcgtcgggg    2520

cgggacatgt actacaggga caaggaggag tcctactccg ccaacgacct caccgtcacc    2580

atgctccaag gcaggtag                                                  2598
```

<210> SEQ ID NO 6
<211> LENGTH: 865
<212> TYPE: PRT
<213> ORGANISM: Oryza sativa

<400> SEQUENCE: 6

```
Met Ala Ser Thr Ala Ala Ile Ala Ala Leu Ala Leu Val Phe Phe Val
1               5                   10                  15

Leu Leu Cys Val Arg Asp Gly Gly Gly Val Asp Ala Ala Asp Thr Leu
            20                  25                  30

Ser Gln Gly Gln Ser Leu Gly Ala Asn Asp Met Leu Val Ser Ala Asn
        35                  40                  45

Gly Thr Phe Lys Val Gly Phe Phe Thr Pro Ala Gly Gly Asp Pro Gly
    50                  55                  60

Lys Val Tyr Leu Gly Val Met Tyr Ala Thr Ser Asn Val Gln Thr Val
65                  70                  75                  80

Met Trp Val Ala Asn Arg Asp Ala Pro Val Arg Thr Ala Ala Gly Ala
                85                  90                  95

Ala Ser Ala Thr Val Thr Gly Ser Gly Glu Leu Leu Val Lys Glu Gly
            100                 105                 110

Asp Arg Val Ala Trp Arg Thr Asn Ala Ser Ala Ala Gly Arg Ser Lys
        115                 120                 125
```

```
His Thr Leu Thr Ile Arg Asp Asp Gly Asn Leu Val Ile Ser Gly Ser
    130                 135                 140

Asp Ala Ala Gly Thr Asp Val Glu Trp Glu Ser Phe His His Pro Thr
145                 150                 155                 160

Asp Thr Phe Val Pro Gly Met Glu Ile Ala Leu Arg Gln Thr Asn Gly
                165                 170                 175

Asp Arg Thr Leu Tyr Thr Ser Trp Arg Ser Asp Ala Asp Pro Ala Thr
            180                 185                 190

Gly Asp Phe Thr Leu Gly Leu Asp Ala Ser Ala Gln Leu Tyr Ile Trp
        195                 200                 205

Arg Ser Gln Gly Gly Lys Asn Ser Thr Tyr Trp Arg Ser Gly Gln Trp
    210                 215                 220

Ala Ser Gly Asn Phe Val Gly Ile Pro Trp Arg Ala Leu Tyr Val Tyr
225                 230                 235                 240

Gly Phe Lys Leu Asn Gly Asp Pro Pro Pro Ile Ala Gly Asp Met Ser
                245                 250                 255

Ile Ala Phe Thr Pro Phe Asn Ser Ser Leu Tyr Arg Phe Val Leu Arg
            260                 265                 270

Pro Asn Gly Val Glu Thr Cys Tyr Met Leu Leu Gly Ser Gly Asp Trp
        275                 280                 285

Glu Leu Val Trp Ser Gln Pro Thr Ile Pro Cys His Arg Tyr Asn Leu
    290                 295                 300

Cys Gly Asp Asn Ala Glu Cys Thr Ala Asp Asp Asn Glu Pro Ile Cys
305                 310                 315                 320

Thr Cys Phe Thr Gly Phe Glu Pro Lys Ser Pro Gln Glu Tyr Asn Asn
                325                 330                 335

Gly Asn Trp Thr Gln Gly Cys Val Arg Ser Val Pro Leu Thr Cys Ser
            340                 345                 350

Ser Glu Arg Asn Asn Thr Thr Ala Gly Gly Ala Gly Ala Gly Gly Gly
        355                 360                 365

Asp Gly Phe Thr Val Ile Arg Gly Val Lys Leu Pro Asp Phe Ala Val
    370                 375                 380

Trp Gly Ser Leu Val Gly Asp Ala Asn Ser Cys Glu Lys Ala Cys Leu
385                 390                 395                 400

Gly Asn Cys Ser Cys Gly Ala Tyr Ser Tyr Ser Thr Gly Ser Cys Leu
                405                 410                 415

Thr Trp Gly Gln Glu Leu Val Asp Ile Phe Gln Phe Gln Thr Gly Thr
            420                 425                 430

Glu Gly Ala Lys Tyr Asp Leu Tyr Val Lys Val Pro Ser Ser Leu Leu
        435                 440                 445

Asp Lys Ser Ser Gly Arg Trp Lys Thr Val Val Val Val Val Val Val
    450                 455                 460

Val Val Val Val Val Leu Leu Ala Ser Gly Leu Leu Met Trp Lys Cys
465                 470                 475                 480

Arg Arg Arg Ile Lys Glu Lys Leu Gly Ile Gly Arg Lys Lys Ala Gln
                485                 490                 495

Leu Pro Leu Leu Arg Pro Ala Arg Asp Ala Lys Gln Asp Phe Ser Gly
            500                 505                 510

Pro Ala Gln Ser Glu His Glu Lys Ser Glu Glu Gly Lys Asn Cys Glu
        515                 520                 525

Leu Pro Leu Phe Ala Phe Glu Thr Leu Ala Thr Ala Thr Asp Asn Phe
    530                 535                 540
```

-continued

```
Ser Ile Ser Asn Lys Leu Gly Glu Gly Gly Phe Gly His Val Tyr Lys
545                 550                 555                 560

Gly Arg Leu Pro Gly Gly Glu Glu Ile Ala Val Lys Arg Leu Ser Arg
                565                 570                 575

Ser Ser Gly Gln Gly Leu Glu Glu Phe Lys Asn Glu Val Ile Leu Ile
            580                 585                 590

Ala Lys Leu Gln His Arg Asn Leu Val Arg Leu Leu Gly Cys Cys Ile
        595                 600                 605

Gln Gly Glu Glu Lys Ile Leu Val Tyr Glu Tyr Met Pro Asn Lys Ser
    610                 615                 620

Leu Asp Ala Phe Leu Phe Asp Pro Glu Arg Arg Gly Leu Leu Asp Trp
625                 630                 635                 640

Arg Thr Arg Phe Gln Ile Ile Glu Gly Val Ala Arg Gly Leu Leu Tyr
                645                 650                 655

Leu His Arg Asp Ser Arg Leu Arg Val Val His Arg Asp Leu Lys Ala
            660                 665                 670

Ser Asn Ile Leu Leu Asp Arg Asp Met Asn Pro Lys Ile Ser Asp Phe
        675                 680                 685

Gly Met Ala Arg Ile Phe Gly Gly Asp Gln Asn Gln Val Asn Thr Asn
    690                 695                 700

Arg Val Val Gly Thr Leu Gly Tyr Met Ser Pro Glu Tyr Ala Met Glu
705                 710                 715                 720

Gly Leu Phe Ser Val Arg Ser Asp Val Tyr Ser Phe Gly Ile Leu Ile
                725                 730                 735

Leu Glu Ile Ile Thr Gly Gln Lys Asn Ser Ser Phe His His Met Glu
            740                 745                 750

Gly Ser Leu Asn Ile Val Gly Tyr Ala Trp Gln Leu Trp Asn Gly Asp
        755                 760                 765

Arg Gly Gln Glu Leu Ile Asp Pro Ala Ile Arg Gly Thr Cys Pro Ala
    770                 775                 780

Lys Glu Ala Leu Arg Cys Val His Met Ala Leu Leu Cys Val Gln Asp
785                 790                 795                 800

His Ala His Asp Arg Pro Asp Ile Pro Tyr Val Val Leu Thr Leu Gly
                805                 810                 815

Ser Asp Ser Ser Val Leu Pro Thr Pro Arg Pro Pro Thr Phe Thr Leu
            820                 825                 830

Gln Cys Thr Ser Ser Ser Ser Gly Arg Asp Met Tyr Tyr Arg Asp Lys
        835                 840                 845

Glu Glu Ser Tyr Ser Ala Asn Asp Leu Thr Val Thr Met Leu Gln Gly
    850                 855                 860

Arg
865
```

<210> SEQ ID NO 7
<211> LENGTH: 1336
<212> TYPE: DNA
<213> ORGANISM: Oryza sativa

<400> SEQUENCE: 7

```
ctcgtcgcgg ccgtggaaat tgccatgatg acgccgggat cgtcctcgac ttcggtgccg      60

ggagatgagg ccgacgccgg caactgggat gcgggggtgg agacggcggc gcggctggag     120

gcgatggttc atgcggagga cgaactctcg gaggagcaga ttcaagccaa caaccagaca     180

caggaagatg agctgctggc actacaggcc atctatggtg atgatttggt tatcttcgac     240
```

```
aataaggacg gccttcgatt tttccagatt tctctgcact atcaactcgc cggtgacatc    300
cgagtttacc tgaatgtctg ccccaacggg agaacagaaa ccggagcaga aaacgacgac    360
gacgacgaca gtgaccgact cttgtatgct tgcagcctgc agcatctgcc tcctgttgtg    420
ctagcctgcc tactaccacg tttatatccg agtcaccgtg cccccctactt cgtggtcgcc    480
gcgaagtggc tggacgagcc ggaagtttca agcttctgct ctgttcttga tgagatctgg    540
gcagagcagc ctgcagggca agaggtggtg tacaaatggg tggactggct gagcacctct    600
tcctggtttt gcattgcttc agatgatcag attgtatttg gaccagatgc agactcggct    660
ggtggtgatg accgggcaat cggaagaagc tgctcccttg attctatgat ccctctaatt    720
caacgttaca gcaaggagag atcacatgaa attttcgctc gaagaatcca tgagtgcgga    780
gtctgtctca gtgaaaatac aggcagaaac ttcatacagc tcccatgcag ccactccttc    840
tgcgtcaagt gcatggagac gcagtgcagg atccacgtga aggaagggag cgtggcgagg    900
ctgacatgcc cggacacgtc gtgccgccgg ccgctgccgc cggcgctgct gaggggcctc    960
ctcggcgacg gcgagtacgc gcggtgggag tcgctggtgc tgcgaggatg ctggacacga   1020
tgcccgacgt ggcctactgc cccaggtgca gcgccgcgtg cgtggcggcc ggcgacgacg   1080
cccagtgctc gaggtgcttc ttcaccttct gcgccgtctg ccgggagcgg cgccacgtcg   1140
gggacacctg cgtctccccg aaccagatgc tcgacatcat gctggaacgg cagaaggaga   1200
agaggccgtt ggcggcgccg tcgccggaca gccaggcggt gtcgtcgaag aggaagatgg   1260
aggagcttct gagcctccgc gaggtgatgc gcacgtcgag gcagtgcccg tcgtgcaaga   1320
tggccgtgtc caagac                                                   1336
```

<210> SEQ ID NO 8
<211> LENGTH: 1248
<212> TYPE: DNA
<213> ORGANISM: Oryza sativa

<400> SEQUENCE: 8

```
atgatgacgc cgggatcgtc ctcgacttcg gtgccgggag atgaggccga cgccggcaac     60
tgggatgcgg gggtggagac ggcggcgcgg ctggaggcga tggttcatgc ggaggacgaa    120
ctctcggagg agcagattca agccaacaac cagacacagg aagatgagct gctggcacta    180
caggccatct atggtgatga tttggttatc ttcgacaata aggacggcct tcgatttttc    240
cagatttctc tgcactatca actcgccggt gacatccgag tttacctgaa tgtctgcccc    300
aacgggagaa cagaaaccgg agcagaaaac gacgacgacg acgacagtga ccgactcttg    360
tatgcttgca gcctgcagca tctgcctcct gttgtgctag cctgcctact accacgttta    420
tatccgagtc accgtgcccc ctacttcgtg gtcgccgcga agtggctgga cgagccggaa    480
gtttcaagct tctgctctgt tcttgatgag atctgggcag agcagcctgc agggcaagag    540
gtggtgtaca aatgggtgga ctggctgagc acctcttcct ggttttgcat tgcttcagat    600
gatcagattg tatttggacc agatgcagac tcggctggtg gtgatgaccg ggcaatcgga    660
agaagctgct cccttgattc tatgatccct ctaattcaac gttacagcaa ggagagatca    720
catgaaattt tcgctcgaag aatccatgag tgcggagtct gtctcagtga aaatacaggc    780
agaaacttca tacagctccc atgcagccac tccttctgcg tcaagtgcat ggagacgcag    840
tgcaggatcc acgtgaagga agggagcgtg gcgaggctga catgcccgga cacgtcgtgc    900
cgccggccgc tgccgccggc gctgctgagg ggcctcctcg gcgacggcga gtacgcgcgg    960
tgggagtcgc tggtgctgcg aggatgctgg acacgatgcc cgacgtggcc tactgcccca   1020
```

ggtgcagcgc cgcgtgcgtg gcggccggcg acgacgccca gtgctcgagg tgcttcttca 1080
ccttctgcgc cgtctgccgg gagcggcgcc acgtcgggga cacctgcgtc tccccgaacc 1140
agatgctcga catcatgctg gaacggcaga aggagaagag gccgttggcg gcgccgtcgc 1200
cggacagcca ggcggtgtcg tcgaagagga agatggagga gcttctga 1248

<210> SEQ ID NO 9
<211> LENGTH: 415
<212> TYPE: PRT
<213> ORGANISM: Oryza sativa

<400> SEQUENCE: 9

Met Met Thr Pro Gly Ser Ser Ser Thr Ser Val Pro Gly Asp Glu Ala
1 5 10 15

Asp Ala Gly Asn Trp Asp Ala Gly Val Glu Thr Ala Ala Arg Leu Glu
20 25 30

Ala Met Val His Ala Glu Asp Glu Leu Ser Glu Glu Gln Ile Gln Ala
35 40 45

Asn Asn Gln Thr Gln Glu Asp Glu Leu Leu Ala Leu Gln Ala Ile Tyr
50 55 60

Gly Asp Asp Leu Val Ile Phe Asp Asn Lys Asp Gly Leu Arg Phe Phe
65 70 75 80

Gln Ile Ser Leu His Tyr Gln Leu Ala Gly Asp Ile Arg Val Tyr Leu
85 90 95

Asn Val Cys Pro Asn Gly Arg Thr Glu Thr Gly Ala Glu Asn Asp Asp
100 105 110

Asp Asp Asp Ser Asp Arg Leu Leu Tyr Ala Cys Ser Leu Gln His Leu
115 120 125

Pro Pro Val Val Leu Ala Cys Leu Leu Pro Arg Leu Tyr Pro Ser His
130 135 140

Arg Ala Pro Tyr Phe Val Val Ala Ala Lys Trp Leu Asp Glu Pro Glu
145 150 155 160

Val Ser Ser Phe Cys Ser Val Leu Asp Glu Ile Trp Ala Glu Gln Pro
165 170 175

Ala Gly Gln Glu Val Val Tyr Lys Trp Val Asp Trp Leu Ser Thr Ser
180 185 190

Ser Trp Phe Cys Ile Ala Ser Asp Asp Gln Ile Val Phe Gly Pro Asp
195 200 205

Ala Asp Ser Ala Gly Gly Asp Asp Arg Ala Ile Gly Arg Ser Cys Ser
210 215 220

Leu Asp Ser Met Ile Pro Leu Ile Gln Arg Tyr Ser Lys Glu Arg Ser
225 230 235 240

His Glu Ile Phe Ala Arg Arg Ile His Glu Cys Gly Val Cys Leu Ser
245 250 255

Glu Asn Thr Gly Arg Asn Phe Ile Gln Leu Pro Cys Ser His Ser Phe
260 265 270

Cys Val Lys Cys Met Glu Thr Gln Cys Arg Ile His Val Lys Glu Gly
275 280 285

Ser Val Ala Arg Leu Thr Cys Pro Asp Thr Ser Cys Arg Arg Pro Leu
290 295 300

Pro Pro Ala Leu Leu Arg Gly Leu Leu Gly Asp Gly Glu Tyr Ala Arg
305 310 315 320

Trp Glu Ser Leu Val Leu Arg Gly Cys Trp Thr Arg Cys Pro Thr Trp
325 330 335

```
Pro Thr Ala Pro Gly Ala Ala Pro Arg Ala Trp Arg Pro Ala Thr Thr
            340                 345                 350

Pro Ser Ala Arg Gly Ala Ser Ser Pro Ser Ala Pro Ser Ala Gly Ser
        355                 360                 365

Gly Ala Thr Ser Gly Thr Pro Ala Ser Pro Arg Thr Arg Cys Ser Thr
    370                 375                 380

Ser Cys Trp Asn Gly Arg Arg Arg Arg Gly Arg Trp Arg Arg Arg Arg
385                 390                 395                 400

Arg Thr Ala Arg Arg Cys Arg Arg Arg Gly Arg Trp Arg Ser Phe
                405                 410                 415
```

```
<210> SEQ ID NO 10
<211> LENGTH: 1827
<212> TYPE: DNA
<213> ORGANISM: Oryza sativa

<400> SEQUENCE: 10

gatcaatctc tcgcttcctt cccgtgaaga tgtcgtcgcc cgcgggggag gatgagaaga      60

agccggcggg gggagagggc ggcggcgccc acatcaacct caaggtcaag ggacaggtgc     120

gttttcctcc tgccccttca cctgggatgg agcgatcccg tggcggggtt gattgcgtga     180

tcggaatcgc gtcgattcta tctagatgtg aatgtgttcg cttcctttgt agggattatg     240

gggcgtctgc tcttgcgatc gaaatcgcga tcggaattgc gttgtgatgt ggtcttaggg     300

tttgtaggtt ggaatttcaa ttccctattt gggcgttgtt tgatataagt ttgggtagaa     360

gaggaagttt tagccgtagg aattatcgat cgatttgtgc tagggcatgg ccgacctttg     420

agtttctagc agcgaggtac tcctacatga tgggagaatt ggttaagcac ataggggttg     480

tttatcatca gtaaaaattc cagtccaata caacttactc ttgatcattg gtaattttgt     540

ttgaggcgtt aaccttgata tggtactctc ttatgatttt ttgttccgag tatacatgat     600

aatttagttg aattttcatt cagattatca gttcctatga tgttttagtt gatgctggtg     660

ggtatcatac tctcttagtt cgcaatggct gaaaggagtt tttgttcagc gatacagaac     720

aatttgttga agccaaatgg gatgtttcat tgctcagtat ctccttcata cagcattgat     780

cataattagt ttaaacccta gttagttgca ttctcgattt agactctggc attctcgaac     840

atctgagtca taggcacaca actatgcaca tcctttggct agttaattgt aatgatattc     900

agagcaaatc tgatctgtgt atgcctgttg cattttctgt ctggaattgt taatatggtt     960

tttttcaaat actgccttat aggacatttt catgtaccag ggctgagttt ttttgtgtta    1020

aatactcata aaggggagac ttgctagttg catgcatatc ataagttgca gacaattctc    1080

aatttctgag tgtccagata aaatataatg gcaagaattt gagaatatgc atttgtctgt    1140

ggttgtgtgc taataggata ttatacttca attcaaaagt tttagatcac tcataaattt    1200

gcatcaactt tgaagttgaa tcatttatca attgagtcac tacgctgcaa attgaaaaca    1260

atgcatttat ttgtttgcga tgatgagatg ttgccagatt tttttttctt ttgttagtaa    1320

agtgcatttt atgttttggc gccataaaac cttatcattc cttgtgctgt aggatggcaa    1380

cgaggtgttc tttcgtatca agagatcaac ccaactgaag aagctgatga acgcctactg    1440

tgatcgccag tccgtggata tcaaatctat tgccttcctg tttgatggtc gtaggctcaa    1500

tgctgagcag acccctgacc aggtgcgtga tataccatac tgccttctct aaacaatgag    1560

ctgatgcaaa tactgccttc cctaaaaccc agtgctatag ctgatgcttt tttaccactg    1620

caaactgttt gatttcagct cgagatggaa gacggcgacg agattgacgc catgcttcac    1680
```

```
cagactgggg gctctctgcc tgcctagagc tcatatgaag ctgttgcaac aatgcaaccg   1740

cattactatt ttctgccttg ttagagtcag tcagtctaga ggacatgaaa ctagtctaaa   1800

gaacttgtga atcgtttggt cctgtgc                                      1827


<210> SEQ ID NO 11
<211> LENGTH: 306
<212> TYPE: DNA
<213> ORGANISM: Oryza sativa

<400> SEQUENCE: 11

atgtcgtcgc ccgcggggga ggatgagaag aagccggcgg ggggagaggg cggcggcgcc     60

cacatcaacc tcaaggtcaa gggacaggat ggcaacgagg tgttctttcg tatcaagaga    120

tcaacccaac tgaagaagct gatgaacgcc tactgtgatc gccagtccgt ggatatcaaa    180

tctattgcct tcctgtttga tggtcgtagg ctcaatgctg agcagacccc tgaccagctc    240

gagatggaag acggcgacga gattgacgcc atgcttcacc agactggggg ctctctgcct    300

gcctag                                                              306


<210> SEQ ID NO 12
<211> LENGTH: 101
<212> TYPE: PRT
<213> ORGANISM: Oryza sativa

<400> SEQUENCE: 12

Met Ser Ser Pro Ala Gly Glu Asp Glu Lys Lys Pro Ala Gly Gly Glu
1               5                   10                  15

Gly Gly Gly Ala His Ile Asn Leu Lys Val Lys Gly Gln Asp Gly Asn
            20                  25                  30

Glu Val Phe Phe Arg Ile Lys Arg Ser Thr Gln Leu Lys Lys Leu Met
        35                  40                  45

Asn Ala Tyr Cys Asp Arg Gln Ser Val Asp Ile Lys Ser Ile Ala Phe
    50                  55                  60

Leu Phe Asp Gly Arg Arg Leu Asn Ala Glu Gln Thr Pro Asp Gln Leu
65                  70                  75                  80

Glu Met Glu Asp Gly Asp Glu Ile Asp Ala Met Leu His Gln Thr Gly
                85                  90                  95

Gly Ser Leu Pro Ala
            100


<210> SEQ ID NO 13
<211> LENGTH: 2186
<212> TYPE: DNA
<213> ORGANISM: Oryza sativa

<400> SEQUENCE: 13

gtcgaaaccg agttgatctc gctatgctcc gagtcggatt ccagcttggc acacggaagc     60

cgcgaacgaa agcgtatttt gtgattacgt ttagggtggc tctattttga tttctacgga    120

atacgtattc cttgtttgaa cacggcttta gttagtaaca ctcaccaatt gggacgaaca    180

cctcgactcc tcgagtcacc aatggcgatt ccccgtcgcc tcgccgccgc cgcggccgcc    240

gaaaccacca aacgctcggc ggcaggtctc gccgccgccc tcggtggaag cggagggaag    300

cccgcaacag ccgacctggc cgctgccgcg acggccgcgg cggccgccgg tcgcgcctcc    360

gaatgccagt ccctcctcct ccgcatgtcg cgccgccgcg gcgcctgccg tcgcgagatc    420

gtctcctccc tcctcggctc ctcccccacc ccgcagccgc gggtgtttga cctcctaatc    480
```

```
cgcacctaca cccagtcccg caagccccgc gaggccttcg aggcattccg cctcatcctc    540

gaccaccgcg tccccatccc cgccgccgcc tccaacgccc tgctcgccgc cctctcccgc    600

gccggatggc cccatctcgc cgcggacgcc taccgccttg tcttctcctc caactccgag    660

gtaaacacgt acacgcttaa cataatggtc cacaactact gcaaagccct ggagttcgac    720

aaggttgacg ctgtcatctc cgagatggag aagagatgtg tctttcctga tgtggttaca    780

cataatgtga tggttgatgc tagatttcgc gctggggacg cggaggcagc aatggcgttg    840

gttgactcaa tggttagtaa agggctaaag cctgggattg tgacgtataa ttcggttctg    900

aaagggttat gtaggagtgg gatgtgggat aaagcatggg aagtgttcaa agaaatggat    960

gattttggtg ttgcgcctga tgttcggagt tttaccattt tgattggggg attttgtaga   1020

gttggggaga ttgaggaggc gttgaagatt tacaaggaga tgcggcaccg tggtattaaa   1080

ccagatttgg tgagctttag ttgcttaatt ggattgtttg caaggagggg gaagatggac   1140

catgcgatgg cgtacttgag ggagatgagg tgctttggat tggtacccga tggtgtgatt   1200

tacacaatgg taataggcgg attttgtagg gctgggttaa tgtcagatgc tctgagagtt   1260

agggatgaga tggttggctg tggatgtttg ccagatgtgg taacttacaa tactttgttg   1320

aatgggctct gtaaagagcg caggttgtta gatgcagaag ggcttttgaa tgagatgagg   1380

gagagagggg ttccaccaga tttatgtacc ttcacaactt tgattcacgg gtattgcata   1440

gagggtaaac tagacaaggc gctgcaactg tttgacacaa tgttgaacca gcgtttgagg   1500

ccagacatag taacatataa tactttgatc gacggaatgt gcagacaagg tgatcttgac   1560

aaagccaatg atctatggga tgatatgcat tctcgtgaaa tcttccccaa tcatgttacg   1620

tacagtatcc taatcgacag tcactgtgag aagggacaag tggaagatgc atttggtttt   1680

ttggatgaaa tgataaataa gggcattttg ccaaacatca tgacatataa ttccatcatt   1740

aagggctatt gccggtctgg aaatgtttca aaggggcaga agttcttgca aaagatgatg   1800

gtcaacaagg tgtcacctga tttaattact tacaacaccc taatccatgg ttatatcaaa   1860

gaagataaga tgcacgatgc ttttaagttg cttaacatga tggagaagga aaaggttcaa   1920

ccagatgttg tcacatataa tatgctcata aatgggtttt ctgtacatgg taatgtgcaa   1980

gaagctggtt ggatttttga gaaaatgtgt gctaaaggaa ttgaaccaga tagatataca   2040

tacatgtcta tgataaatgg tcatgtcaca gctggcaact cgaaggaggc attccagctt   2100

catgatgaga tgcttcaaag agggtttgct cctgacgata aattctgagg gtcctcattt   2160

tcttctttat tggattccgt agagcc                                        2186
```

<210> SEQ ID NO 14
<211> LENGTH: 1947
<212> TYPE: DNA
<213> ORGANISM: Oryza sativa

<400> SEQUENCE: 14

```
atggcgattc cccgtcgcct cgccgccgcc gcggccgccg aaaccaccaa acgctcggcg     60

gcaggtctcg ccgccgccct cggtggaagc ggagggaagc ccgcaacagc cgacctggcc    120

gctgccgcga cggccgcggc ggccgccggt cgcgcctccg aatgccagtc cctcctcctc    180

cgcatgtcgc gccgccgcgg cgcctgccgt cgcgagatcg tctcctccct cctcggctcc    240

tcccccaccc cgcagccgcg ggtgtttgac ctcctaatcc gcacctacac ccagtcccgc    300

aagccccgcg aggccttcga ggcattccgc ctcatcctcg accaccgcgt ccccatcccc    360
```

```
gccgccgcct ccaacgccct gctcgccgcc ctctcccgcg ccggatggcc ccatctcgcc    420

gcggacgcct accgccttgt cttctcctcc aactccgagg taaacacgta cacgcttaac    480

ataatggtcc acaactactg caaagccctg gagttcgaca aggttgacgc tgtcatctcc    540

gagatggaga agagatgtgt ctttcctgat gtggttacac ataatgtgat ggttgatgct    600

agatttcgcg ctggggacgc ggaggcagca atggcgttgg ttgactcaat ggttagtaaa    660

gggctaaagc ctgggattgt gacgtataat tcggttctga aagggttatg taggagtggg    720

atgtgggata aagcatggga agtgttcaaa gaaatggatg attttggtgt tgcgcctgat    780

gttcggagtt ttaccatttt gattggggga ttttgtagag ttggggagat tgaggaggcg    840

ttgaagattt acaaggagat gcggcaccgt ggtattaaac cagatttggt gagctttagt    900

tgcttaattg gattgtttgc aaggaggggg aagatggacc atgcgatggc gtacttgagg    960

gagatgaggt gctttggatt ggtacccgat ggtgtgattt acacaatggt aataggcgga   1020

ttttgtaggg ctgggttaat gtcagatgct ctgagagtta gggatgagat ggttggctgt   1080

ggatgtttgc cagatgtggt aacttacaat actttgttga atgggctctg taaagagcgc   1140

aggttgttag atgcagaagg gcttttgaat gagatgaggg agagaggggt tccaccagat   1200

ttatgtacct tcacaacttt gattcacggg tattgcatag agggtaaact agacaaggcg   1260

ctgcaactgt ttgacacaat gttgaaccag cgtttgaggc cagacatagt aacatataat   1320

actttgatcg acggaatgtg cagacaaggt gatcttgaca aagccaatga tctatgggat   1380

gatatgcatt ctcgtgaaat cttccccaat catgttacgt acagtatcct aatcgacagt   1440

cactgtgaga agggacaagt ggaagatgca tttggttttt tggatgaaat gataaataag   1500

ggcattttgc caaacatcat gacatataat tccatcatta agggctattg ccggtctgga   1560

aatgtttcaa aggggcagaa gttcttgcaa aagatgatgg tcaacaaggt gtcacctgat   1620

ttaattactt acaacaccct aatccatggt tatatcaaag aagataagat gcacgatgct   1680

tttaagttgc ttaacatgat ggagaaggaa aaggttcaac cagatgttgt cacatataat   1740

atgctcataa atgggttttc tgtacatggt aatgtgcaag aagctggttg gatttttgag   1800

aaaatgtgtg ctaaaggaat tgaaccagat agatatacat acatgtctat gataaatggt   1860

catgtcacag ctggcaactc gaaggaggca ttccagcttc atgatgagat gcttcaaaga   1920

gggtttgctc ctgacgataa attctga                                       1947
```

```
<210> SEQ ID NO 15
<211> LENGTH: 648
<212> TYPE: PRT
<213> ORGANISM: Oryza sativa

<400> SEQUENCE: 15

Met Ala Ile Pro Arg Arg Leu Ala Ala Ala Ala Ala Ala Glu Thr Thr
1               5                   10                  15

Lys Arg Ser Ala Ala Gly Leu Ala Ala Ala Leu Gly Gly Ser Gly Gly
            20                  25                  30

Lys Pro Ala Thr Ala Asp Leu Ala Ala Ala Ala Thr Ala Ala Ala Ala
        35                  40                  45

Ala Gly Arg Ala Ser Glu Cys Gln Ser Leu Leu Leu Arg Met Ser Arg
    50                  55                  60

Arg Arg Gly Ala Cys Arg Arg Glu Ile Val Ser Ser Leu Leu Gly Ser
65                  70                  75                  80

Ser Pro Thr Pro Gln Pro Arg Val Phe Asp Leu Leu Ile Arg Thr Tyr
                85                  90                  95
```

```
Thr Gln Ser Arg Lys Pro Arg Glu Ala Phe Glu Ala Phe Arg Leu Ile
            100                 105                 110

Leu Asp His Arg Val Pro Ile Pro Ala Ala Ala Ser Asn Ala Leu Leu
        115                 120                 125

Ala Ala Leu Ser Arg Ala Gly Trp Pro His Leu Ala Ala Asp Ala Tyr
    130                 135                 140

Arg Leu Val Phe Ser Ser Asn Ser Glu Val Asn Thr Tyr Thr Leu Asn
145                 150                 155                 160

Ile Met Val His Asn Tyr Cys Lys Ala Leu Glu Phe Asp Lys Val Asp
                165                 170                 175

Ala Val Ile Ser Glu Met Glu Lys Arg Cys Val Phe Pro Asp Val Val
            180                 185                 190

Thr His Asn Val Met Val Asp Ala Arg Phe Arg Ala Gly Asp Ala Glu
        195                 200                 205

Ala Ala Met Ala Leu Val Asp Ser Met Val Ser Lys Gly Leu Lys Pro
    210                 215                 220

Gly Ile Val Thr Tyr Asn Ser Val Leu Lys Gly Leu Cys Arg Ser Gly
225                 230                 235                 240

Met Trp Asp Lys Ala Trp Glu Val Phe Lys Glu Met Asp Asp Phe Gly
                245                 250                 255

Val Ala Pro Asp Val Arg Ser Phe Thr Ile Leu Ile Gly Gly Phe Cys
            260                 265                 270

Arg Val Gly Glu Ile Glu Glu Ala Leu Lys Ile Tyr Lys Glu Met Arg
        275                 280                 285

His Arg Gly Ile Lys Pro Asp Leu Val Ser Phe Ser Cys Leu Ile Gly
    290                 295                 300

Leu Phe Ala Arg Arg Gly Lys Met Asp His Ala Met Ala Tyr Leu Arg
305                 310                 315                 320

Glu Met Arg Cys Phe Gly Leu Val Pro Asp Gly Val Ile Tyr Thr Met
                325                 330                 335

Val Ile Gly Gly Phe Cys Arg Ala Gly Leu Met Ser Asp Ala Leu Arg
            340                 345                 350

Val Arg Asp Glu Met Val Gly Cys Gly Cys Leu Pro Asp Val Val Thr
        355                 360                 365

Tyr Asn Thr Leu Leu Asn Gly Leu Cys Lys Glu Arg Arg Leu Leu Asp
    370                 375                 380

Ala Glu Gly Leu Leu Asn Glu Met Arg Glu Arg Gly Val Pro Pro Asp
385                 390                 395                 400

Leu Cys Thr Phe Thr Thr Leu Ile His Gly Tyr Cys Ile Glu Gly Lys
                405                 410                 415

Leu Asp Lys Ala Leu Gln Leu Phe Asp Thr Met Leu Asn Gln Arg Leu
            420                 425                 430

Arg Pro Asp Ile Val Thr Tyr Asn Thr Leu Ile Asp Gly Met Cys Arg
        435                 440                 445

Gln Gly Asp Leu Asp Lys Ala Asn Asp Leu Trp Asp Asp Met His Ser
    450                 455                 460

Arg Glu Ile Phe Pro Asn His Val Thr Tyr Ser Ile Leu Ile Asp Ser
465                 470                 475                 480

His Cys Glu Lys Gly Gln Val Glu Asp Ala Phe Gly Phe Leu Asp Glu
                485                 490                 495

Met Ile Asn Lys Gly Ile Leu Pro Asn Ile Met Thr Tyr Asn Ser Ile
            500                 505                 510
```

```
Ile Lys Gly Tyr Cys Arg Ser Gly Asn Val Ser Lys Gly Gln Lys Phe
        515                 520                 525

Leu Gln Lys Met Met Val Asn Lys Val Ser Pro Asp Leu Ile Thr Tyr
    530                 535                 540

Asn Thr Leu Ile His Gly Tyr Ile Lys Glu Asp Lys Met His Asp Ala
545                 550                 555                 560

Phe Lys Leu Leu Asn Met Met Glu Lys Glu Lys Val Gln Pro Asp Val
                565                 570                 575

Val Thr Tyr Asn Met Leu Ile Asn Gly Phe Ser Val His Gly Asn Val
            580                 585                 590

Gln Glu Ala Gly Trp Ile Phe Glu Lys Met Cys Ala Lys Gly Ile Glu
        595                 600                 605

Pro Asp Arg Tyr Thr Tyr Met Ser Met Ile Asn Gly His Val Thr Ala
    610                 615                 620

Gly Asn Ser Lys Glu Ala Phe Gln Leu His Asp Glu Met Leu Gln Arg
625                 630                 635                 640

Gly Phe Ala Pro Asp Asp Lys Phe
                645


<210> SEQ ID NO 16
<211> LENGTH: 435
<212> TYPE: DNA
<213> ORGANISM: Oryza sativa

<400> SEQUENCE: 16

cgatgatggt gatgggctac ttgctggcgc ccaagaaggg cgggaggagg aggaggggga     60

aggatcagcc gtcggcggcg gcgcatcacg gcgataacga cgatggactc cgggagacgc    120

tgctggagca gcagcagcag ccggcgtcgt cgtcgtcgcc gacggccggt ggcggcggcg    180

tgccgaaggg gtacttcgcg gtgtacgtcg gcgaggaggc gcggcggttc gtggtgccca    240

cggggtacct ccgcgagccg gcgttccggg acctcatgga gcgcgccgcc gacgagttcg    300

gcttcgccca ggccggcggc ctccgcgtgc cctgcggcga ggacgacttc gaggatctcc    360

tccgccgcct ccgccgcaag aacggcggcg ccgccgccgc caaggctaag aaagccatca    420

gctagccacg cgtac                                                     435


<210> SEQ ID NO 17
<211> LENGTH: 423
<212> TYPE: DNA
<213> ORGANISM: Oryza sativa

<400> SEQUENCE: 17

atgatggtga tgggctactt gctggcgccc aagaagggcg ggaggaggag gagggggaag     60

gatcagccgt cggcggcggc gcatcacggc gataacgacg atggactccg ggagacgctg    120

ctggagcagc agcagcagcc ggcgtcgtcg tcgtcgccga cggccggtgg cggcggcgtg    180

ccgaaggggt acttcgcggt gtacgtcggc gaggaggcgc ggcggttcgt ggtgcccacg    240

gggtacctcc gcgagccggc gttccgggac ctcatggagc gcgccgccga cgagttcggc    300

ttcgcccagg ccggcggcct ccgcgtgccc tgcggcgagg acgacttcga ggatctcctc    360

cgccgcctcc gccgcaagaa cggcggcgcc gccgccgcca aggctaagaa agccatcagc    420

tag                                                                  423


<210> SEQ ID NO 18
<211> LENGTH: 140
<212> TYPE: PRT
```

<213> ORGANISM: Oryza sativa

<400> SEQUENCE: 18

```
Met Met Val Met Gly Tyr Leu Leu Ala Pro Lys Lys Gly Gly Arg Arg
1               5                   10                  15

Arg Arg Gly Lys Asp Gln Pro Ser Ala Ala Ala His His Gly Asp Asn
            20                  25                  30

Asp Asp Gly Leu Arg Glu Thr Leu Leu Glu Gln Gln Gln Gln Pro Ala
        35                  40                  45

Ser Ser Ser Ser Pro Thr Ala Gly Gly Gly Gly Val Pro Lys Gly Tyr
    50                  55                  60

Phe Ala Val Tyr Val Gly Glu Glu Ala Arg Arg Phe Val Val Pro Thr
65                  70                  75                  80

Gly Tyr Leu Arg Glu Pro Ala Phe Arg Asp Leu Met Glu Arg Ala Ala
                85                  90                  95

Asp Glu Phe Gly Phe Ala Gln Ala Gly Gly Leu Arg Val Pro Cys Gly
            100                 105                 110

Glu Asp Asp Phe Glu Asp Leu Leu Arg Arg Leu Arg Arg Lys Asn Gly
        115                 120                 125

Gly Ala Ala Ala Ala Lys Ala Lys Lys Ala Ile Ser
    130                 135                 140
```

<210> SEQ ID NO 19
<211> LENGTH: 2695
<212> TYPE: DNA
<213> ORGANISM: Oryza sativa

<400> SEQUENCE: 19

```
caaatctcac gcggcgcttt ctctctctcc cgcgagatgg acgccgcggc ggcgtcctcc      60

tcctcctcct cgtcggcgac gatggcggcg gcggcggcgt cggccgcgga ggcgtcgttg     120

tccggctcgc ctgcttcttc gaggaacgct cgccatcggc agcgtaaggg ggtccggctc     180

cggatgctgc gacggcgggg gcggcagcct gtggaggccg agcgcgcccc gggcgatggg     240

ggcggtggcg ccgtgcagga ggatctcgcg ctgcctctcg gaatgtcctt cgccgccgtc     300

ctcgcgcagg tgcgtcatgg cgggtggatt tccttatagg caaaccctga agaaagtagt     360

agtactagta ctttttttctt ccttggcgct gttcgtgatc ctctctgcga tgttcgtgcc     420

atcaaatgta ctagcatatt gcgtgtagat tctgttgcta gcgtctcacg aacacggtaa     480

tctgagaggt tgcgtgctct ggatggtagc ttagaatggg aaatggaacg ttagacgcgg     540

cagcttgggg ccgaggaaat tctttgtgct atacttccct caatggaaat gtcattgagc     600

caaaataaaa aaaagtcatt ttagttcaca gctatatgct cagatttttc acaaataagg     660

ggaaaaacta ggatgcaaaa tgatgagaac aaggaatgat tatgaataag acagcagaga     720

aattgggctt gacaatgttg tggctttatg ggttatgcaa gccttgtact tttgtcaaat     780

aagtagtgtg gcatttaccg tcttattgca aaattcaact tcattgctac tattattctt     840

catttccata cttatagtgg acatgaaatt aaatagtcat ttcgataata ctaccccgtc     900

atcctgtcat tggacattaa attagtcaca gttcagcatc tcttcatccg aaagcttgca     960

ctatagcagc attttgaaca cagatgcata tgcatgtgca aagtctatct aatattcacc    1020

tgcgtacatc tggacatttg cattagtaat tataaataaa catgtttgta caccggttta    1080

gccctatgcc cttattgttc aggtaacaag gagctgcttt cgttgaccgc aggttataaa    1140

tacaaagaat atttcaggac aaagattaca tcctgatttc ctctccaagg tacgtgcttt    1200
```

```
ctaatttgat ttatgaactc tgttatccat aaacccacaa attgatggtc tgaaattggg   1260
tttgagtgta gatctgtaca tcagcagtca aggaatctct gacaaatgta agcccggcta   1320
ccactattat tcagttctca ttgtctctta gtattcattg taatatcctt taattatcgt   1380
ttctgtagat atatggtgac agttccaaca gtttcatcaa aaatttcgaa aaatctttca   1440
gcagcacttt taggacgctt catcttgtta atgaaatacc tgtgaatgag agaagtcata   1500
ttcctgaatg ttcttttaaa catgatgatt ctgtggctgt ggacagcttg agctcatctg   1560
atttgcaaaa tcagacaaac agaatagagc atgaccttgt gaacacagtg gaaagtcaac   1620
tagttctctt tgccagtgac aatcagcagt taacgcatct tcggcatagc agatcctctc   1680
ctgaagctga taatcgcatt cttaatgcca ttgatcgctc gaacgaactc aaggaatttg   1740
aaatagggct taccatgaga aagttgcaac tcaaacagtc acagttagct cttagttccc   1800
attcacacat gttagagaag attaagctat ctttcggatt tcagaaagct tccttcaaag   1860
gagagaaatt caagactcgc atgcaggaga caagagacgc agaaatcctt aggacgctaa   1920
tagattttct tgttagtgct gtgatagtta tgtcagcgtg ctttggatat ggaacttata   1980
tttattcgta tcaaaggata acggatgtta cgtcagcttg ttctgccaca tcaaaggtat   2040
gtttatgtag tacatctgtt atcactgagt agttttcact tatcgtgtct ctttagtaat   2100
cggaagctgt tttttttccca ccctgtctct ttcagggatc taagtcatgg tggatgccaa   2160
attcagtgtc gaacttcagt tctgggtttc tttttctcag gtgtcatgta attgccgtaa   2220
cacgtatgtg ctttggcata ctaatgatcc tggcaattgc ttggttagca tttcagcgtt   2280
cctcaactac tgggtcaaat atgcctataa cattcaatct cattttgctg ggaattatct   2340
gcggctttgc tggaaggttt tgtaccaata cactaggtgg cgatggaaac acttggctca   2400
tgtactggga ggttctttgt tctatccact tacttggaaa tctttttcca tctcttttat   2460
accacgttct acatggacct atttcagtat ctcacagaga gcaagttgtc tggttaccat   2520
actgggttcg ccggtgcttg ttttatgctg cggtggggct tattcttcca gccttgactg   2580
gcttgctccc gtttgcctct ctttctgact ggaaggatca ttttgtggaa gagataaaat   2640
ccattgttat cggtgacaag attgaagcat gaaatttctt ggatgtaagg tggcg        2695
```

<210> SEQ ID NO 20
<211> LENGTH: 1551
<212> TYPE: DNA
<213> ORGANISM: Oryza sativa

<400> SEQUENCE: 20

```
atggacgccg cggcggcgtc ctcctcctcc tcctcgtcgg cgacgatggc ggcggcggcg     60
gcgtcggccg cggaggcgtc gttgtccggc tcgcctgctt cttcgaggaa cgctcgccat    120
cggcagcgta agggggtccg gctccggatg ctgcgacggc gggggcggca gcctgtggag    180
gccgagcgcg ccccgggcga tgggggcggt ggcgccgtgc aggaggatct cgcgctgcct    240
ctcggaatgt ccttcgccgc cgtcctcgcg caggttataa atacaaagaa tatttcagga    300
caaagattac atcctgattt cctctccaag atctgtacat cagcagtcaa ggaatctctg    360
acaaatatat atggtgacag ttccaacagt ttcatcaaaa atttcgaaaa atctttcagc    420
agcactttta ggacgcttca tcttgttaat gaaatacctg tgaatgagag aagtcatatt    480
cctgaatgtt cttttaaaca tgatgattct gtggctgtgg acagcttgag ctcatctgat    540
ttgcaaaatc agacaaacag aatagagcat gaccttgtga acacagtgga aagtcaacta    600
gttctctttg ccagtgacaa tcagcagtta acgcatcttc ggcatagcag atcctctcct    660
```

```
gaagctgata atcgcattct taatgccatt gatcgctcga acgaactcaa ggaatttgaa    720

atagggctta ccatgagaaa gttgcaactc aaacagtcac agttagctct tagttcccat    780

tcacacatgt tagagaagat taagctatct ttcggatttc agaaagcttc cttcaaagga    840

gagaaattca agactcgcat gcaggagaca agagacgcag aaatccttag gacgctaata    900

gattttcttg ttagtgctgt gatagttatg tcagcgtgct ttggatatgg aacttatatt    960

tattcgtatc aaaggataac ggatgttacg tcagcttgtt ctgccacatc aaagggatct   1020

aagtcatggt ggatgccaaa ttcagtgtcg aacttcagtt ctgggtttct ttttctcagg   1080

tgtcatgtaa ttgccgtaac acgtatgtgc tttggcatac taatgatcct ggcaattgct   1140

tggttagcat ttcagcgttc ctcaactact gggtcaaata tgcctataac attcaatctc   1200

attttgctgg gaattatctg cggctttgct ggaaggtttt gtaccaatac actaggtggc   1260

gatggaaaca cttggctcat gtactgggag gttctttgtt ctatccactt acttggaaat   1320

ctttttccat ctcttttata ccacgttcta catggaccta tttcagtatc tcacagagag   1380

caagttgtct ggttaccata ctgggttcgc cggtgcttgt tttatgctgc ggtggggctt   1440

attcttccag ccttgactgg cttgctcccg tttgcctctc tttctgactg gaaggatcat   1500

tttgtggaag agataaaatc cattgttatc ggtgacaaga ttgaagcatg a            1551
```

```
<210> SEQ ID NO 21
<211> LENGTH: 516
<212> TYPE: PRT
<213> ORGANISM: Oryza sativa

<400> SEQUENCE: 21

Met Asp Ala Ala Ala Ala Ser Ser Ser Ser Ser Ser Ser Ala Thr Met
1               5                   10                  15

Ala Ala Ala Ala Ala Ser Ala Ala Glu Ala Ser Leu Ser Gly Ser Pro
            20                  25                  30

Ala Ser Ser Arg Asn Ala Arg His Arg Gln Arg Lys Gly Val Arg Leu
        35                  40                  45

Arg Met Leu Arg Arg Arg Gly Arg Gln Pro Val Glu Ala Glu Arg Ala
    50                  55                  60

Pro Gly Asp Gly Gly Gly Gly Ala Val Gln Glu Asp Leu Ala Leu Pro
65                  70                  75                  80

Leu Gly Met Ser Phe Ala Ala Val Leu Ala Gln Val Ile Asn Thr Lys
                85                  90                  95

Asn Ile Ser Gly Gln Arg Leu His Pro Asp Phe Leu Ser Lys Ile Cys
            100                 105                 110

Thr Ser Ala Val Lys Glu Ser Leu Thr Asn Ile Tyr Gly Asp Ser Ser
        115                 120                 125

Asn Ser Phe Ile Lys Asn Phe Glu Lys Ser Phe Ser Ser Thr Phe Arg
    130                 135                 140

Thr Leu His Leu Val Asn Glu Ile Pro Val Asn Glu Arg Ser His Ile
145                 150                 155                 160

Pro Glu Cys Ser Phe Lys His Asp Asp Ser Val Ala Val Asp Ser Leu
                165                 170                 175

Ser Ser Ser Asp Leu Gln Asn Gln Thr Asn Arg Ile Glu His Asp Leu
            180                 185                 190

Val Asn Thr Val Glu Ser Gln Leu Val Leu Phe Ala Ser Asp Asn Gln
        195                 200                 205

Gln Leu Thr His Leu Arg His Ser Arg Ser Ser Pro Glu Ala Asp Asn
```

```
    210                 215                 220

Arg Ile Leu Asn Ala Ile Asp Arg Ser Asn Glu Leu Lys Glu Phe Glu
225                 230                 235                 240

Ile Gly Leu Thr Met Arg Lys Leu Gln Leu Lys Gln Ser Gln Leu Ala
                245                 250                 255

Leu Ser Ser His Ser His Met Leu Glu Lys Ile Lys Leu Ser Phe Gly
            260                 265                 270

Phe Gln Lys Ala Ser Phe Lys Gly Glu Lys Phe Lys Thr Arg Met Gln
        275                 280                 285

Glu Thr Arg Asp Ala Glu Ile Leu Arg Thr Leu Ile Asp Phe Leu Val
    290                 295                 300

Ser Ala Val Ile Val Met Ser Ala Cys Phe Gly Tyr Gly Thr Tyr Ile
305                 310                 315                 320

Tyr Ser Tyr Gln Arg Ile Thr Asp Val Thr Ser Ala Cys Ser Ala Thr
                325                 330                 335

Ser Lys Gly Ser Lys Ser Trp Trp Met Pro Asn Ser Val Ser Asn Phe
            340                 345                 350

Ser Ser Gly Phe Leu Phe Leu Arg Cys His Val Ile Ala Val Thr Arg
        355                 360                 365

Met Cys Phe Gly Ile Leu Met Ile Leu Ala Ile Ala Trp Leu Ala Phe
    370                 375                 380

Gln Arg Ser Ser Thr Thr Gly Ser Asn Met Pro Ile Thr Phe Asn Leu
385                 390                 395                 400

Ile Leu Leu Gly Ile Ile Cys Gly Phe Ala Gly Arg Phe Cys Thr Asn
                405                 410                 415

Thr Leu Gly Gly Asp Gly Asn Thr Trp Leu Met Tyr Trp Glu Val Leu
            420                 425                 430

Cys Ser Ile His Leu Leu Gly Asn Leu Phe Pro Ser Leu Leu Tyr His
        435                 440                 445

Val Leu His Gly Pro Ile Ser Val Ser His Arg Glu Gln Val Val Trp
    450                 455                 460

Leu Pro Tyr Trp Val Arg Arg Cys Leu Phe Tyr Ala Ala Val Gly Leu
465                 470                 475                 480

Ile Leu Pro Ala Leu Thr Gly Leu Leu Pro Phe Ala Ser Leu Ser Asp
                485                 490                 495

Trp Lys Asp His Phe Val Glu Glu Ile Lys Ser Ile Val Ile Gly Asp
            500                 505                 510

Lys Ile Glu Ala
        515


<210> SEQ ID NO 22
<211> LENGTH: 1308
<212> TYPE: DNA
<213> ORGANISM: Oryza sativa

<400> SEQUENCE: 22

caaccatgga cgacagcagc agtagcagca gcgaggttga gctgatgctc gagagggcgt      60

tcccggatgg ggtcgagata gacgtcgcca cgcactgcga cggcctcatc gccgtcacga     120

cggacgccgg cgagacattc gtctgcaacc cagccaccaa ggagctcgtc acgctgccgc     180

tcggcatcag ctgccacaac ggctgcgtcg tctgggatcg gttcgcggcc atcggctatg     240

atccgtggcg ccgcgcaacc ggtacgtcgt ctgtaggtac ttccaccggc gctacccaaa     300

cagggccggc gtcgccgaaa tcgggcatga gatcttcgtt ctcggcggcg gcggcgccgg     360
```

```
ctcatgggag gccaccgagg atccaccacc aaccagcgcc gtcgtgccca gcactccgcc    420

ggcttgcatc ggagggtgct tctactggtg caccaacgag gacgtcggca acccgagcat    480

gttgctccgg tttagccttc gcagccacaa gttcgacatg gttccatgcc atccgggctg    540

ctcatccgac gtcttcgcat tcaacaccgt gtcggagctg gacggtaagc tgttctacac    600

ccacacagcc acggagacga cgaagacgac ctcccgtctc tggatgcatg ctggacggcg    660

gcggcgacat ggcacggccg gagtggtcca tgcgctgctg catcgatgtc ggcgactacg    720

tgagctgcgt ctccccgctg gtggccggcg gggagcacat cttgctgtcg gtggatgaga    780

acttgtatct gtatggtgag aggagtaggg ttctggagaa ggtggtcgac acggcagagg    840

tggaatacgc gcggtcggat gggagcaaat ataagctagg ctatgatttg tatagtcagc    900

attactatgt tccatatgtg gagagtctag tctcaattag atttcgtaat tattaagaca    960

atcaagtcaa tgtgatggat ttatgaatca ttaggggtct gatccacagg ctcaaaaacc   1020

gccgccgctg ctccatcccc ctccggccct cttcgtccgc gctcaccccc gcttgagcag   1080

ctcgccggaa aggcgggcag cagcaagaac gactgcggcg gagctccttc tctcctcttc   1140

cacccccctga tagcactatg cgcctatgcg ggttgtggtc accgaatccc tgtcatgtgg   1200

caatggggtt ctcagatata gaccaatcta tcttctatct atcttctatt atatactaaa   1260

agtccattaa tcttcctaca aacactctca aaccgtcacg tgggattc                1308
```

<210> SEQ ID NO 23
<211> LENGTH: 759
<212> TYPE: DNA
<213> ORGANISM: Oryza sativa

<400> SEQUENCE: 23

```
atggacgaca gcagcagtag cagcagcgag gttgagctga tgctcgagag ggcgttcccg     60

gatggggtcg agatagacgt cgccacgcac tgcgacggcc tcatcgccgt cacgacggac    120

gccggcgaga cattcgtctg caacccagcc accaaggagc tcgtcacgct gccgctcggc    180

atcagctgcc acaacggctg cgtcgtctgg gatcggttcg cggccatcgg ctatgatccg    240

tggcgccgcg caaccggtac gtcgtctgcc ggcgtcgccg aaatcgggca tgagatcttc    300

gttctcggcg gcggcggcgc cggctcatgg gaggccaccg aggatccacc accaaccagc    360

gccgtcgtgc ccagcactcc gccggcttgc atcggagggt gcttctactg gtgcaccaac    420

gaggacgtcg gcaacccgag catgttgctc cggtttagcc ttcgcagcca caagttcgac    480

atggttccat gccatccggg ctgctcatcc gacgtcttcg cattcaacac cgtgtcggag    540

ctggacggct caaaaaccgc cgccgctgct ccatccccct ccggccctct tcgtccgcgc    600

tcacccccgc ttgagcagct cgccggaaag gcgggcagca gcaagaacga ctgcggcgga    660

gctccttctc tcctcttcca ccccctgata gcactatgcg cctatgcggg ttgtggtcac    720

cgaatccctg tcatgtggca atggggttct cagatatag                          759
```

<210> SEQ ID NO 24
<211> LENGTH: 252
<212> TYPE: PRT
<213> ORGANISM: Oryza sativa

<400> SEQUENCE: 24

```
Met Asp Asp Ser Ser Ser Ser Ser Ser Glu Val Glu Leu Met Leu Glu
1               5                   10                  15

Arg Ala Phe Pro Asp Gly Val Glu Ile Asp Val Ala Thr His Cys Asp
            20                  25                  30
```

```
Gly Leu Ile Ala Val Thr Thr Asp Ala Gly Glu Thr Phe Val Cys Asn
        35                  40                  45

Pro Ala Thr Lys Glu Leu Val Thr Leu Pro Leu Gly Ile Ser Cys His
    50                  55                  60

Asn Gly Cys Val Val Trp Asp Arg Phe Ala Ala Ile Gly Tyr Asp Pro
65                  70                  75                  80

Trp Arg Arg Ala Thr Gly Thr Ser Ser Ala Gly Val Ala Glu Ile Gly
                85                  90                  95

His Glu Ile Phe Val Leu Gly Gly Gly Gly Ala Gly Ser Trp Glu Ala
            100                 105                 110

Thr Glu Asp Pro Pro Pro Thr Ser Ala Val Val Pro Ser Thr Pro Pro
        115                 120                 125

Ala Cys Ile Gly Gly Cys Phe Tyr Trp Cys Thr Asn Glu Asp Val Gly
    130                 135                 140

Asn Pro Ser Met Leu Leu Arg Phe Ser Leu Arg Ser His Lys Phe Asp
145                 150                 155                 160

Met Val Pro Cys His Pro Gly Cys Ser Ser Asp Val Phe Ala Phe Asn
                165                 170                 175

Thr Val Ser Glu Leu Asp Gly Ser Lys Thr Ala Ala Ala Ala Pro Ser
            180                 185                 190

Pro Ser Gly Pro Leu Arg Pro Arg Ser Pro Pro Leu Glu Gln Leu Ala
        195                 200                 205

Gly Lys Ala Gly Ser Ser Lys Asn Asp Cys Gly Gly Ala Pro Ser Leu
    210                 215                 220

Leu Phe His Pro Leu Ile Ala Leu Cys Ala Tyr Ala Gly Cys Gly His
225                 230                 235                 240

Arg Ile Pro Val Met Trp Gln Trp Gly Ser Gln Ile
                245                 250
```

<210> SEQ ID NO 25
<211> LENGTH: 33
<212> TYPE: DNA
<213> ORGANISM: Artificial Sequence
<220> FEATURE:
<223> OTHER INFORMATION: Forward primer for cloning cDNA of OsDN-DTP8 gene

<400> SEQUENCE: 25
ctgctgaggg acgatggagc tctggtggat ttc 33

<210> SEQ ID NO 26
<211> LENGTH: 34
<212> TYPE: DNA
<213> ORGANISM: Artificial Sequence
<220> FEATURE:
<223> OTHER INFORMATION: Reverse primer for cloning cDNA of OsDN-DTP8 gene

<400> SEQUENCE: 26
ccgctgaggg tcttctaccc atcccctcaa gtcc 34

<210> SEQ ID NO 27
<211> LENGTH: 27
<212> TYPE: DNA
<213> ORGANISM: Artificial Sequence
<220> FEATURE:
<223> OTHER INFORMATION: Forward primer for cloning cDNA of OsKIK1 gene

<400> SEQUENCE: 27
cgcacacgtg aatacatata ttttctc 27

<210> SEQ ID NO 28
<211> LENGTH: 24
<212> TYPE: DNA
<213> ORGANISM: Artificial Sequence
<220> FEATURE:
<223> OTHER INFORMATION: Reverse primer for cloning cDNA of OsKIK1 gene

<400> SEQUENCE: 28
gcgtgtttct tcgtgtctat gtac 24

<210> SEQ ID NO 29
<211> LENGTH: 23
<212> TYPE: DNA
<213> ORGANISM: Artificial Sequence
<220> FEATURE:
<223> OTHER INFORMATION: Forward primer for cloning cDNA of OsRWDD1 gene

<400> SEQUENCE: 29
ctcgtcgcgg ccgtggaaat tac 23

<210> SEQ ID NO 30
<211> LENGTH: 24
<212> TYPE: DNA
<213> ORGANISM: Artificial Sequence
<220> FEATURE:
<223> OTHER INFORMATION: Reverse primer for cloning cDNA of OsRWDD1 gene

<400> SEQUENCE: 30
gtcttggaca cggccatctt gcac 24

<210> SEQ ID NO 31
<211> LENGTH: 24
<212> TYPE: DNA
<213> ORGANISM: Artificial Sequence
<220> FEATURE:
<223> OTHER INFORMATION: Forward primer for cloning gDNA of OsUFD1 gene

<400> SEQUENCE: 31
gatcaatctc tcgcttcctt cccg 24

<210> SEQ ID NO 32
<211> LENGTH: 24
<212> TYPE: DNA
<213> ORGANISM: Artificial Sequence
<220> FEATURE:
<223> OTHER INFORMATION: Reverse primer for cloning gDNA of OsUFD1 gene

<400> SEQUENCE: 32
gcacaggacc aaacgattca caag 24

<210> SEQ ID NO 33
<211> LENGTH: 26
<212> TYPE: DNA
<213> ORGANISM: Artificial Sequence
<220> FEATURE:
<223> OTHER INFORMATION: Forward primer for cloning gDNA of OsPPR2 gene

<400> SEQUENCE: 33
gtcgaaaccg agttgatctc gctatg 26

<210> SEQ ID NO 34
<211> LENGTH: 25
<212> TYPE: DNA
<213> ORGANISM: Artificial Sequence
<220> FEATURE:
<223> OTHER INFORMATION: Reverse primer for cloning gDNA of OsPPR2 gene

<400> SEQUENCE: 34
ggctctacgg aatccaataa agaag 25

<210> SEQ ID NO 35
<211> LENGTH: 23
<212> TYPE: DNA
<213> ORGANISM: Artificial Sequence
<220> FEATURE:
<223> OTHER INFORMATION: Forward primer for cloning cDNA of OsSAUR28-1 gene

<400> SEQUENCE: 35
cgatgatggt gatgggctac ttg 23

<210> SEQ ID NO 36
<211> LENGTH: 21
<212> TYPE: DNA
<213> ORGANISM: Artificial Sequence
<220> FEATURE:
<223> OTHER INFORMATION: Reverse primer for cloning cDNA of OsSAUR28-1 gene

<400> SEQUENCE: 36
gtacgcgtgg ctagctgatg g 21

<210> SEQ ID NO 37
<211> LENGTH: 25
<212> TYPE: DNA
<213> ORGANISM: Artificial Sequence
<220> FEATURE:
<223> OTHER INFORMATION: Forward primer for cloning gDNA of OsHYS1 gene

<400> SEQUENCE: 37
caaatctcac gcggcgcttt ctctc 25

<210> SEQ ID NO 38
<211> LENGTH: 28
<212> TYPE: DNA
<213> ORGANISM: Artificial Sequence
<220> FEATURE:
<223> OTHER INFORMATION: Reverse primer for cloning gDNA of OsHYS1 gene

<400> SEQUENCE: 38
cgccacctta catccaagaa atttcatg 28

<210> SEQ ID NO 39
<211> LENGTH: 25
<212> TYPE: DNA
<213> ORGANISM: Artificial Sequence
<220> FEATURE:
<223> OTHER INFORMATION: Forward primer for cloning gDNA of OsFBID1 gene

<400> SEQUENCE: 39
caaccatgga cgacagcagc agtag 25

<210> SEQ ID NO 40
<211> LENGTH: 26
<212> TYPE: DNA
<213> ORGANISM: Artificial Sequence
<220> FEATURE:
<223> OTHER INFORMATION: Reverse primer for cloning gDNA of OsFBID1 gene

<400> SEQUENCE: 40
gaatcccacg tgacggtttg agagtg 26

<210> SEQ ID NO 41
<211> LENGTH: 19
<212> TYPE: DNA
<213> ORGANISM: Artificial Sequence
<220> FEATURE:
<223> OTHER INFORMATION: Forward primer for real-time PCR analysis of OsDN-DTP8 gene

<400> SEQUENCE: 41
ccctctcctt cttgcgaac 19

<210> SEQ ID NO 42
<211> LENGTH: 19
<212> TYPE: DNA
<213> ORGANISM: Artificial Sequence
<220> FEATURE:
<223> OTHER INFORMATION: Reverse primer for real-time PCR analysis of OsDN-DTP8 gene

<400> SEQUENCE: 42
tcctcgccat gaaccattg 19

<210> SEQ ID NO 43
<211> LENGTH: 20
<212> TYPE: DNA
<213> ORGANISM: Artificial Sequence
<220> FEATURE:
<223> OTHER INFORMATION: Forward primer for real-time PCR analysis of OsRWDD1 gene

<400> SEQUENCE: 43
acttcataca gctcccatgc 20

<210> SEQ ID NO 44
<211> LENGTH: 18
<212> TYPE: DNA
<213> ORGANISM: Artificial Sequence
<220> FEATURE:
<223> OTHER INFORMATION: Reverse primer for real-time PCR analysis of OsRWDD1 gene

<400> SEQUENCE: 44
ttcacgtgga tcctgcac 18

<210> SEQ ID NO 45
<211> LENGTH: 23
<212> TYPE: DNA
<213> ORGANISM: Artificial Sequence
<220> FEATURE:
<223> OTHER INFORMATION: Forward primer for real-time PCR analysis of OsUFD1 gene

<400> SEQUENCE: 45
tcaagagatc aacccaactg aag 23

<210> SEQ ID NO 46
<211> LENGTH: 22
<212> TYPE: DNA
<213> ORGANISM: Artificial Sequence
<220> FEATURE:
<223> OTHER INFORMATION: Reverse primer for real-time PCR analysis of OsUFD1 gene

<400> SEQUENCE: 46
ccatcaaaca ggaaggcaat ag 22

<210> SEQ ID NO 47
<211> LENGTH: 21
<212> TYPE: DNA
<213> ORGANISM: Artificial Sequence
<220> FEATURE:
<223> OTHER INFORMATION: Forward primer for real-time PCR analysis of OsSAUR28-1 gene

<400> SEQUENCE: 47
atgatggtga tgggctactt g 21

<210> SEQ ID NO 48
<211> LENGTH: 19
<212> TYPE: DNA
<213> ORGANISM: Artificial Sequence
<220> FEATURE:
<223> OTHER INFORMATION: Reverse primer for real-time PCR analysis of OsSAUR28-1 gene

<400> SEQUENCE: 48
cggagtccat cgtcgttat 19

<210> SEQ ID NO 49
<211> LENGTH: 21
<212> TYPE: DNA
<213> ORGANISM: Artificial Sequence
<220> FEATURE:
<223> OTHER INFORMATION: Forward primer for real-time PCR analysis of OsHYS1 gene

<400> SEQUENCE: 49
agagcaagtt gtctggttac c 21

<210> SEQ ID NO 50
<211> LENGTH: 20
<212> TYPE: DNA
<213> ORGANISM: Artificial Sequence
<220> FEATURE:
<223> OTHER INFORMATION: Reverse primer for real-time PCR analysis of OsHYS1 gene

<400> SEQUENCE: 50
tcagaaagag aggcaaacgg 20

<210> SEQ ID NO 51
<211> LENGTH: 264
<212> TYPE: DNA
<213> ORGANISM: Oryza sativa

<400> SEQUENCE: 51
atggagctct ggtggatttc ggcttcgggg agatggctgc cgagctccct ctccttcttg 60
cgaacccaac ggcggcagcg gcgaccaaat gcggcggcta aggcggctgc tagctgcggc 120
tggagatcgg aacatgacgg caacccaatg gttcatggcg aggacggctt ccggcgaagt 180
ttcggcgcaa ggggaacggc ggccggggtg gacctcgacc ttgcggagcc gatggaggtg 240
gcggcgcagg aaggaggcag atga 264

<210> SEQ ID NO 52
<211> LENGTH: 87
<212> TYPE: PRT
<213> ORGANISM: Oryza sativa

<400> SEQUENCE: 52

```
Met Glu Leu Trp Trp Ile Ser Ala Ser Gly Arg Trp Leu Pro Ser Ser
1               5                   10                  15

Leu Ser Phe Leu Arg Thr Gln Arg Arg Gln Arg Arg Pro Asn Ala Ala
            20                  25                  30

Ala Lys Ala Ala Ala Ser Cys Gly Trp Arg Ser Glu His Asp Gly Asn
        35                  40                  45

Pro Met Val His Gly Glu Asp Gly Phe Arg Arg Ser Phe Gly Ala Arg
    50                  55                  60

Gly Thr Ala Ala Gly Val Asp Leu Asp Leu Ala Glu Pro Met Glu Val
65                  70                  75                  80

Ala Ala Gln Glu Gly Gly Arg
                85
```

<210> SEQ ID NO 53
<211> LENGTH: 2562
<212> TYPE: DNA
<213> ORGANISM: Oryza sativa

<400> SEQUENCE: 53

```
atggcggctt ctcctcctcc tcctcctcgt cccctgctgc tgcttctccc gttgctgctc     60
gtttggggcg tggtggttgc ggcggcggcg gcgacggata cgttgaggca gggggagtcg    120
ctgacggggg cggcgacgct ggtgtcgtcg ccgtcggggg tgttcgaggt ggggttcttc    180
gcgccggacc cgaagctgcc gtcgcggctc tacctcggca tctggtaccg cagcatctcg    240
ccgagaaccg tcgtctgggt cgccaaccgc gccgcgccgg ccaccgcgcc gtcgccgtcg    300
ctcacgctcg cggccaacgg cgagctccgc gtgctcgacg gctccgccgc ggacgcggac    360
gcgccgctct tgtggaggtc gaacgcgtcc acgcagtccg cgccacgcgg cgggtacaag    420
gccgtcatcc aggacaccgg cagcctcgag gtgcgcagcg acgacggcac gctgtgggac    480
agcttctggc acccgtcgga caccatgctg tccgggatgc gcatcaccgt gcgcacgccc    540
gggaggggcc cctccgagcc gatgcgcttc acgtcgtgga ccagcgagac ggacccctcg    600
ccggggcggt acgcgctcgg cctcgacccg gccaactccg gccaggccta catctggaga    660
gatggcaatg tcaccatttg gaggtcagga caatggactg ggcagaattt tgtgggcatt    720
ccttggagac cactgtactt gtatgggttc aagccagcaa atgatgcaaa cttaggtgca    780
tactacactt acactgcatc aaacacatct ctgcaaaggt ttgttgttat gccaaatggt    840
acagacatct gttacatggt taagaagtca gcacaagagt gggagactgt ctggatgcaa    900
ccatcaaatg agtgtgagta ctatgctacg tgtggcgcaa atgctaaatg cactgccatg    960
caagatggca aggcaaaatg tacctgccta aaaggatttc agccaaagtt gcttgatcag   1020
tggaatatgg gaaattggag tcaaggttgt gtcaggagcc cacctttggg ttgtcaggtg   1080
aaccaaactg ggatggattt tctttctatc ccaaacatca agtggccgga tttctcatac   1140
tggccatcta cggtgcaaga tgagaatgga tgcatgaatg cttgcctcag caactgctca   1200
tgtggtgcct atgtctacat gactacaata ggatgtctac tgtggggtag cgacctgatc   1260
gacatgtacc agtttcagag tgggggatat accctaaacc tcaaacttcc tgcttctgag   1320
ttacgctcac atcatgcagt ttggaaaata gccacaatag tgtctgcagt ggtgctattt   1380
gttttgctag cttgcctctt cctgtggtgg aagcgtggga ggaatatcaa agatgtgatg   1440
cacaaaagtt ggaggtcaat gcatacgtct acacgatctc agcagaatag tggtatgctg   1500
gacatctcgc agtcgattcc ttttgaagac gacacagagg atggaaaaag tcatgaactc   1560
aaagtatact cctttgaccg gataaaagct gccacttgta atttcagtga ctccaacaag   1620
```

```
cttggagcag gaggatttgg tcctgtatat atgggaaaat tacctggggg agaagaagta   1680

gccgttaaga ggctttgtag gaaatcaggt caaggccttg aggagttcaa gaatgaggtc   1740

atacttatcg caaaactgca gcatcgcaat cttgtgagac tattaggatg ctgcatacag   1800

ggagaagaga agatcttggt gtacgagtac atgcctaaca aaagtctaga tgcattcctc   1860

ttcaatcctg agaagcaagg gctcctagac tggaggaaac ggtttgatat aattgaaggg   1920

attgctcgag ggctgttata tctccaccgg gactcaaggt tgcgagttgt tcatcgtgat   1980

ctcaaggcca gcaacattct cctggacaaa gacatgaacc ccaagatttc agattttgga   2040

atggccagga tgtttggagg ggatcaaaac caattcaaca cgaatcgtgt ggttggaaca   2100

tttggctata tgtcgccgga atatgctatg gaaggcattt tctcagtaaa gtccgatatt   2160

tatagctttg gagttctaat gttggagatc atcacaggaa agagggcttt gagctttcat   2220

ggtcaacaag actccctaaa cattgcagga tttgcatggc gacaatggaa tgaagacaag   2280

ggcgaggaac tgattgatcc attgataaga gcatcgtgct cacttcgaca agtcttgaga   2340

tgcatccaca ttgcattgct atgtgttcaa gatcatgcgc aagaacgtcc tgatatccct   2400

gcggtcatac tgatgttgag cagcgacagc tccagccttc ccatgccaag accgcctacc   2460

ctgatgctcc atggtcgttc ggctgagacg agcaaatcaa gtgagaagga tcagagccac   2520

tccatcggta ctgtgtcaat gacacaattg catggaagat ag                      2562
```

<210> SEQ ID NO 54
<211> LENGTH: 853
<212> TYPE: PRT
<213> ORGANISM: Oryza sativa

<400> SEQUENCE: 54

```
Met Ala Ala Ser Pro Pro Pro Pro Pro Arg Pro Leu Leu Leu Leu Leu
1               5                   10                  15

Pro Leu Leu Leu Val Trp Gly Val Val Val Ala Ala Ala Ala Ala Thr
            20                  25                  30

Asp Thr Leu Arg Gln Gly Glu Ser Leu Thr Gly Ala Ala Thr Leu Val
        35                  40                  45

Ser Ser Pro Ser Gly Val Phe Glu Val Gly Phe Phe Ala Pro Asp Pro
    50                  55                  60

Lys Leu Pro Ser Arg Leu Tyr Leu Gly Ile Trp Tyr Arg Ser Ile Ser
65                  70                  75                  80

Pro Arg Thr Val Val Trp Val Ala Asn Arg Ala Ala Pro Ala Thr Ala
                85                  90                  95

Pro Ser Pro Ser Leu Thr Leu Ala Ala Asn Gly Glu Leu Arg Val Leu
            100                 105                 110

Asp Gly Ser Ala Ala Asp Ala Asp Ala Pro Leu Leu Trp Arg Ser Asn
        115                 120                 125

Ala Ser Thr Gln Ser Ala Pro Arg Gly Gly Tyr Lys Ala Val Ile Gln
    130                 135                 140

Asp Thr Gly Ser Leu Glu Val Arg Ser Asp Asp Gly Thr Leu Trp Asp
145                 150                 155                 160

Ser Phe Trp His Pro Ser Asp Thr Met Leu Ser Gly Met Arg Ile Thr
                165                 170                 175

Val Arg Thr Pro Gly Arg Gly Pro Ser Glu Pro Met Arg Phe Thr Ser
            180                 185                 190

Trp Thr Ser Glu Thr Asp Pro Ser Pro Gly Arg Tyr Ala Leu Gly Leu
        195                 200                 205
```

```
Asp Pro Ala Asn Ser Gly Gln Ala Tyr Ile Trp Arg Asp Gly Asn Val
    210                 215                 220

Thr Ile Trp Arg Ser Gly Gln Trp Thr Gly Gln Asn Phe Val Gly Ile
225                 230                 235                 240

Pro Trp Arg Pro Leu Tyr Leu Tyr Gly Phe Lys Pro Ala Asn Asp Ala
                245                 250                 255

Asn Leu Gly Ala Tyr Tyr Thr Tyr Thr Ala Ser Asn Thr Ser Leu Gln
            260                 265                 270

Arg Phe Val Val Met Pro Asn Gly Thr Asp Ile Cys Tyr Met Val Lys
        275                 280                 285

Lys Ser Ala Gln Glu Trp Glu Thr Val Trp Met Gln Pro Ser Asn Glu
    290                 295                 300

Cys Glu Tyr Tyr Ala Thr Cys Gly Ala Asn Ala Lys Cys Thr Ala Met
305                 310                 315                 320

Gln Asp Gly Lys Ala Lys Cys Thr Cys Leu Lys Gly Phe Gln Pro Lys
                325                 330                 335

Leu Leu Asp Gln Trp Asn Met Gly Asn Trp Ser Gln Gly Cys Val Arg
            340                 345                 350

Ser Pro Pro Leu Gly Cys Gln Val Asn Gln Thr Gly Asp Gly Phe Leu
        355                 360                 365

Ser Ile Pro Asn Ile Lys Trp Pro Asp Phe Ser Tyr Trp Pro Ser Thr
    370                 375                 380

Val Gln Asp Glu Asn Gly Cys Met Asn Ala Cys Leu Ser Asn Cys Ser
385                 390                 395                 400

Cys Gly Ala Tyr Val Tyr Met Thr Thr Ile Gly Cys Leu Leu Trp Gly
                405                 410                 415

Ser Asp Leu Ile Asp Met Tyr Gln Phe Gln Ser Gly Gly Tyr Thr Leu
            420                 425                 430

Asn Leu Lys Leu Pro Ala Ser Glu Leu Arg Ser His His Ala Val Trp
        435                 440                 445

Lys Ile Ala Thr Ile Val Ser Ala Val Val Leu Phe Val Leu Leu Ala
    450                 455                 460

Cys Leu Phe Leu Trp Trp Lys Arg Gly Arg Asn Ile Lys Asp Val Met
465                 470                 475                 480

His Lys Ser Trp Arg Ser Met His Thr Ser Thr Arg Ser Gln Gln Asn
                485                 490                 495

Ser Gly Met Leu Asp Ile Ser Gln Ser Ile Pro Phe Glu Asp Asp Thr
            500                 505                 510

Glu Asp Gly Lys Ser His Glu Leu Lys Val Tyr Ser Phe Asp Arg Ile
        515                 520                 525

Lys Ala Ala Thr Cys Asn Phe Ser Asp Ser Asn Lys Leu Gly Ala Gly
    530                 535                 540

Gly Phe Gly Pro Val Tyr Met Gly Lys Leu Pro Gly Gly Glu Glu Val
545                 550                 555                 560

Ala Val Lys Arg Leu Cys Arg Lys Ser Gly Gln Gly Leu Glu Glu Phe
                565                 570                 575

Lys Asn Glu Val Ile Leu Ile Ala Lys Leu Gln His Arg Asn Leu Val
            580                 585                 590

Arg Leu Leu Gly Cys Cys Ile Gln Gly Glu Glu Lys Ile Leu Val Tyr
        595                 600                 605

Glu Tyr Met Pro Asn Lys Ser Leu Asp Ala Phe Leu Phe Asn Pro Glu
    610                 615                 620
```

```
Lys Gln Gly Leu Leu Asp Trp Arg Lys Arg Phe Asp Ile Ile Glu Gly
625                 630                 635                 640

Ile Ala Arg Gly Leu Leu Tyr Leu His Arg Asp Ser Arg Leu Arg Val
                645                 650                 655

Val His Arg Asp Leu Lys Ala Ser Asn Ile Leu Leu Asp Lys Asp Met
            660                 665                 670

Asn Pro Lys Ile Ser Asp Phe Gly Met Ala Arg Met Phe Gly Gly Asp
        675                 680                 685

Gln Asn Gln Phe Asn Thr Asn Arg Val Val Gly Thr Phe Gly Tyr Met
    690                 695                 700

Ser Pro Glu Tyr Ala Met Glu Gly Ile Phe Ser Val Lys Ser Asp Ile
705                 710                 715                 720

Tyr Ser Phe Gly Val Leu Met Leu Glu Ile Ile Thr Gly Lys Arg Ala
                725                 730                 735

Leu Ser Phe His Gly Gln Gln Asp Ser Leu Asn Ile Ala Gly Phe Ala
            740                 745                 750

Trp Arg Gln Trp Asn Glu Asp Lys Gly Glu Glu Leu Ile Asp Pro Leu
        755                 760                 765

Ile Arg Ala Ser Cys Ser Leu Arg Gln Val Leu Arg Cys Ile His Ile
    770                 775                 780

Ala Leu Leu Cys Val Gln Asp His Ala Gln Glu Arg Pro Asp Ile Pro
785                 790                 795                 800

Ala Val Ile Leu Met Leu Ser Ser Asp Ser Ser Ser Leu Pro Met Pro
                805                 810                 815

Arg Pro Pro Thr Leu Met Leu His Gly Arg Ser Ala Glu Thr Ser Lys
            820                 825                 830

Ser Ser Glu Lys Asp Gln Ser His Ser Ile Gly Thr Val Ser Met Thr
        835                 840                 845

Gln Leu His Gly Arg
    850
```

```
<210> SEQ ID NO 55
<211> LENGTH: 2649
<212> TYPE: DNA
<213> ORGANISM: Zea mays

<400> SEQUENCE: 55

atggcccacg ccgccgcggc agcgctcgcc cttctcgtct tcttctgcgc gcaagcgcgg      60

gacgcggccg tccatgtcgt cgacgcggcg gcgacgctgt cgcaggggca gtcgctgggc     120

gccaccgaca agctggtgtc ggccggcggc accttcgagc tggccttctt cacgccgacg     180

gggggcgacc cgtcgcggcg gtacctgggc gtcatgtacg cgcagtccac cgagcagacc     240

gtgccgtggg tggccaaccg cgacgtgccc gtgagcgcgg gctccgcgta ctcggcgacc     300

gtcacggccg ccggggagct gcaggtactg gagggcgacc gcgtggtctg gcgcaccgac     360

aactccgcga cgacgacgtc gccgggaaca gcgggaggcg aacaagcagc gaacgtgacg     420

ctcaccgtgc tcgacaccgg gaacctccag ctggccgcgg gcgacggggg ccccgtcatc     480

tggcagagct tcgaccaccc cgcggacacc ttcctccccg ggatgagcat caccctggac     540

cggcgcggcg gcggggccgt ccgccggacg ctgttcacgt cgtggcggag ccccgcggac     600

cccggcaccg ggacttcac gctggggcag gacccgctcg gctccgcgca gctctacatc      660

tggcagacga ccggcggcca gaacaccacc tactggcggt ccgggcagtg ggccaacacc     720

aacttcgtcg gcgtgccctg gcgctcgctc tacgtgtacg gcttcaagct caacggcgac     780
```

```
cccaacaacg gctccggggt catgtcctac gtcttcaaca cgtacaacag ctccgagtac    840

cggttcatgc tccactccaa cggcaccgag acgtgctaca tgctcctcgc caccggcgac    900

tgggagaccg tctggtcgca gccgaccatc ccgtgccagg cctacaacat gtgcggcgcc    960

aacgcccagt gcgccgccgc cgccgacggc ggccaggcag tctgcacctg cctgacaggt   1020

ttcgagccga ggaacgtatc ggagtacagc aacgggaact ggacgcaggg gtgcgtcagg   1080

agctccccgc tgccctgcgg cggcgagccg aacgtgagcg gcgctggcgc cggcgccggc   1140

gtaggcgttg gcttcgccga cctcccgggc gtgaagctgc ccaacttcgc ggcctgggga   1200

tccactgtgg gcgacgcggc cgcgtgcgag cagtcgtgcc tgggcaactg ctcgtgcggc   1260

gcgtacagct acagcactgg caccggctgc ctcacctggg gccaggacct gctggacatc   1320

taccgcttcc cggatggaga aggatacgat ctgcagatca aggtccccgc gtacttactt   1380

gagacgggct ccaaaaggag gcgatggacg acagttgtcg tcgccgtagt cgtcgccgtg   1440

gctgtattgg caggatgcgg ccttctcctg tggaaatgca ggagaaggat caaagagaaa   1500

cttggcatcg ttgttggcag tgaggagacg aaggcgacgc agccgtctct gcttcctttg   1560

agggaagcaa ggcaggattt ctcagggccg aagcagactg atcaagagga agcagagggc   1620

ggcaagaagt tcgagctgcc tatcttctcc ttggagacgg tagcggcggc caccggcgac   1680

ttcagtgccg acaacaagct tggggaggga ggctttggcc atgtctacaa gggaagactt   1740

cccggggccg aagaggttgc ggtgaagagg ctgtcccggg gctcagtgca ggggatggag   1800

gagtttaaga acgaggtcat cctgatcgcc aagctgcagc accgcaacct tgtcaagttg   1860

ttaggctgct gcatccaggg ggaggagaag atcttggtgt acgagtacat gcccaacaag   1920

agcctggacg gcttcctttt cgatccggcg cggcgaggcc tgctggactg gaagacgagg   1980

ttccacatca tcgagggcat cgcccgaggg ctcctgtacc tccacaggga ctcgcgtctc   2040

cgcgtggtgc accgcgacct caaggccagc aacatcctgc tagaccacga catgatcccc   2100

aagatctccg acttcggcat ggcgcgcatc ttcggcggcg accagaacca ggtgaacacg   2160

aaccgcgtcg tgggcacgct ggggtacatg tcacccgagt acgccatgga gggcctcttc   2220

tccgtgcgct ccgacgtgta cagcttcggc atcctcatcc tggagatcgt ctccgggcag   2280

aagaacagca gcttccacca catggagggc tccctcaaca tcgtcggcta cgcgtggcag   2340

ctgtggaacg ccgacagggg ggagcgcctg atcgacccgg ccatcctgcc ggcgtgctcc   2400

gtgcgggagg cgctgcgctg cgtgcacatg gcgctgctgt gcgtgcagga ccacgcgtgc   2460

gaccgcccgg acatccccta cgtcgtcatg gcgctcggca gcgacagctc cgtgctgccg   2520

atgcccaagc cgcccacgtt cacgctgcag tgcacgtcgt cgtcggacag ggacgggatc   2580

ttcccggaca aggtcgacga gtcctactcc gcctgcgatc tcaccgttac catgctgcat   2640

gggaggtag                                                           2649
```

<210> SEQ ID NO 56
<211> LENGTH: 882
<212> TYPE: PRT
<213> ORGANISM: Zea mays

<400> SEQUENCE: 56

```
Met Ala His Ala Ala Ala Ala Ala Leu Ala Leu Leu Val Phe Phe Cys
1               5                   10                  15

Ala Gln Ala Arg Asp Ala Ala Val His Val Val Asp Ala Ala Ala Thr
            20                  25                  30

Leu Ser Gln Gly Gln Ser Leu Gly Ala Thr Asp Lys Leu Val Ser Ala
```

-continued

```
        35                  40                  45

Gly Gly Thr Phe Glu Leu Ala Phe Phe Thr Pro Thr Gly Gly Asp Pro
    50                  55                  60

Ser Arg Arg Tyr Leu Gly Val Met Tyr Ala Gln Ser Thr Glu Gln Thr
65                  70                  75                  80

Val Pro Trp Val Ala Asn Arg Asp Val Pro Val Ser Ala Gly Ser Ala
                85                  90                  95

Tyr Ser Ala Thr Val Thr Ala Ala Gly Glu Leu Gln Val Leu Glu Gly
            100                 105                 110

Asp Arg Val Val Trp Arg Thr Asp Asn Ser Ala Thr Thr Thr Ser Pro
        115                 120                 125

Gly Thr Ala Gly Gly Glu Gln Ala Ala Asn Val Thr Leu Thr Val Leu
    130                 135                 140

Asp Thr Gly Asn Leu Gln Leu Ala Ala Gly Asp Gly Gly Pro Val Ile
145                 150                 155                 160

Trp Gln Ser Phe Asp His Pro Ala Asp Thr Phe Leu Pro Gly Met Ser
                165                 170                 175

Ile Thr Leu Asp Arg Arg Gly Gly Gly Ala Val Arg Arg Thr Leu Phe
            180                 185                 190

Thr Ser Trp Arg Ser Pro Ala Asp Pro Gly Thr Gly Asp Phe Thr Leu
        195                 200                 205

Gly Gln Asp Pro Leu Gly Ser Ala Gln Leu Tyr Ile Trp Gln Thr Thr
    210                 215                 220

Gly Gly Gln Asn Thr Thr Tyr Trp Arg Ser Gly Gln Trp Ala Asn Thr
225                 230                 235                 240

Asn Phe Val Gly Val Pro Trp Arg Ser Leu Tyr Val Tyr Gly Phe Lys
                245                 250                 255

Leu Asn Gly Asp Pro Asn Asn Gly Ser Gly Val Met Ser Tyr Val Phe
            260                 265                 270

Asn Thr Tyr Asn Ser Ser Glu Tyr Arg Phe Met Leu His Ser Asn Gly
        275                 280                 285

Thr Glu Thr Cys Tyr Met Leu Leu Ala Thr Gly Asp Trp Glu Thr Val
    290                 295                 300

Trp Ser Gln Pro Thr Ile Pro Cys Gln Ala Tyr Asn Met Cys Gly Ala
305                 310                 315                 320

Asn Ala Gln Cys Ala Ala Ala Ala Asp Gly Gly Gln Ala Val Cys Thr
                325                 330                 335

Cys Leu Thr Gly Phe Glu Pro Arg Asn Val Ser Glu Tyr Ser Asn Gly
            340                 345                 350

Asn Trp Thr Gln Gly Cys Val Arg Ser Ser Pro Leu Pro Cys Gly Gly
        355                 360                 365

Glu Pro Asn Val Ser Gly Ala Gly Ala Gly Ala Gly Val Gly Val Gly
    370                 375                 380

Phe Ala Asp Leu Pro Gly Val Lys Leu Pro Asn Phe Ala Ala Trp Gly
385                 390                 395                 400

Ser Thr Val Gly Asp Ala Ala Ala Cys Glu Gln Ser Cys Leu Gly Asn
                405                 410                 415

Cys Ser Cys Gly Ala Tyr Ser Tyr Ser Thr Gly Thr Gly Cys Leu Thr
            420                 425                 430

Trp Gly Gln Asp Leu Leu Asp Ile Tyr Arg Phe Pro Asp Gly Glu Gly
        435                 440                 445

Tyr Asp Leu Gln Ile Lys Val Pro Ala Tyr Leu Leu Glu Thr Gly Ser
    450                 455                 460
```

```
Lys Arg Arg Arg Trp Thr Thr Val Val Val Ala Val Val Val Ala Val
465                 470                 475                 480

Ala Val Leu Ala Gly Cys Gly Leu Leu Leu Trp Lys Cys Arg Arg Arg
                485                 490                 495

Ile Lys Glu Lys Leu Gly Ile Val Val Gly Ser Glu Glu Thr Lys Ala
            500                 505                 510

Thr Gln Pro Ser Leu Leu Pro Leu Arg Glu Ala Arg Gln Asp Phe Ser
        515                 520                 525

Gly Pro Lys Gln Thr Asp Gln Glu Glu Ala Glu Gly Gly Lys Lys Phe
    530                 535                 540

Glu Leu Pro Ile Phe Ser Leu Glu Thr Val Ala Ala Ala Thr Gly Asp
545                 550                 555                 560

Phe Ser Ala Asp Asn Lys Leu Gly Glu Gly Gly Phe Gly His Val Tyr
                565                 570                 575

Lys Gly Arg Leu Pro Gly Ala Glu Glu Val Ala Val Lys Arg Leu Ser
            580                 585                 590

Arg Gly Ser Val Gln Gly Met Glu Glu Phe Lys Asn Glu Val Ile Leu
        595                 600                 605

Ile Ala Lys Leu Gln His Arg Asn Leu Val Lys Leu Leu Gly Cys Cys
    610                 615                 620

Ile Gln Gly Glu Glu Lys Ile Leu Val Tyr Glu Tyr Met Pro Asn Lys
625                 630                 635                 640

Ser Leu Asp Gly Phe Leu Phe Asp Pro Ala Arg Arg Gly Leu Leu Asp
                645                 650                 655

Trp Lys Thr Arg Phe His Ile Ile Glu Gly Ile Ala Arg Gly Leu Leu
            660                 665                 670

Tyr Leu His Arg Asp Ser Arg Leu Arg Val Val His Arg Asp Leu Lys
        675                 680                 685

Ala Ser Asn Ile Leu Leu Asp His Asp Met Ile Pro Lys Ile Ser Asp
    690                 695                 700

Phe Gly Met Ala Arg Ile Phe Gly Gly Asp Gln Asn Gln Val Asn Thr
705                 710                 715                 720

Asn Arg Val Val Gly Thr Leu Gly Tyr Met Ser Pro Glu Tyr Ala Met
                725                 730                 735

Glu Gly Leu Phe Ser Val Arg Ser Asp Val Tyr Ser Phe Gly Ile Leu
            740                 745                 750

Ile Leu Glu Ile Val Ser Gly Gln Lys Asn Ser Ser Phe His His Met
        755                 760                 765

Glu Gly Ser Leu Asn Ile Val Gly Tyr Ala Trp Gln Leu Trp Asn Ala
    770                 775                 780

Asp Arg Gly Glu Arg Leu Ile Asp Pro Ala Ile Leu Pro Ala Cys Ser
785                 790                 795                 800

Val Arg Glu Ala Leu Arg Cys Val His Met Ala Leu Leu Cys Val Gln
                805                 810                 815

Asp His Ala Cys Asp Arg Pro Asp Ile Pro Tyr Val Val Met Ala Leu
            820                 825                 830

Gly Ser Asp Ser Ser Val Leu Pro Met Pro Lys Pro Pro Thr Phe Thr
        835                 840                 845

Leu Gln Cys Thr Ser Ser Ser Asp Arg Asp Gly Ile Phe Pro Asp Lys
    850                 855                 860

Val Asp Glu Ser Tyr Ser Ala Cys Asp Leu Thr Val Thr Met Leu His
865                 870                 875                 880
```

Gly Arg

<210> SEQ ID NO 57
<211> LENGTH: 2640
<212> TYPE: DNA
<213> ORGANISM: Sorghum bicolor

<400> SEQUENCE: 57

```
atggcccacg ccgccgtggc agcgctcgcc ctgctcgtct tcttcagcgc gcaagcgcgg     60
cgggacggcg ccggcgtata cgtcgtggac gcggcggcgg cgctgtcgca ggggcactcg    120
ctgggcgccg gcgacaagct ggtgtcgtca gacggcacct tcgagctagc cttcttcacg    180
ccgaccgggg ccgccgaccc gtcgcggcgg tacctgggcg tcatgtacgc gcagtccaac    240
gagcagaccg tgccctgggt ggccaaccgc gacgcgcccg tgagcgccgg ctcgtcgtac    300
tcggccaccg tcacggacgc cggcgagctg caggtgcttg agggcgaacg cgtggtctgg    360
cgcaccaact ccgcgacgac ggcctcctcc tcctcctcct cgccggcgaa cgtgacgctc    420
accctcctcg acaccgggaa cctccagctg accgcgggcg caacggtgct ctggcagagc    480
ttcgaccacc ccgcggacac cttcctcccc gggatgagca tcacgctcga ccggaccaac    540
aggtccgccg tccgccggac gctgttcacg tcgtggcgga gccccgggga tcccggcacc    600
ggggacttca cgctggggca ggacccgctc ggctccgcgc agctctacat ctggcggacc    660
ggcggcgaga acaccaacag cacctactgg cggtccgggc agtgggccaa caccaacttc    720
gtgggcgtgc catggcggtc gctctacgtg tacggcttca agctcaacgg cgacccgtac    780
aacgactccg gtgtcatgtc ctacgtcttc aacacgtaca acagctccga gtaccggttc    840
atgctccact ccaacggcac cgagacgtgc tacatgctgc tcgacaccgg cgactgggag    900
accgtctggt cgcagccgac catcccgtgc caggcctaca acatgtgcgg cgccaacgcc    960
cggtgcgccg gcggcggcgg cggcgacgac ggccagcagg ccgtctgcac ctgcttgaca   1020
ggcttcgagc cgaggaatgt gtcggagtac ggcaacggga actggacgca gggatgcgtc   1080
aggagctccc cgctggcctg cagcagcgac gcgaacgtga gtggcggcgg cggcggcgat   1140
ggcttcgccg acctccccgg cgtgaagctg cccaacttcg cggcgtgggg atccacggtg   1200
ggcgacgcgg acgcgtgcaa gcagtcgtgc ctggccaact gctcgtgcgg cgcgtacagc   1260
tacagcggtg gcaccggctg cctcacctgg ggacaggacc tgctggacat ctaccagttc   1320
ccggatggag aaggatacga tctgcagatc aaggtccctg catacttact agatcagacg   1380
ggctccagaa gaaggcgatg gacgacagtt gccgttgctg tagttatcgt cgtggttgta   1440
ttggcaggat gcggccttct cctgtggaaa tgcaggagaa gaatcaaaga gaaacttggc   1500
attgttggta gggagaagac aaagacgaca acgcagccgt ctctgcttcc tttgagggaa   1560
gcacggcagg atttctcagg gccgaaacag gttgatcaag aggaagcaga gggcggcaag   1620
aagtgcgagc tgcctctctt ctccttggag atggttgcag cggccaccgg cgacttcagc   1680
gccgacaaca agcttggaga gggaggcttt ggccatgtct acaagggaag acttcccggt   1740
ggcgaagagg ttgcggtgaa gaggctgtcc cggggctcag ggcaggggct ggaggagttc   1800
aagaacgagg tgatcctgat cgccaagctg cagcaccgca accttgtgaa gttgctaggt   1860
tgctgcatcc agggggagga gaagatcctg gtctacgagt acatgcccaa caagagcctc   1920
gacgccttcc tcttcgatcc ggcgcggcga gggctgctgg actggaagac gaggttccac   1980
atcatcgagg gcatcgcccg tggcctcctg tacctccacc gtgactcgcg gctccgggtg   2040
gtgcaccggg acctcaaggc cagcaacatc ctgctggacc gcgacatgaa ccccaagatc   2100
```

```
tccgacttcg gcatggcgcg gatcttcggc ggcgaccaga accaggtgaa cacgaaccgc   2160

gtggtgggca cgctgggcta catgtcgccc gagtacgcca tggagggcct cttctccgtg   2220

cgctccgacg tctacagctt cggcatcctc atcctggaga tcgtctccgg gcagaagaac   2280

agcagcttcc accgcatgga gggctccctc aacatcgtcg gccacgcgtg gcagctctgg   2340

aacgccgaca gaggggagca gctcatcgac ccggccatcc tgccggcgtg ccccgtgcgg   2400

gaggcgctcc gctgcgtgca catggcgctg ctgtgcgtgc aggaccacgc gtgcgaccgc   2460

ccggacatct cctacgtcgt catggcgctc ggcagcgaca gctccgtgct gccgatgcct   2520

aagccgccga cgttcacgct gcagtgcacg tcgtcggaca gggacgggat cttcccggag   2580

agagtcgatg agtcctactc cgcctgtgac ctcaccgtca caatgctgca tgggaggtag   2640
```

<210> SEQ ID NO 58
<211> LENGTH: 879
<212> TYPE: PRT
<213> ORGANISM: Sorghum bicolor

<400> SEQUENCE: 58

```
Met Ala His Ala Ala Val Ala Ala Leu Ala Leu Leu Val Phe Phe Ser
1               5                   10                  15

Ala Gln Ala Arg Arg Asp Gly Ala Gly Val Tyr Val Val Asp Ala Ala
            20                  25                  30

Ala Ala Leu Ser Gln Gly His Ser Leu Gly Ala Gly Asp Lys Leu Val
        35                  40                  45

Ser Ser Asp Gly Thr Phe Glu Leu Ala Phe Phe Thr Pro Thr Gly Ala
    50                  55                  60

Ala Asp Pro Ser Arg Arg Tyr Leu Gly Val Met Tyr Ala Gln Ser Asn
65                  70                  75                  80

Glu Gln Thr Val Pro Trp Val Ala Asn Arg Asp Ala Pro Val Ser Ala
                85                  90                  95

Gly Ser Ser Tyr Ser Ala Thr Val Thr Asp Ala Gly Glu Leu Gln Val
            100                 105                 110

Leu Glu Gly Glu Arg Val Val Trp Arg Thr Asn Ser Ala Thr Thr Ala
        115                 120                 125

Ser Ser Ser Ser Ser Ser Pro Ala Asn Val Thr Leu Thr Leu Leu Asp
    130                 135                 140

Thr Gly Asn Leu Gln Leu Thr Ala Gly Ala Thr Val Leu Trp Gln Ser
145                 150                 155                 160

Phe Asp His Pro Ala Asp Thr Phe Leu Pro Gly Met Ser Ile Thr Leu
                165                 170                 175

Asp Arg Thr Asn Arg Ser Ala Val Arg Arg Thr Leu Phe Thr Ser Trp
            180                 185                 190

Arg Ser Pro Gly Asp Pro Gly Thr Gly Asp Phe Thr Leu Gly Gln Asp
        195                 200                 205

Pro Leu Gly Ser Ala Gln Leu Tyr Ile Trp Arg Thr Gly Gly Glu Asn
    210                 215                 220

Thr Asn Ser Thr Tyr Trp Arg Ser Gly Gln Trp Ala Asn Thr Asn Phe
225                 230                 235                 240

Val Gly Val Pro Trp Arg Ser Leu Tyr Val Tyr Gly Phe Lys Leu Asn
                245                 250                 255

Gly Asp Pro Tyr Asn Asp Ser Gly Val Met Ser Tyr Val Phe Asn Thr
            260                 265                 270

Tyr Asn Ser Ser Glu Tyr Arg Phe Met Leu His Ser Asn Gly Thr Glu
```

```
        275                 280                 285

Thr Cys Tyr Met Leu Leu Asp Thr Gly Asp Trp Glu Thr Val Trp Ser
    290                 295                 300

Gln Pro Thr Ile Pro Cys Gln Ala Tyr Asn Met Cys Gly Ala Asn Ala
305                 310                 315                 320

Arg Cys Ala Gly Gly Gly Gly Gly Asp Asp Gly Gln Gln Ala Val Cys
                325                 330                 335

Thr Cys Leu Thr Gly Phe Glu Pro Arg Asn Val Ser Glu Tyr Gly Asn
            340                 345                 350

Gly Asn Trp Thr Gln Gly Cys Val Arg Ser Ser Pro Leu Ala Cys Ser
        355                 360                 365

Ser Asp Ala Asn Val Ser Gly Gly Gly Gly Gly Asp Gly Phe Ala Asp
    370                 375                 380

Leu Pro Gly Val Lys Leu Pro Asn Phe Ala Ala Trp Gly Ser Thr Val
385                 390                 395                 400

Gly Asp Ala Asp Ala Cys Lys Gln Ser Cys Leu Ala Asn Cys Ser Cys
                405                 410                 415

Gly Ala Tyr Ser Tyr Ser Gly Gly Thr Gly Cys Leu Thr Trp Gly Gln
            420                 425                 430

Asp Leu Leu Asp Ile Tyr Gln Phe Pro Asp Gly Glu Gly Tyr Asp Leu
        435                 440                 445

Gln Ile Lys Val Pro Ala Tyr Leu Leu Asp Gln Thr Gly Ser Arg Arg
    450                 455                 460

Arg Arg Trp Thr Thr Val Ala Val Ala Val Val Ile Val Val Val Val
465                 470                 475                 480

Leu Ala Gly Cys Gly Leu Leu Leu Trp Lys Cys Arg Arg Arg Ile Lys
                485                 490                 495

Glu Lys Leu Gly Ile Val Gly Arg Glu Lys Thr Lys Thr Thr Thr Gln
            500                 505                 510

Pro Ser Leu Leu Pro Leu Arg Glu Ala Arg Gln Asp Phe Ser Gly Pro
        515                 520                 525

Lys Gln Val Asp Gln Glu Glu Ala Glu Gly Gly Lys Lys Cys Glu Leu
    530                 535                 540

Pro Leu Phe Ser Leu Glu Met Val Ala Ala Ala Thr Gly Asp Phe Ser
545                 550                 555                 560

Ala Asp Asn Lys Leu Gly Glu Gly Gly Phe Gly His Val Tyr Lys Gly
                565                 570                 575

Arg Leu Pro Gly Gly Glu Glu Val Ala Val Lys Arg Leu Ser Arg Gly
            580                 585                 590

Ser Gly Gln Gly Leu Glu Glu Phe Lys Asn Glu Val Ile Leu Ile Ala
        595                 600                 605

Lys Leu Gln His Arg Asn Leu Val Lys Leu Leu Gly Cys Cys Ile Gln
    610                 615                 620

Gly Glu Glu Lys Ile Leu Val Tyr Glu Tyr Met Pro Asn Lys Ser Leu
625                 630                 635                 640

Asp Ala Phe Leu Phe Asp Pro Ala Arg Arg Gly Leu Leu Asp Trp Lys
                645                 650                 655

Thr Arg Phe His Ile Ile Glu Gly Ile Ala Arg Gly Leu Leu Tyr Leu
            660                 665                 670

His Arg Asp Ser Arg Leu Arg Val Val His Arg Asp Leu Lys Ala Ser
        675                 680                 685

Asn Ile Leu Leu Asp Arg Asp Met Asn Pro Lys Ile Ser Asp Phe Gly
    690                 695                 700
```

-continued

```
Met Ala Arg Ile Phe Gly Gly Asp Gln Asn Gln Val Asn Thr Asn Arg
705                 710                 715                 720

Val Val Gly Thr Leu Gly Tyr Met Ser Pro Glu Tyr Ala Met Glu Gly
                725                 730                 735

Leu Phe Ser Val Arg Ser Asp Val Tyr Ser Phe Gly Ile Leu Ile Leu
            740                 745                 750

Glu Ile Val Ser Gly Gln Lys Asn Ser Ser Phe His Arg Met Glu Gly
        755                 760                 765

Ser Leu Asn Ile Val Gly His Ala Trp Gln Leu Trp Asn Ala Asp Arg
    770                 775                 780

Gly Glu Gln Leu Ile Asp Pro Ala Ile Leu Pro Ala Cys Pro Val Arg
785                 790                 795                 800

Glu Ala Leu Arg Cys Val His Met Ala Leu Leu Cys Val Gln Asp His
                805                 810                 815

Ala Cys Asp Arg Pro Asp Ile Ser Tyr Val Val Met Ala Leu Gly Ser
            820                 825                 830

Asp Ser Ser Val Leu Pro Met Pro Lys Pro Pro Thr Phe Thr Leu Gln
        835                 840                 845

Cys Thr Ser Ser Asp Arg Asp Gly Ile Phe Pro Glu Arg Val Asp Glu
    850                 855                 860

Ser Tyr Ser Ala Cys Asp Leu Thr Val Thr Met Leu His Gly Arg
865                 870                 875
```

<210> SEQ ID NO 59
<211> LENGTH: 2523
<212> TYPE: DNA
<213> ORGANISM: Arabidopsis thaliana

<400> SEQUENCE: 59

```
atggtggttt cagtgaccat acgtcgtcgt tttgttcttc ttctacttgc atgcacttgt     60

ttgttgtctc ggagactctg ttttggtgag gacagaatca ctttctcaag tcctatcaaa    120

gactcagagt cagagaccct tctatgcaaa agtggtattt tcaggtttgg tttcttcact    180

cctgttaatt ccactactcg gttacgttat gttgggattt ggtacgaaaa gattccaatc    240

caaactgtgg tttgggttgc taacaaagac tctcccatca acgacacttc cggtgttatc    300

tcgatctatc aagatggaaa tctcgcggtt accgatggtc gaaatcgcct tgtatggtcg    360

acgaatgtct cagtaccagt agctccaaat gctacttggg ttcagcttat ggattctggg    420

aatcttatgt tacaagacaa cagaaacaat ggtgagattc tttgggagag tttcaagcat    480

ccttatgatt ctttcatgcc aagaatgact cttggcaccg acggtagaac tggaggtaac    540

ctaaagctta cttcttggac aagccacgat gatccttcaa caggaaacta cacagctggt    600

attgctcctt tcacgtttcc tgagcttctt atctggaaga acaatgtccc aacgtggcgt    660

agcggaccgt ggaacggtca ggttttcatc ggtttaccga atatggattc acttctgttt    720

cttgatgggt ttaatcttaa cagtgataat caaggaacga tctcaatgtc ttatgctaat    780

gattcgttca tgtatcactt taacttggat cctgaaggaa ttatttatca gaaagattgg    840

agtacttcta tgagaacttg gaggataggt gtaaagtttc catacacaga ctgtgatgca    900

tacggtagat gtggtcgatt cgggagctgc catgccgggg aaaacccgcc ttgtaaatgt    960

gttaaagggt ttgttccaaa gaataacaca gagtggaatg gtggtaattg gagtaatgga   1020

tgtatgagaa aagctccatt gcagtgtgaa agacagagaa atgtaagtaa tggtggtggt   1080

ggaggaaaag cagatggttt tttgaaactg cagaagatga aagtaccaat ctctgcggaa   1140
```

```
cggtctgaag ctagtgaaca agtttgtcct aaagtatgct tagataactg ttcttgcaca   1200

gcttatgcat atgatagagg aattggatgc atgctttgga gtggtgattt agttgatatg   1260

caatcatttt tgggaagtgg cattgatctt tttattcgtg ttgctcattc agaactcaaa   1320

acacatagca atctagcagt tatgatcgca gcacctgtga taggcgttat gttaattgct   1380

gcggtctgcg ttcttttagc atgccggaaa tacaaaaagc gtccagcgaa agatagaagt   1440

gcagagctaa tgtttaagag aatggaagca cttacaagtg ataatgagtc tgcttctaac   1500

caaatcaagc tcaaggagct tccactcttt gagtttcaag tgttagctac atcaactgat   1560

agcttctctc taagaaacaa gctcgggcaa ggcgggtttg gtcctgttta caagggaaaa   1620

ttacctgaag gacaagaaat tgcagtgaag aggctctcac ggaaatcagg tcaaggacta   1680

gaggaactta tgaacgaagt ggttgtgata tctaagttgc aacatcggaa tctagtgaag   1740

ttacttggat gttgtattga aggtgaagaa agaatgttag tatatgaata tatgccaaag   1800

aaaagcttgg atgcatatct tttgaccca atgaagcaaa agattcttga ttggaagact   1860

cggttcaaca taatggaagg aatttgcaga ggtcttttgt accttcacag agattcaaga   1920

ctaaagatca tacacagaga tttaaaagcc agcaacattt tgttagatga gaatctaaac   1980

cccaagatat ctgattttgg acttgcaaga attttccgag cgaatgaaga tgaagctaac   2040

acaagaaggg ttgttggaac atacggctat atgtcaccgg agtatgcaat ggaaggtttc   2100

ttttcagaaa aatcagatgt tttcagcttg gggttatat ttctcgagat cataagtggg   2160

agaagaaact ctagttctca caaggaagag aataatctca accttttggc ttatgcttgg   2220

aagctgtgga acgacggtga ggctgcttct ctagcagatc cagccgtctt tgataagtgt   2280

ttcgagaaag agatagagaa atgtgttcat attggactgt tatgtgtgca agaagttgca   2340

aacgatagac caaatgtttc aaacgtgata tggatgctaa ctaccgagaa catgagcctc   2400

gccgatccga agcagccagc gtttatagta agaagaggag cttctgaggc tgaatcttct   2460

gaccagagta gtcaaaaggt atctatcaat gatgtgagcc tcacagctgt aacaggacgt   2520

taa                                                                 2523
```

<210> SEQ ID NO 60
<211> LENGTH: 840
<212> TYPE: PRT
<213> ORGANISM: Arabidopsis thaliana

<400> SEQUENCE: 60

```
Met Val Val Ser Val Thr Ile Arg Arg Arg Phe Val Leu Leu Leu Leu
1               5                   10                  15

Ala Cys Thr Cys Leu Leu Ser Arg Arg Leu Cys Phe Gly Glu Asp Arg
            20                  25                  30

Ile Thr Phe Ser Ser Pro Ile Lys Asp Ser Glu Ser Glu Thr Leu Leu
        35                  40                  45

Cys Lys Ser Gly Ile Phe Arg Phe Gly Phe Phe Thr Pro Val Asn Ser
    50                  55                  60

Thr Thr Arg Leu Arg Tyr Val Gly Ile Trp Tyr Glu Lys Ile Pro Ile
65                  70                  75                  80

Gln Thr Val Val Trp Val Ala Asn Lys Asp Ser Pro Ile Asn Asp Thr
                85                  90                  95

Ser Gly Val Ile Ser Ile Tyr Gln Asp Gly Asn Leu Ala Val Thr Asp
            100                 105                 110

Gly Arg Asn Arg Leu Val Trp Ser Thr Asn Val Ser Val Pro Val Ala
```

```
        115                 120                 125

Pro Asn Ala Thr Trp Val Gln Leu Met Asp Ser Gly Asn Leu Met Leu
    130                 135                 140

Gln Asp Asn Arg Asn Asn Gly Glu Ile Leu Trp Glu Ser Phe Lys His
145                 150                 155                 160

Pro Tyr Asp Ser Phe Met Pro Arg Met Thr Leu Gly Thr Asp Gly Arg
                165                 170                 175

Thr Gly Gly Asn Leu Lys Leu Thr Ser Trp Thr Ser His Asp Asp Pro
            180                 185                 190

Ser Thr Gly Asn Tyr Thr Ala Gly Ile Ala Pro Phe Thr Phe Pro Glu
        195                 200                 205

Leu Leu Ile Trp Lys Asn Asn Val Pro Thr Trp Arg Ser Gly Pro Trp
    210                 215                 220

Asn Gly Gln Val Phe Ile Gly Leu Pro Asn Met Asp Ser Leu Leu Phe
225                 230                 235                 240

Leu Asp Gly Phe Asn Leu Asn Ser Asp Asn Gln Gly Thr Ile Ser Met
                245                 250                 255

Ser Tyr Ala Asn Asp Ser Phe Met Tyr His Phe Asn Leu Asp Pro Glu
            260                 265                 270

Gly Ile Ile Tyr Gln Lys Asp Trp Ser Thr Ser Met Arg Thr Trp Arg
        275                 280                 285

Ile Gly Val Lys Phe Pro Tyr Thr Asp Cys Asp Ala Tyr Gly Arg Cys
    290                 295                 300

Gly Arg Phe Gly Ser Cys His Ala Gly Glu Asn Pro Pro Cys Lys Cys
305                 310                 315                 320

Val Lys Gly Phe Val Pro Lys Asn Asn Thr Glu Trp Asn Gly Gly Asn
                325                 330                 335

Trp Ser Asn Gly Cys Met Arg Lys Ala Pro Leu Gln Cys Glu Arg Gln
            340                 345                 350

Arg Asn Val Ser Asn Gly Gly Gly Gly Gly Lys Ala Asp Gly Phe Leu
        355                 360                 365

Lys Leu Gln Lys Met Lys Val Pro Ile Ser Ala Glu Arg Ser Glu Ala
    370                 375                 380

Ser Glu Gln Val Cys Pro Lys Val Cys Leu Asp Asn Cys Ser Cys Thr
385                 390                 395                 400

Ala Tyr Ala Tyr Asp Arg Gly Ile Gly Cys Met Leu Trp Ser Gly Asp
                405                 410                 415

Leu Val Asp Met Gln Ser Phe Leu Gly Ser Gly Ile Asp Leu Phe Ile
            420                 425                 430

Arg Val Ala His Ser Glu Leu Lys Thr His Ser Asn Leu Ala Val Met
        435                 440                 445

Ile Ala Ala Pro Val Ile Gly Val Met Leu Ile Ala Ala Val Cys Val
    450                 455                 460

Leu Leu Ala Cys Arg Lys Tyr Lys Lys Arg Pro Ala Lys Asp Arg Ser
465                 470                 475                 480

Ala Glu Leu Met Phe Lys Arg Met Glu Ala Leu Thr Ser Asp Asn Glu
                485                 490                 495

Ser Ala Ser Asn Gln Ile Lys Leu Lys Glu Leu Pro Leu Phe Glu Phe
            500                 505                 510

Gln Val Leu Ala Thr Ser Thr Asp Ser Phe Ser Leu Arg Asn Lys Leu
        515                 520                 525

Gly Gln Gly Gly Phe Gly Pro Val Tyr Lys Gly Lys Leu Pro Glu Gly
    530                 535                 540
```

```
Gln Glu Ile Ala Val Lys Arg Leu Ser Arg Lys Ser Gly Gln Gly Leu
545                 550                 555                 560

Glu Glu Leu Met Asn Glu Val Val Val Ile Ser Lys Leu Gln His Arg
                565                 570                 575

Asn Leu Val Lys Leu Leu Gly Cys Cys Ile Glu Gly Glu Glu Arg Met
            580                 585                 590

Leu Val Tyr Glu Tyr Met Pro Lys Lys Ser Leu Asp Ala Tyr Leu Phe
        595                 600                 605

Asp Pro Met Lys Gln Lys Ile Leu Asp Trp Lys Thr Arg Phe Asn Ile
    610                 615                 620

Met Glu Gly Ile Cys Arg Gly Leu Leu Tyr Leu His Arg Asp Ser Arg
625                 630                 635                 640

Leu Lys Ile Ile His Arg Asp Leu Lys Ala Ser Asn Ile Leu Leu Asp
                645                 650                 655

Glu Asn Leu Asn Pro Lys Ile Ser Asp Phe Gly Leu Ala Arg Ile Phe
            660                 665                 670

Arg Ala Asn Glu Asp Glu Ala Asn Thr Arg Arg Val Val Gly Thr Tyr
        675                 680                 685

Gly Tyr Met Ser Pro Glu Tyr Ala Met Glu Gly Phe Phe Ser Glu Lys
    690                 695                 700

Ser Asp Val Phe Ser Leu Gly Val Ile Phe Leu Glu Ile Ile Ser Gly
705                 710                 715                 720

Arg Arg Asn Ser Ser Ser His Lys Glu Glu Asn Asn Leu Asn Leu Leu
                725                 730                 735

Ala Tyr Ala Trp Lys Leu Trp Asn Asp Gly Glu Ala Ala Ser Leu Ala
            740                 745                 750

Asp Pro Ala Val Phe Asp Lys Cys Phe Glu Lys Glu Ile Glu Lys Cys
        755                 760                 765

Val His Ile Gly Leu Leu Cys Val Gln Glu Val Ala Asn Asp Arg Pro
    770                 775                 780

Asn Val Ser Asn Val Ile Trp Met Leu Thr Thr Glu Asn Met Ser Leu
785                 790                 795                 800

Ala Asp Pro Lys Gln Pro Ala Phe Ile Val Arg Arg Gly Ala Ser Glu
                805                 810                 815

Ala Glu Ser Ser Asp Gln Ser Ser Gln Lys Val Ser Ile Asn Asp Val
            820                 825                 830

Ser Leu Thr Ala Val Thr Gly Arg
        835                 840
```

<210> SEQ ID NO 61
<211> LENGTH: 2226
<212> TYPE: DNA
<213> ORGANISM: Glycine max

<400> SEQUENCE: 61

```
ttgctatcct tgtttcctac agctttggaa gcagaggatg caataactcc accacaaacc     60

atcagtggct accagacact agtctcacct tcccaaaatt ttgaactggg tttcttcagt    120

cctggcaatt ccactcacat ctatcttgga atatggtaca agcatatccc aaaacagaca    180

gttatttggg ttgcaaatag agacaaacca ttagttaact ctggtggctc cttaacattc    240

agcaacaatg gcaagctcat ccttctcagc cacacaggaa gtgttgtatg gtcttcaaac    300

tcatctggac ctgcaagaaa cccagtggca catcttctag actctggaaa ctttgtgttg    360

aaggactacg gaaatgaggg acatttgtgg gagagttttg attatccatc tgacacattg    420
```

```
ataccaggaa tgaagcttgg ttggaacttc aaaactggct tgaaccgaca tttgacttcc    480
tggaaaagct cttctaatcc ttcttcaggt gaatacactt acggtgtgga tccccggggg    540
attcctcagc tttttcttca caagggaaac aagaaggtct tcagaagtgg accatggtat    600
gggcaacaat tcaaaggtga tccagttctc agtgcaaatc cagttttcaa acccattttt    660
gtttttgatt ctgatgaagt gtcttactct tatgagacca aagacaccat tgtttcaaga    720
tttgtgctga gtcagtctgg tttgattcag catttttcat ggaatgatca tcattccagt    780
tggttctcag aattctcagt tcaaggggac cgctgtgatg attatggcct ttgtggtgca    840
tatggttctt gtaacatcaa aagctcccct gtttgcaaat gtttgaaggg ttttgatcct    900
aagcttccgc aagaatggga gaagaatgag tggtcaggtg gatgtgttag gaagaattca    960
caggttttca gcaatggaga cacatttaag cagtttacag gaatgaaact accagatgct   1020
gctgagtttc atacaaacta caccatcagc agtgatcact gtgaggcaga atgctccatg   1080
aactgctctt gtgttgctta tgccaaacta gatgtaaatg caagcggcaa aggctgtatt   1140
gtatggtttg ggatttatt tgatataaga gaggtttctg tgaatggaga agatttttac   1200
gtaagagttc cagcttcaga agtagccaaa gagacagata gtcagtttag tgttggcaga   1260
gctaggagtg aaagaaatga atttaaactc ccattgtttg agattgccat aattgaagcc   1320
gcaaccgaga atttctctct ttacaacaag attggagaag gaggatttgg tcatgtatac   1380
aaaggtcaac ttccatcagg acaggaaata gctgtgaaga ggctgtcaga gaattctgga   1440
caaggcctgc aggagttcaa gaatgaggtc attttgatct cccaacttca gcatcgaaat   1500
cttgtcaagc ttctgggatg ttgcattcat ggagaagata aaatgttggt ctacgaatac   1560
atgccaaaca gaagcttgga ctccttatta tttgatgaaa ccaagcgttc tgtgctcagt   1620
tggcaaaaga ggctagacat aattatcggc attgctcggg gacttctcta ccttcacaga   1680
gattcaagat tgagaataat ccatagagac ctgaaagcaa gcaatgttct tttagatggt   1740
gaaatgaacc caaaaatttc tgactttgga atggcaagaa tgtttggggg tgatcaaact   1800
gaagcaaaga ccaagagaat agtgggaacc tatggatata tgtccccaga gtatgcaata   1860
gatggacact tctctttcaa atcagatgtt tatagctttg gggttttact cttggagctg   1920
ttgagtggca agaaaaacaa aggatttatt cacccagatc acaaactgaa tctcctaggc   1980
catgcatgga agctatggaa tgaagatagg gccttggagc tgatggatgc attgcttgag   2040
aatcagtttc ctacatctga agctctaagg tgtattcaag tgggtctgtc atgcattcaa   2100
cagcacccag aagataggcc aacaatgtca tcagtgcttt tgatgttcga cagtgagagt   2160
gtgttggtcc cccaacctgg aaggccagga ttatattccg agagattttt ctctgggaca   2220
aattca                                                              2226
```

<210> SEQ ID NO 62
<211> LENGTH: 742
<212> TYPE: PRT
<213> ORGANISM: Glycine max

<400> SEQUENCE: 62

```
Leu Leu Ser Leu Phe Pro Thr Ala Leu Glu Ala Glu Asp Ala Ile Thr
1               5                   10                  15

Pro Pro Gln Thr Ile Ser Gly Tyr Gln Thr Leu Val Ser Pro Ser Gln
            20                  25                  30

Asn Phe Glu Leu Gly Phe Phe Ser Pro Gly Asn Ser Thr His Ile Tyr
        35                  40                  45
```

```
Leu Gly Ile Trp Tyr Lys His Ile Pro Lys Gln Thr Val Ile Trp Val
    50                  55                  60

Ala Asn Arg Asp Lys Pro Leu Val Asn Ser Gly Gly Ser Leu Thr Phe
65                  70                  75                  80

Ser Asn Asn Gly Lys Leu Ile Leu Leu Ser His Thr Gly Ser Val Val
                85                  90                  95

Trp Ser Ser Asn Ser Ser Gly Pro Ala Arg Asn Pro Val Ala His Leu
            100                 105                 110

Leu Asp Ser Gly Asn Phe Val Leu Lys Asp Tyr Gly Asn Glu Gly His
        115                 120                 125

Leu Trp Glu Ser Phe Asp Tyr Pro Ser Asp Thr Leu Ile Pro Gly Met
    130                 135                 140

Lys Leu Gly Trp Asn Phe Lys Thr Gly Leu Asn Arg His Leu Thr Ser
145                 150                 155                 160

Trp Lys Ser Ser Ser Asn Pro Ser Ser Gly Glu Tyr Thr Tyr Gly Val
                165                 170                 175

Asp Pro Arg Gly Ile Pro Gln Leu Phe Leu His Lys Gly Asn Lys Lys
            180                 185                 190

Val Phe Arg Ser Gly Pro Trp Tyr Gly Gln Gln Phe Lys Gly Asp Pro
        195                 200                 205

Val Leu Ser Ala Asn Pro Val Phe Lys Pro Ile Phe Val Phe Asp Ser
    210                 215                 220

Asp Glu Val Ser Tyr Ser Tyr Glu Thr Lys Asp Thr Ile Val Ser Arg
225                 230                 235                 240

Phe Val Leu Ser Gln Ser Gly Leu Ile Gln His Phe Ser Trp Asn Asp
                245                 250                 255

His His Ser Ser Trp Phe Ser Glu Phe Ser Val Gln Gly Asp Arg Cys
            260                 265                 270

Asp Asp Tyr Gly Leu Cys Gly Ala Tyr Gly Ser Cys Asn Ile Lys Ser
        275                 280                 285

Ser Pro Val Cys Lys Cys Leu Lys Gly Phe Asp Pro Lys Leu Pro Gln
    290                 295                 300

Glu Trp Glu Lys Asn Glu Trp Ser Gly Gly Cys Val Arg Lys Asn Ser
305                 310                 315                 320

Gln Val Phe Ser Asn Gly Asp Thr Phe Lys Gln Phe Thr Gly Met Lys
                325                 330                 335

Leu Pro Asp Ala Ala Glu Phe His Thr Asn Tyr Thr Ile Ser Ser Asp
            340                 345                 350

His Cys Glu Ala Glu Cys Ser Met Asn Cys Ser Cys Val Ala Tyr Ala
        355                 360                 365

Lys Leu Asp Val Asn Ala Ser Gly Lys Gly Cys Ile Val Trp Phe Gly
    370                 375                 380

Asp Leu Phe Asp Ile Arg Glu Val Ser Val Asn Gly Glu Asp Phe Tyr
385                 390                 395                 400

Val Arg Val Pro Ala Ser Glu Val Ala Lys Glu Thr Asp Ser Gln Phe
                405                 410                 415

Ser Val Gly Arg Ala Arg Ser Glu Arg Asn Glu Phe Lys Leu Pro Leu
            420                 425                 430

Phe Glu Ile Ala Ile Ile Glu Ala Ala Thr Glu Asn Phe Ser Leu Tyr
        435                 440                 445

Asn Lys Ile Gly Glu Gly Gly Phe Gly His Val Tyr Lys Gly Gln Leu
    450                 455                 460
```

```
Pro Ser Gly Gln Glu Ile Ala Val Lys Arg Leu Ser Glu Asn Ser Gly
465                 470                 475                 480

Gln Gly Leu Gln Glu Phe Lys Asn Glu Val Ile Leu Ile Ser Gln Leu
                485                 490                 495

Gln His Arg Asn Leu Val Lys Leu Leu Gly Cys Cys Ile His Gly Glu
            500                 505                 510

Asp Lys Met Leu Val Tyr Glu Tyr Met Pro Asn Arg Ser Leu Asp Ser
        515                 520                 525

Leu Leu Phe Asp Glu Thr Lys Arg Ser Val Leu Ser Trp Gln Lys Arg
    530                 535                 540

Leu Asp Ile Ile Ile Gly Ile Ala Arg Gly Leu Leu Tyr Leu His Arg
545                 550                 555                 560

Asp Ser Arg Leu Arg Ile Ile His Arg Asp Leu Lys Ala Ser Asn Val
                565                 570                 575

Leu Leu Asp Gly Glu Met Asn Pro Lys Ile Ser Asp Phe Gly Met Ala
            580                 585                 590

Arg Met Phe Gly Gly Asp Gln Thr Glu Ala Lys Thr Lys Arg Ile Val
        595                 600                 605

Gly Thr Tyr Gly Tyr Met Ser Pro Glu Tyr Ala Ile Asp Gly His Phe
    610                 615                 620

Ser Phe Lys Ser Asp Val Tyr Ser Phe Gly Val Leu Leu Leu Glu Leu
625                 630                 635                 640

Leu Ser Gly Lys Lys Asn Lys Gly Phe Ile His Pro Asp His Lys Leu
                645                 650                 655

Asn Leu Leu Gly His Ala Trp Lys Leu Trp Asn Glu Asp Arg Ala Leu
            660                 665                 670

Glu Leu Met Asp Ala Leu Leu Glu Asn Gln Phe Pro Thr Ser Glu Ala
        675                 680                 685

Leu Arg Cys Ile Gln Val Gly Leu Ser Cys Ile Gln Gln His Pro Glu
    690                 695                 700

Asp Arg Pro Thr Met Ser Ser Val Leu Leu Met Phe Asp Ser Glu Ser
705                 710                 715                 720

Val Leu Val Pro Gln Pro Gly Arg Pro Gly Leu Tyr Ser Glu Arg Phe
                725                 730                 735

Phe Ser Gly Thr Asn Ser
            740


<210> SEQ ID NO 63
<211> LENGTH: 987
<212> TYPE: DNA
<213> ORGANISM: Oryza sativa

<400> SEQUENCE: 63

atgcagagtt acagtgagaa gagatctcat aagatatttt tggaaagcct tctcgtgtgt     60

ggaatttgtc taagtgagga tgttggcaga aatttcatca agctcccatg ccatcattcc    120

ttttgtttga agtgtatgga gtctcactgc aaaatccatg tgaaagaagg gaatttaatg    180

cagctggcat gtcctgatac aaattgccgc aatccacttc cgccatccgt attgaaaagc    240

cttctacgag atgatggata tgcacaatgg gaatcatttg ctctacagaa actgttagat    300

gcaatgcctg atctagttta ctgccccagg tgttctgctg cttgcttgga agttgacaat    360

gatgctcaat gcccgggttg tttttttacc ttctgcactt tgtgcaaacg ccgccgccat    420

gtgggggata catgtattac tcctgaagaa aaaatacgca ttttgaagga acgacagaaa    480

ttgtattcca taccagagga acaattgttg aaagaaaaga gggaaataga cgagttgata    540
```

```
aatatccagg aagcacttcg tgattctaag caatgccctc gttgtaagat ggctatctca    600

aaaattgaag gttgcaacaa gatgacatgt gggaactgtg ggagattctt ctgctatcgt    660

tgtaacaaag caattggagg atatgatcat ttctggaatg gaaactgtga tatgtttgag    720

agggaacaag atgaaaaccc acagcagcag gatgatgaaa attttggtgg cgaccctgac    780

gaagatgctg aactcttaga acctgaatgg gtgctgttaa cttatccctg tccaaactgt    840

ggccgtcgga atgaaaagct cggtaccaac aatcatatac tttgcatcgg atgccgaggc    900

cattattgtg cgttgtgtcg gaaaagagtt ttgaggggcg agcaacactt tggacctaga    960

ggctgccagc aacacactga agattga                                         987
```

<210> SEQ ID NO 64
<211> LENGTH: 328
<212> TYPE: PRT
<213> ORGANISM: Oryza sativa

<400> SEQUENCE: 64

```
Met Gln Ser Tyr Ser Glu Lys Arg Ser His Lys Ile Phe Leu Glu Ser
1               5                   10                  15

Leu Leu Val Cys Gly Ile Cys Leu Ser Glu Asp Val Gly Arg Asn Phe
            20                  25                  30

Ile Lys Leu Pro Cys His His Ser Phe Cys Leu Lys Cys Met Glu Ser
        35                  40                  45

His Cys Lys Ile His Val Lys Glu Gly Asn Leu Met Gln Leu Ala Cys
    50                  55                  60

Pro Asp Thr Asn Cys Arg Asn Pro Leu Pro Pro Ser Val Leu Lys Ser
65                  70                  75                  80

Leu Leu Arg Asp Asp Gly Tyr Ala Gln Trp Glu Ser Phe Ala Leu Gln
                85                  90                  95

Lys Leu Leu Asp Ala Met Pro Asp Leu Val Tyr Cys Pro Arg Cys Ser
            100                 105                 110

Ala Ala Cys Leu Glu Val Asp Asn Asp Ala Gln Cys Pro Gly Cys Phe
        115                 120                 125

Phe Thr Phe Cys Thr Leu Cys Lys Arg Arg Arg His Val Gly Asp Thr
    130                 135                 140

Cys Ile Thr Pro Glu Glu Lys Ile Arg Ile Leu Lys Glu Arg Gln Lys
145                 150                 155                 160

Leu Tyr Ser Ile Pro Glu Glu Gln Leu Leu Lys Glu Lys Arg Glu Ile
                165                 170                 175

Asp Glu Leu Ile Asn Ile Gln Glu Ala Leu Arg Asp Ser Lys Gln Cys
            180                 185                 190

Pro Arg Cys Lys Met Ala Ile Ser Lys Ile Glu Gly Cys Asn Lys Met
        195                 200                 205

Thr Cys Gly Asn Cys Gly Arg Phe Phe Cys Tyr Arg Cys Asn Lys Ala
    210                 215                 220

Ile Gly Gly Tyr Asp His Phe Trp Asn Gly Asn Cys Asp Met Phe Glu
225                 230                 235                 240

Arg Glu Gln Asp Glu Asn Pro Gln Gln Gln Asp Asp Glu Asn Phe Gly
                245                 250                 255

Gly Asp Pro Asp Glu Asp Ala Glu Leu Leu Glu Pro Glu Trp Val Leu
            260                 265                 270

Leu Thr Tyr Pro Cys Pro Asn Cys Gly Arg Arg Asn Glu Lys Leu Gly
        275                 280                 285
```

Thr Asn Asn His Ile Leu Cys Ile Gly Cys Arg Gly His Tyr Cys Ala
    290                 295                 300

Leu Cys Arg Lys Arg Val Leu Arg Gly Glu Gln His Phe Gly Pro Arg
305                 310                 315                 320

Gly Cys Gln Gln His Thr Glu Asp
                325

<210> SEQ ID NO 65
<211> LENGTH: 1686
<212> TYPE: DNA
<213> ORGANISM: Zea mays

<400> SEQUENCE: 65
atgtccagcg gagccacgtc atcgtcctcg ccgccgctgg cagaggctgg ggacggatac 60
tgggaggggc gggaggaggc ggtggcgcgg ctgaaggcga tggccgcgag ggctcattgg 120
gaggacgaac tctcggcgga gcggttggag accaacaacc aggtgcagga ggacgagatg 180
ctggcactgc aagccattta tggggatgac atggttatct tggaggataa ggctggtttt 240
cgttcttttc agatttttgt ttggtatcca attcctaatg gtactaaggt gttcttgaat 300
cttcatccaa atggaactat ggttggaact gataatgatg agagcaaaga tggtggtgaa 360
ctcatctatg cttgcagttt aaagcatttg ccacctgtgg tgttaacatg tttgctgcca 420
tgttcatatc ccagtgcaag tgctccttat tttactatct cagccaagtg gttggatgaa 480
cccaaagttt cacacctctg taccatgttt gatgagattt ggactgagct gccaggacaa 540
gaagtagtgt atagatggct ggactggctg aatagctctt catgggcttg catttctttg 600
aatgacaaca taatactaat cgcagataaa acttcagatg ttggagatgc acgtgctatt 660
gcaagaaggc ttctagttga tcatactatt cctcttatgc aaagttacaa tgagaggagg 720
tctcatgaaa tatttctgaa aagcttacat aagtgccgaa tttgtcttag tgaaaatact 780
ggcagaaatt tcatcaagct cccatgccac catttgtttt gcttgacgtg tatgaagtct 840
cactgcagaa ttcacgtaac agaagggagt ttaaccaagc tcacatgccc tgatacaact 900
tgctgcagcc cacttccacc atcagttttg aaaagcctcc tgggagatga ttgctataag 960
cgatgggaat cattcgcgtt acagaagctc ttagatacaa tgcctgatct ggtatattgt 1020
ccgaggtgta atgctgcctg cttggaggat gacaatgatg ctcaatgccc agagtgtttt 1080
ttcaccttct gctctttgtg caaagaacgc aggcatgtgg ggaaggattg cgttactcca 1140
gaagaaaaga ttaggattct gagggaaaaa caccagaaat attccctccc agaaaaacaa 1200
ttgttgaaag aacagaggga aatagatgaa ttaataagtg tctgcgaagc gcttcgcgat 1260
tcgaagcaat gtccttcttg caaaatggct atctcaaaga ctgaaggatg caacaagatg 1320
atctgtagga actgcgggaa attcttctgt taccgttgta accaggcaat tcgtggatat 1380
gaacattttt gggatggaaa ttgcgtgcta tttgaacacc agaatcaagt gcaaatatat 1440
ggacggcttg aggagtccga tgatgaagaa catttttgatg atgaagatct agaggagaca 1500
gagcctgaac tggtatgggg ttgtccttgt ccagtgtgtg gtcggtggaa tggaaagctt 1560
gacacaaaca atcatatatt gtgcatgggt tgccgaggcc actattgcgc gttatgccgg 1620
aggagggtaa tgaagagctc cgaacactat ggaccaagag gttgccaaca acacacggat 1680
ccgtag 1686

<210> SEQ ID NO 66
<211> LENGTH: 561
<212> TYPE: PRT

<213> ORGANISM: Zea mays

<400> SEQUENCE: 66

```
Met Ser Ser Gly Ala Thr Ser Ser Ser Ser Pro Pro Leu Ala Glu Ala
1               5                   10                  15

Gly Asp Gly Tyr Trp Glu Gly Arg Glu Glu Ala Val Ala Arg Leu Lys
            20                  25                  30

Ala Met Ala Ala Arg Ala His Trp Glu Asp Glu Leu Ser Ala Glu Arg
        35                  40                  45

Leu Glu Thr Asn Asn Gln Val Gln Glu Asp Glu Met Leu Ala Leu Gln
    50                  55                  60

Ala Ile Tyr Gly Asp Asp Met Val Ile Leu Glu Asp Lys Ala Gly Phe
65                  70                  75                  80

Arg Ser Phe Gln Ile Phe Val Trp Tyr Pro Ile Pro Asn Gly Thr Lys
                85                  90                  95

Val Phe Leu Asn Leu His Pro Asn Gly Thr Met Val Gly Thr Asp Asn
            100                 105                 110

Asp Glu Ser Lys Asp Gly Gly Glu Leu Ile Tyr Ala Cys Ser Leu Lys
        115                 120                 125

His Leu Pro Pro Val Val Leu Thr Cys Leu Leu Pro Cys Ser Tyr Pro
    130                 135                 140

Ser Ala Ser Ala Pro Tyr Phe Thr Ile Ser Ala Lys Trp Leu Asp Glu
145                 150                 155                 160

Pro Lys Val Ser His Leu Cys Thr Met Phe Asp Glu Ile Trp Thr Glu
                165                 170                 175

Leu Pro Gly Gln Glu Val Val Tyr Arg Trp Leu Asp Trp Leu Asn Ser
            180                 185                 190

Ser Ser Trp Ala Cys Ile Ser Leu Asn Asp Asn Ile Ile Leu Ile Ala
        195                 200                 205

Asp Lys Thr Ser Asp Val Gly Asp Ala Arg Ala Ile Ala Arg Arg Leu
    210                 215                 220

Leu Val Asp His Thr Ile Pro Leu Met Gln Ser Tyr Asn Glu Arg Arg
225                 230                 235                 240

Ser His Glu Ile Phe Leu Lys Ser Leu His Lys Cys Arg Ile Cys Leu
                245                 250                 255

Ser Glu Asn Thr Gly Arg Asn Phe Ile Lys Leu Pro Cys His His Leu
            260                 265                 270

Phe Cys Leu Thr Cys Met Lys Ser His Cys Arg Ile His Val Thr Glu
        275                 280                 285

Gly Ser Leu Thr Lys Leu Thr Cys Pro Asp Thr Thr Cys Cys Ser Pro
    290                 295                 300

Leu Pro Pro Ser Val Leu Lys Ser Leu Leu Gly Asp Asp Cys Tyr Lys
305                 310                 315                 320

Arg Trp Glu Ser Phe Ala Leu Gln Lys Leu Leu Asp Thr Met Pro Asp
                325                 330                 335

Leu Val Tyr Cys Pro Arg Cys Asn Ala Ala Cys Leu Glu Asp Asp Asn
            340                 345                 350

Asp Ala Gln Cys Pro Glu Cys Phe Phe Thr Phe Cys Ser Leu Cys Lys
        355                 360                 365

Glu Arg Arg His Val Gly Lys Asp Cys Val Thr Pro Glu Glu Lys Ile
    370                 375                 380

Arg Ile Leu Arg Glu Lys His Gln Lys Tyr Ser Leu Pro Glu Lys Gln
385                 390                 395                 400
```

```
Leu Leu Lys Glu Gln Arg Glu Ile Asp Glu Leu Ile Ser Val Cys Glu
                405                 410                 415

Ala Leu Arg Asp Ser Lys Gln Cys Pro Ser Cys Lys Met Ala Ile Ser
            420                 425                 430

Lys Thr Glu Gly Cys Asn Lys Met Ile Cys Arg Asn Cys Gly Lys Phe
        435                 440                 445

Phe Cys Tyr Arg Cys Asn Gln Ala Ile Arg Gly Tyr Glu His Phe Trp
    450                 455                 460

Asp Gly Asn Cys Val Leu Phe Glu His Gln Asn Gln Val Gln Ile Tyr
465                 470                 475                 480

Gly Arg Leu Glu Glu Ser Asp Asp Glu Glu His Phe Asp Asp Glu Asp
                485                 490                 495

Leu Glu Glu Thr Glu Pro Glu Leu Val Trp Gly Cys Pro Cys Pro Val
            500                 505                 510

Cys Gly Arg Trp Asn Gly Lys Leu Asp Thr Asn Asn His Ile Leu Cys
        515                 520                 525

Met Gly Cys Arg Gly His Tyr Cys Ala Leu Cys Arg Arg Arg Val Met
    530                 535                 540

Lys Ser Ser Glu His Tyr Gly Pro Arg Gly Cys Gln Gln His Thr Asp
545                 550                 555                 560

Pro
```

<210> SEQ ID NO 67
<211> LENGTH: 1809
<212> TYPE: DNA
<213> ORGANISM: Sorghum bicolor

<400> SEQUENCE: 67

```
atgtcgagcg gagcctcgtc atcgtcctcg ccgccgccgg cagagtctgg ggacggatac      60

tgggaggcgc gggaggaagc ggcggcgcgg ctggaggcga tggccgcgag ggctcgtggg     120

gaggacgagc tctcggcgga gcagttggag accaacaacc ggctccagga ggacgaggtt     180

gattatataa aactaaaaac gcttttctac aaaacacctg aggtcacgtg tgggcatgcg     240

gaggagccac agatgcctgg atgttctagt gcgagcaaac tcgaggtgct ggcactgcaa     300

gccatttatg gggatgacat ggtgatcttg gaggataagg catgtctacg ttcttttcag     360

ctttttgttc ggtatccaat tcctaatggc actaaggtgt tcttgaatct tcatccaaat     420

ggaactatgg ttggaactga taatgatggg agccaagatg gtagtgaact cttttatgct     480

tgcagcttaa agcatttgcc acctgtggtg ttaacttgtt tgctgccatg ttcatatccc     540

agtacaagtg ctccttattt tactatctca gccaagtggt tggatgaacc caaagtttca     600

cacctctgtg ccatgcttga tgagatttgg actgacctgc caggacaaga agtagtgtat     660

agatggctgg actggctgaa tagctcttca tggccttgca tttctttgaa tgacaacata     720

atactagtcc cagataaaac ttcagatgtt ggagatgaac gtgctattgc aagaaggctt     780

ctagttgatt ctactattcc tctgatgcaa agttacaatg agaggaggtc tcatgaaata     840

tttctgaaaa gctttcatga gtgtggaatt tgtcttagtg aaaatactgg cagaaatttc     900

atcaagctcc catgccacca tttgttttgc ttgacatgta tgaagtctca ctgcagaatt     960

cacgtaacag aagggaattt aacccagctg acatgccctg atacaacttg ccgcagccca    1020

ctcccaccat cagttttgaa aatccttctg ggagatgatt gctataagcg atgggaatcg    1080

ttcacattac agaaactctt agatacaatg cctgatctgg tatattgtcc aaggtgtgat    1140

gctgcctgct tggaggttga caatgatgct caatgccctg aatgtttttt caccttctgc    1200
```

```
tctttgtgca aagaacgccg gcatgtgggg gagcattgtg ttactccaga agaaaagatt   1260

aggattttga gggaaaaaca ccagaaatac tccctcccag aaaaacaatt gttgagagaa   1320

cagagggaaa tagatgaatt agtaaatgtc tgtgaagcgc ttcgcgattc taagcaatgt   1380

cccagatgta aaatggctat ctcgaaaact gaaggttgca acaagatgac ctgtaggaac   1440

tgtgggaaat tcttctgtta tcgttgtaac caggcaattc atggatatga acatttttgg   1500

gatggaaatt gtgtgctgtt tgaacatcac aatcaagtgg gaagaagata tggactgttt   1560

gaggaattgg atgacgatga aggttctgat gatgaagatc tagaggagcc agagccagag   1620

ccagagcctg aaatggtatg gggtcatcca tgtccaatgt gtggccggcg gaatgaaaag   1680

tttggcacaa acaatcatat attgtgcatg ggttgccgag gccactattg cgcgttatgc   1740

cggaagaggg ttacaaaaag ctcggaacac tatggaccaa gaggttgcca acaacacacg   1800

gatccctag                                                           1809
```

<210> SEQ ID NO 68
<211> LENGTH: 602
<212> TYPE: PRT
<213> ORGANISM: Sorghum bicolor

<400> SEQUENCE: 68

```
Met Ser Ser Gly Ala Ser Ser Ser Ser Ser Pro Pro Pro Ala Glu Ser
1               5                   10                  15

Gly Asp Gly Tyr Trp Glu Ala Arg Glu Glu Ala Ala Ala Arg Leu Glu
            20                  25                  30

Ala Met Ala Ala Arg Ala Arg Gly Glu Asp Glu Leu Ser Ala Glu Gln
        35                  40                  45

Leu Glu Thr Asn Asn Arg Leu Gln Glu Asp Glu Val Asp Tyr Ile Lys
    50                  55                  60

Leu Lys Thr Leu Phe Tyr Lys Thr Pro Glu Val Thr Cys Gly His Ala
65                  70                  75                  80

Glu Glu Pro Gln Met Pro Gly Cys Ser Ser Ala Ser Lys Leu Glu Val
                85                  90                  95

Leu Ala Leu Gln Ala Ile Tyr Gly Asp Asp Met Val Ile Leu Glu Asp
            100                 105                 110

Lys Ala Cys Leu Arg Ser Phe Gln Leu Phe Val Arg Tyr Pro Ile Pro
        115                 120                 125

Asn Gly Thr Lys Val Phe Leu Asn Leu His Pro Asn Gly Thr Met Val
    130                 135                 140

Gly Thr Asp Asn Asp Gly Ser Gln Asp Gly Ser Glu Leu Phe Tyr Ala
145                 150                 155                 160

Cys Ser Leu Lys His Leu Pro Pro Val Val Leu Thr Cys Leu Leu Pro
                165                 170                 175

Cys Ser Tyr Pro Ser Thr Ser Ala Pro Tyr Phe Thr Ile Ser Ala Lys
            180                 185                 190

Trp Leu Asp Glu Pro Lys Val Ser His Leu Cys Ala Met Leu Asp Glu
        195                 200                 205

Ile Trp Thr Asp Leu Pro Gly Gln Glu Val Val Tyr Arg Trp Leu Asp
    210                 215                 220

Trp Leu Asn Ser Ser Ser Trp Pro Cys Ile Ser Leu Asn Asp Asn Ile
225                 230                 235                 240

Ile Leu Val Pro Asp Lys Thr Ser Asp Val Gly Asp Glu Arg Ala Ile
                245                 250                 255
```

```
Ala Arg Arg Leu Leu Val Asp Ser Thr Ile Pro Leu Met Gln Ser Tyr
            260                 265                 270

Asn Glu Arg Arg Ser His Glu Ile Phe Leu Lys Ser Phe His Glu Cys
        275                 280                 285

Gly Ile Cys Leu Ser Glu Asn Thr Gly Arg Asn Phe Ile Lys Leu Pro
    290                 295                 300

Cys His His Leu Phe Cys Leu Thr Cys Met Lys Ser His Cys Arg Ile
305                 310                 315                 320

His Val Thr Glu Gly Asn Leu Thr Gln Leu Thr Cys Pro Asp Thr Thr
                325                 330                 335

Cys Arg Ser Pro Leu Pro Pro Ser Val Leu Lys Ile Leu Leu Gly Asp
            340                 345                 350

Asp Cys Tyr Lys Arg Trp Glu Ser Phe Thr Leu Gln Lys Leu Leu Asp
        355                 360                 365

Thr Met Pro Asp Leu Val Tyr Cys Pro Arg Cys Asp Ala Ala Cys Leu
    370                 375                 380

Glu Val Asp Asn Asp Ala Gln Cys Pro Glu Cys Phe Phe Thr Phe Cys
385                 390                 395                 400

Ser Leu Cys Lys Glu Arg Arg His Val Gly Glu His Cys Val Thr Pro
                405                 410                 415

Glu Glu Lys Ile Arg Ile Leu Arg Glu Lys His Gln Lys Tyr Ser Leu
            420                 425                 430

Pro Glu Lys Gln Leu Leu Arg Glu Gln Arg Glu Ile Asp Glu Leu Val
        435                 440                 445

Asn Val Cys Glu Ala Leu Arg Asp Ser Lys Gln Cys Pro Arg Cys Lys
    450                 455                 460

Met Ala Ile Ser Lys Thr Glu Gly Cys Asn Lys Met Thr Cys Arg Asn
465                 470                 475                 480

Cys Gly Lys Phe Phe Cys Tyr Arg Cys Asn Gln Ala Ile His Gly Tyr
                485                 490                 495

Glu His Phe Trp Asp Gly Asn Cys Val Leu Phe Glu His His Asn Gln
            500                 505                 510

Val Gly Arg Arg Tyr Gly Leu Phe Glu Glu Leu Asp Asp Asp Glu Gly
        515                 520                 525

Ser Asp Asp Glu Asp Leu Glu Glu Pro Glu Pro Glu Pro Glu Pro Glu
    530                 535                 540

Met Val Trp Gly His Pro Cys Pro Met Cys Gly Arg Arg Asn Glu Lys
545                 550                 555                 560

Phe Gly Thr Asn Asn His Ile Leu Cys Met Gly Cys Arg Gly His Tyr
                565                 570                 575

Cys Ala Leu Cys Arg Lys Arg Val Thr Lys Ser Ser Glu His Tyr Gly
            580                 585                 590

Pro Arg Gly Cys Gln Gln His Thr Asp Pro
        595                 600
```

<210> SEQ ID NO 69
<211> LENGTH: 2067
<212> TYPE: DNA
<213> ORGANISM: Arabidopsis thaliana

<400> SEQUENCE: 69

```
atgagaggaa cacacggagg cagtggaaga aatcacgacc gccgctacat ccgccgtgac      60

gctgggattg tgaatccagt caacgatcat ccaaaatcag agcatcagaa agaagacacg     120

acttcgacgg atttatcatc tgcagcagct tttccgtcta cttctcagcc aatccaaaac     180
```

```
ctcgatcatt ctacaaaacc ttcaaagtct caccggaatc gacgcagccg tggatcaaat    240

tcaaaacctc gtcccgtgga gaaaccggag gtgaattttg ctgaatccga tgttgttgat    300

tgcttggctg atgaattgag taggttaaag gtgaaacaga attcgcattc ggtgaatatg    360

gaggagaagt ttcatcacag ttctagtgat cattcgaatt gtgaggaatc ggagttaaag    420

agagctgaaa gtgaagaaat tgctgatggt gttgatgaat atgagacgaa ggaagatatt    480

atgttgacaa ttctgaaaga tttgcgatct agtgtcagtg agccagagct aacagaggag    540

caactaaaga tgaatgatca attacaggaa gatgagcttt tggcattggg gtacatatat    600

ggaggaaaca tgttcatctt tgatcggtat aacgatatgc gatactttca ggttcatgta    660

aacgttgaag ctactagtga atatactatc tctacaaagc ttaacttaca agctgattca    720

agcaaagagt cagaggattt cttgtactct ttcaaggcgc aacaccttcc accgattgtg    780

ttgaaatgtt tattaccaaa agcttatccg agccacttac cgccttattt cttaataagt    840

gttcagtgga tgaatcctga taagatttca agtctctgct ctaagctgga ctcgttatgg    900

agtgaacagc cagggcaaga agtcttgtac cagtggacag attggctaca gaactcgtcg    960

atttctcatc ttggttttga taatgagatt gttcttggtc cttatggtgt tacatgttcc   1020

agagataagc gtgctgtgtc tggaagtcgt tctccggatt cagatattcc ttatattagg   1080

agttatgacg atgagaaacg tcatgatagc ttccttcaga gcttgcatga gtgctgcata   1140

tgcttctctg aatctgcagg tatcgacttt gttaagttac catgccagca tttcttttgt   1200

ttgaaatgta tgaagaccta tacagacata catgtcactg aaggcacagt taacaagctc   1260

aagtgtccgg actcgaaatg tggagaaact gttccgccag ggatattgaa gagattgttg   1320

ggcgatgaag cgtatgaacg gtgggaaact cttatgttac agaaaacact ggaatccatg   1380

actgacgttg cttactgtcc tagatgtgaa accccttgca tagaggacga ggaacagctt   1440

gctttatgct tcaaatgcta cttcagtttc tgtacacttt gtaaggaaaa gagacatgtg   1500

ggtgtggctt gcatgagccc ggaacttagg cttcaaatct tgcaggagcg tcaagattct   1560

tctcgtcttg gagaggaaca aaggcggaaa gagaaagaaa tgatcaatga gattatgagt   1620

gtgaaggtga taatgaaaag cgctaaacaa tgtccgtcgt gcaaaatagc catctcaaga   1680

accggaggtt gtaacaaaat ggtatgcaat aactgtggtc aatacttttg ttaccgttgc   1740

aacgaagcta tcactggtta tgaacatttc agtgagggaa aatgtgaact gttcccacaa   1800

gaggcgatcc aagaatggaa tgagatgatg aatgagagac aagtcattgg acagattcaa   1860

gcgcaactgt ttgcacaagg cggtcagttt ccacagcgcg gtcagttatg tcctaattgc   1920

cgccagttca atggaaaggc gggaaacaac aatcacttgt tttgttgggc atgtcaagca   1980

catttctgtt atctttgtaa gaaagtggtg aagaaatctg ctcagcatta tggaccaaag   2040

ggctgcaagc agcacacaga tgggtaa                                        2067
```

<210> SEQ ID NO 70
<211> LENGTH: 688
<212> TYPE: PRT
<213> ORGANISM: Arabidopsis thaliana

<400> SEQUENCE: 70

```
Met Arg Gly Thr His Gly Gly Ser Gly Arg Asn His Asp Arg Arg Tyr
1               5                   10                  15

Ile Arg Arg Asp Ala Gly Ile Val Asn Pro Val Asn Asp His Pro Lys
            20                  25                  30
```

```
Ser Glu His Gln Lys Glu Asp Thr Thr Ser Thr Asp Leu Ser Ser Ala
        35                  40                  45

Ala Ala Phe Pro Ser Thr Ser Gln Pro Ile Gln Asn Leu Asp His Ser
    50                  55                  60

Thr Lys Pro Ser Lys Ser His Arg Asn Arg Arg Ser Arg Gly Ser Asn
65                  70                  75                  80

Ser Lys Pro Arg Pro Val Glu Lys Pro Glu Val Asn Phe Ala Glu Ser
                85                  90                  95

Asp Val Val Asp Cys Leu Ala Asp Glu Leu Ser Arg Leu Lys Val Lys
            100                 105                 110

Gln Asn Ser His Ser Val Asn Met Glu Glu Lys Phe His His Ser Ser
        115                 120                 125

Ser Asp His Ser Asn Cys Glu Glu Ser Glu Leu Lys Arg Ala Glu Ser
    130                 135                 140

Glu Glu Ile Ala Asp Gly Val Asp Glu Tyr Glu Thr Lys Glu Asp Ile
145                 150                 155                 160

Met Leu Thr Ile Leu Lys Asp Leu Arg Ser Ser Val Ser Glu Pro Glu
                165                 170                 175

Leu Thr Glu Glu Gln Leu Lys Met Asn Asp Gln Leu Gln Glu Asp Glu
            180                 185                 190

Leu Leu Ala Leu Gly Tyr Ile Tyr Gly Gly Asn Met Phe Ile Phe Asp
        195                 200                 205

Arg Tyr Asn Asp Met Arg Tyr Phe Gln Val His Val Asn Val Glu Ala
    210                 215                 220

Thr Ser Glu Tyr Thr Ile Ser Thr Lys Leu Asn Leu Gln Ala Asp Ser
225                 230                 235                 240

Ser Lys Glu Ser Glu Asp Phe Leu Tyr Ser Phe Lys Ala Gln His Leu
                245                 250                 255

Pro Pro Ile Val Leu Lys Cys Leu Leu Pro Lys Ala Tyr Pro Ser His
            260                 265                 270

Leu Pro Pro Tyr Phe Leu Ile Ser Val Gln Trp Met Asn Pro Asp Lys
        275                 280                 285

Ile Ser Ser Leu Cys Ser Lys Leu Asp Ser Leu Trp Ser Glu Gln Pro
    290                 295                 300

Gly Gln Glu Val Leu Tyr Gln Trp Thr Asp Trp Leu Gln Asn Ser Ser
305                 310                 315                 320

Ile Ser His Leu Gly Phe Asp Asn Glu Ile Val Leu Gly Pro Tyr Gly
                325                 330                 335

Val Thr Cys Ser Arg Asp Lys Arg Ala Val Ser Gly Ser Arg Ser Pro
            340                 345                 350

Asp Ser Asp Ile Pro Tyr Ile Arg Ser Tyr Asp Asp Glu Lys Arg His
        355                 360                 365

Asp Ser Phe Leu Gln Ser Leu His Glu Cys Cys Ile Cys Phe Ser Glu
    370                 375                 380

Ser Ala Gly Ile Asp Phe Val Lys Leu Pro Cys Gln His Phe Phe Cys
385                 390                 395                 400

Leu Lys Cys Met Lys Thr Tyr Thr Asp Ile His Val Thr Glu Gly Thr
                405                 410                 415

Val Asn Lys Leu Lys Cys Pro Asp Ser Lys Cys Gly Glu Thr Val Pro
            420                 425                 430

Pro Gly Ile Leu Lys Arg Leu Leu Gly Asp Glu Ala Tyr Glu Arg Trp
        435                 440                 445

Glu Thr Leu Met Leu Gln Lys Thr Leu Glu Ser Met Thr Asp Val Ala
```

```
    450                 455                 460

Tyr Cys Pro Arg Cys Glu Thr Pro Cys Ile Glu Asp Glu Glu Gln Leu
465                 470                 475                 480

Ala Leu Cys Phe Lys Cys Tyr Phe Ser Phe Cys Thr Leu Cys Lys Glu
                485                 490                 495

Lys Arg His Val Gly Val Ala Cys Met Ser Pro Glu Leu Arg Leu Gln
            500                 505                 510

Ile Leu Gln Glu Arg Gln Asp Ser Ser Arg Leu Gly Glu Glu Gln Arg
        515                 520                 525

Arg Lys Glu Lys Glu Met Ile Asn Glu Ile Met Ser Val Lys Val Ile
    530                 535                 540

Met Lys Ser Ala Lys Gln Cys Pro Ser Cys Lys Ile Ala Ile Ser Arg
545                 550                 555                 560

Thr Gly Gly Cys Asn Lys Met Val Cys Asn Asn Cys Gly Gln Tyr Phe
                565                 570                 575

Cys Tyr Arg Cys Asn Glu Ala Ile Thr Gly Tyr Glu His Phe Ser Glu
            580                 585                 590

Gly Lys Cys Glu Leu Phe Pro Gln Glu Ala Ile Gln Glu Trp Asn Glu
        595                 600                 605

Met Met Asn Glu Arg Gln Val Ile Gly Gln Ile Gln Ala Gln Leu Phe
    610                 615                 620

Ala Gln Gly Gly Gln Phe Pro Gln Arg Gly Gln Leu Cys Pro Asn Cys
625                 630                 635                 640

Arg Gln Phe Asn Gly Lys Ala Gly Asn Asn Asn His Leu Phe Cys Trp
                645                 650                 655

Ala Cys Gln Ala His Phe Cys Tyr Leu Cys Lys Lys Val Val Lys Lys
            660                 665                 670

Ser Ala Gln His Tyr Gly Pro Lys Gly Cys Lys Gln His Thr Asp Gly
        675                 680                 685
```

<210> SEQ ID NO 71
<211> LENGTH: 1050
<212> TYPE: DNA
<213> ORGANISM: Glycine max

<400> SEQUENCE: 71

```
atgaattatg tccaggatga gcgtgttatt tcaggagctg aatgcattga tgttgatatt     60

cctttttttac gaagttacaa cgatgagaga cacaatgaga acttcctcaa agaattgcat    120

gattgtaaca tttgctttag tgaatatgca ggctctcagt tcatccggtt accatgtgag    180

catttttttt gcctcaaatg cttgcagacc tttgcccaga tacatgtaaa ggaaggcact    240

gttagtaatc ttaaatgtcc tgaagcaaaa tgtgcaatta tgattcctcc tggcctttta    300

aaacaattgc tggatgacac agattatgag cgctgggaat ccatgatgtt ggaaaaaaca    360

cttgcatcaa tgtctgatgt tgtttattgt ccaaggtgtg aaacaccctg catagaggat    420

gaagaccagc atgctcaatg cccaaaatgt tactttagct tttgtaccct ttgcagggaa    480

cgacgccatg ttggcatagc atgcatgagt ctagatatga agcttcagat tttgcaggac    540

cgtcaaaatt tgtctcaatt aaaggaagat caaaagcgaa gggaacgtga aaagatcaat    600

gaaatgctca atatgaaaga aattcatcgt gattccaagc tgtgcccttc ttgtgacatg    660

gcaatttctc gaactgaagg ttgtaacaaa atgaaatgtg gtaactgtga acaatacttc    720

tgttaccgct gcaacaaagc aattgatgca tcagatccat atggacattt cagggatggt    780

tcatgtgaat tgttcccacg agaaatggtt gattcctggg aagagcgcat taatcatcgc    840
```

```
caggcggtag gacaactaca ggctgagctc tttcctcaac atggcttggc gtgtcctagt    900

tgtcgtcaat ataatccaaa gattggaaat aataatcact tgttttgctg ggcatgccaa    960

cgccattact gctacttatg caaagcgatt gtcaggcgtg gcactaagca ttatggacca   1020

aagggctgca aacagcactc tgagggatag                                    1050


<210> SEQ ID NO 72
<211> LENGTH: 349
<212> TYPE: PRT
<213> ORGANISM: Glycine max

<400> SEQUENCE: 72

Met Asn Tyr Val Gln Asp Glu Arg Val Ile Ser Gly Ala Glu Cys Ile
1               5                   10                  15

Asp Val Asp Ile Pro Phe Leu Arg Ser Tyr Asn Asp Glu Arg His Asn
            20                  25                  30

Glu Asn Phe Leu Lys Glu Leu His Asp Cys Asn Ile Cys Phe Ser Glu
        35                  40                  45

Tyr Ala Gly Ser Gln Phe Ile Arg Leu Pro Cys Glu His Phe Phe Cys
    50                  55                  60

Leu Lys Cys Leu Gln Thr Phe Ala Gln Ile His Val Lys Glu Gly Thr
65                  70                  75                  80

Val Ser Asn Leu Lys Cys Pro Glu Ala Lys Cys Ala Ile Met Ile Pro
                85                  90                  95

Pro Gly Leu Leu Lys Gln Leu Leu Asp Asp Thr Asp Tyr Glu Arg Trp
            100                 105                 110

Glu Ser Met Met Leu Glu Lys Thr Leu Ala Ser Met Ser Asp Val Val
        115                 120                 125

Tyr Cys Pro Arg Cys Glu Thr Pro Cys Ile Glu Asp Glu Asp Gln His
    130                 135                 140

Ala Gln Cys Pro Lys Cys Tyr Phe Ser Phe Cys Thr Leu Cys Arg Glu
145                 150                 155                 160

Arg Arg His Val Gly Ile Ala Cys Met Ser Leu Asp Met Lys Leu Gln
                165                 170                 175

Ile Leu Gln Asp Arg Gln Asn Leu Ser Gln Leu Lys Glu Asp Gln Lys
            180                 185                 190

Arg Arg Glu Arg Glu Lys Ile Asn Glu Met Leu Asn Met Lys Glu Ile
        195                 200                 205

His Arg Asp Ser Lys Leu Cys Pro Ser Cys Asp Met Ala Ile Ser Arg
    210                 215                 220

Thr Glu Gly Cys Asn Lys Met Lys Cys Gly Asn Cys Glu Gln Tyr Phe
225                 230                 235                 240

Cys Tyr Arg Cys Asn Lys Ala Ile Asp Ala Ser Asp Pro Tyr Gly His
                245                 250                 255

Phe Arg Asp Gly Ser Cys Glu Leu Phe Pro Arg Glu Met Val Asp Ser
            260                 265                 270

Trp Glu Glu Arg Ile Asn His Arg Gln Ala Val Gly Gln Leu Gln Ala
        275                 280                 285

Glu Leu Phe Pro Gln His Gly Leu Ala Cys Pro Ser Cys Arg Gln Tyr
    290                 295                 300

Asn Pro Lys Ile Gly Asn Asn Asn His Leu Phe Cys Trp Ala Cys Gln
305                 310                 315                 320

Arg His Tyr Cys Tyr Leu Cys Lys Ala Ile Val Arg Arg Gly Thr Lys
                325                 330                 335
```

```
His Tyr Gly Pro Lys Gly Cys Lys Gln His Ser Glu Gly
            340                 345


<210> SEQ ID NO 73
<211> LENGTH: 303
<212> TYPE: DNA
<213> ORGANISM: Oryza sativa

<400> SEQUENCE: 73

atgtcggccg ccggggagga ggacaagaag ccggcggggg gagagggcgg cggcgcccac      60

atcaacctca aggtcaaggg acaggatggg aacgaggtat tcttccgcat caagagatct     120

acgcagctga agaagctgat gaacgcctat tgtgaccgtc agtctgtgga tatgaatgct     180

attgcattcc tatttgatgg tcgtaggctc cgtggcgagc agacccctga cgagctcgag     240

atggaagacg ggacgagat cgacgccatg ctccaccaga ctggaggctg cctgcctgcc     300

tag                                                                   303


<210> SEQ ID NO 74
<211> LENGTH: 100
<212> TYPE: PRT
<213> ORGANISM: Oryza sativa

<400> SEQUENCE: 74

Met Ser Ala Ala Gly Glu Glu Asp Lys Lys Pro Ala Gly Gly Glu Gly
1               5                   10                  15

Gly Gly Ala His Ile Asn Leu Lys Val Lys Gly Gln Asp Gly Asn Glu
            20                  25                  30

Val Phe Phe Arg Ile Lys Arg Ser Thr Gln Leu Lys Lys Leu Met Asn
        35                  40                  45

Ala Tyr Cys Asp Arg Gln Ser Val Asp Met Asn Ala Ile Ala Phe Leu
    50                  55                  60

Phe Asp Gly Arg Arg Leu Arg Gly Glu Gln Thr Pro Asp Glu Leu Glu
65                  70                  75                  80

Met Glu Asp Gly Asp Glu Ile Asp Ala Met Leu His Gln Thr Gly Gly
                85                  90                  95

Cys Leu Pro Ala
            100


<210> SEQ ID NO 75
<211> LENGTH: 300
<212> TYPE: DNA
<213> ORGANISM: Zea mays

<400> SEQUENCE: 75

atgtctggag ccggcgagga ggacaagaag cccgcggagg gcggcgccca catcaacctt      60

aaggtcaagg gacaggatgg caatgaggtg ttctttcgca taaagaggtc cacccagctg     120

aagaagctga tgaacgctta ttgtgaccgc cagtctgtgg acatgaatgc cattgcgttc     180

ctgtttgatg gccgcaggct tcgcggcgag cagacccctg atgagctgga gatggaggac     240

ggcgacgaga tcgatgccat gcttcaccag accggaggca gcgttcctag caccacctaa     300


<210> SEQ ID NO 76
<211> LENGTH: 99
<212> TYPE: PRT
<213> ORGANISM: Zea mays

<400> SEQUENCE: 76
```

```
Met Ser Gly Ala Gly Glu Glu Asp Lys Lys Pro Ala Glu Gly Gly Ala
1               5                   10                  15

His Ile Asn Leu Lys Val Lys Gly Gln Asp Gly Asn Glu Val Phe Phe
            20                  25                  30

Arg Ile Lys Arg Ser Thr Gln Leu Lys Lys Leu Met Asn Ala Tyr Cys
        35                  40                  45

Asp Arg Gln Ser Val Asp Met Asn Ala Ile Ala Phe Leu Phe Asp Gly
    50                  55                  60

Arg Arg Leu Arg Gly Glu Gln Thr Pro Asp Glu Leu Glu Met Glu Asp
65                  70                  75                  80

Gly Asp Glu Ile Asp Ala Met Leu His Gln Thr Gly Gly Ser Val Pro
                85                  90                  95

Ser Thr Thr


<210> SEQ ID NO 77
<211> LENGTH: 300
<212> TYPE: DNA
<213> ORGANISM: Sorghum bicolor

<400> SEQUENCE: 77

atgtctggag ccggtgagga ggacaagaag cccgcggagg cgggcggcgc ccacatcaat      60

ctcaaggtca agggacagga tggcaatgag gttttcttcc gcattaagag gtccacccag     120

ctgaagaagc tgatgaacgc ctactgtgac cgccagtctg tggatatgaa tgccattgca     180

ttcctgtttg atggccgcag gcttcgcggc gagcagaccc cggatgagct ggagatggaa     240

gacggcgatg agattgacgc catgcttcac cagactggag gcagcgttcc tggcgcctag     300


<210> SEQ ID NO 78
<211> LENGTH: 99
<212> TYPE: PRT
<213> ORGANISM: Sorghum bicolor

<400> SEQUENCE: 78

Met Ser Gly Ala Gly Glu Glu Asp Lys Lys Pro Ala Glu Ala Gly Gly
1               5                   10                  15

Ala His Ile Asn Leu Lys Val Lys Gly Gln Asp Gly Asn Glu Val Phe
            20                  25                  30

Phe Arg Ile Lys Arg Ser Thr Gln Leu Lys Lys Leu Met Asn Ala Tyr
        35                  40                  45

Cys Asp Arg Gln Ser Val Asp Met Asn Ala Ile Ala Phe Leu Phe Asp
    50                  55                  60

Gly Arg Arg Leu Arg Gly Glu Gln Thr Pro Asp Glu Leu Glu Met Glu
65                  70                  75                  80

Asp Gly Asp Glu Ile Asp Ala Met Leu His Gln Thr Gly Gly Ser Val
                85                  90                  95

Pro Gly Ala


<210> SEQ ID NO 79
<211> LENGTH: 303
<212> TYPE: DNA
<213> ORGANISM: Arabidopsis thaliana

<400> SEQUENCE: 79

atgtctgcaa accaggagga agacaagaag ccaggagacg gaggagctca catcaatctc      60

aaagtcaagg gacaggatgg aaacgaggtt ttctttagga tcaagagaag cactcagctc     120

aagaagctga tgaatgctta ctgtgaccgg caatctgtgg acatgaactc cattgctttc     180
```

```
ttgtttgatg ggcgtcgtct tcgtgctgag caaactcccg atgagcttga catggaggat    240

ggtgatgaga tcgatgcgat gctccatcag actggtggca gcggtggtgg tgctacggcc    300

tga                                                                   303


<210> SEQ ID NO 80
<211> LENGTH: 100
<212> TYPE: PRT
<213> ORGANISM: Arabidopsis thaliana

<400> SEQUENCE: 80

Met Ser Ala Asn Gln Glu Glu Asp Lys Lys Pro Gly Asp Gly Gly Ala
1               5                   10                  15

His Ile Asn Leu Lys Val Lys Gly Gln Asp Gly Asn Glu Val Phe Phe
            20                  25                  30

Arg Ile Lys Arg Ser Thr Gln Leu Lys Lys Leu Met Asn Ala Tyr Cys
        35                  40                  45

Asp Arg Gln Ser Val Asp Met Asn Ser Ile Ala Phe Leu Phe Asp Gly
    50                  55                  60

Arg Arg Leu Arg Ala Glu Gln Thr Pro Asp Glu Leu Asp Met Glu Asp
65                  70                  75                  80

Gly Asp Glu Ile Asp Ala Met Leu His Gln Thr Gly Gly Ser Gly Gly
                85                  90                  95

Gly Ala Thr Ala
            100


<210> SEQ ID NO 81
<211> LENGTH: 300
<212> TYPE: DNA
<213> ORGANISM: Glycine max

<400> SEQUENCE: 81

atgtcgggcg ttaccaacaa caacgaggaa gacaagaagc caaccgaaca gggagcacac     60

atcaacctta aggttaaggg gcaggatggg aatgaagttt ttttcaggat caagagaagc    120

actcaattga agaagcttat gaatgcttac tgtgaccgac agtcggtgga tttcaactcc    180

attgcttttc tgtttgatgg acgccgcctc cgagctgagc agactccaga tgagttggaa    240

atggaggacg gggacgagat tgatgccatg cttcaccaga caggaggttc tgttgtctga    300


<210> SEQ ID NO 82
<211> LENGTH: 99
<212> TYPE: PRT
<213> ORGANISM: Glycine max

<400> SEQUENCE: 82

Met Ser Gly Val Thr Asn Asn Asn Glu Glu Asp Lys Lys Pro Thr Glu
1               5                   10                  15

Gln Gly Ala His Ile Asn Leu Lys Val Lys Gly Gln Asp Gly Asn Glu
            20                  25                  30

Val Phe Phe Arg Ile Lys Arg Ser Thr Gln Leu Lys Lys Leu Met Asn
        35                  40                  45

Ala Tyr Cys Asp Arg Gln Ser Val Asp Phe Asn Ser Ile Ala Phe Leu
    50                  55                  60

Phe Asp Gly Arg Arg Leu Arg Ala Glu Gln Thr Pro Asp Glu Leu Glu
65                  70                  75                  80

Met Glu Asp Gly Asp Glu Ile Asp Ala Met Leu His Gln Thr Gly Gly
                85                  90                  95
```

Ser Val Val

<210> SEQ ID NO 83
<211> LENGTH: 2154
<212> TYPE: DNA
<213> ORGANISM: Oryza sativa

<400> SEQUENCE: 83
atggcggacg ccgccgccgc cgccgccggc ggcggaggca gccaccgttc cgtccaccat 60
gcgcacctcg cggcgctgct caacccctcc ccgcgctcgc cgccgcaccc gcacccgctc 120
cagctccacc ggcgccacct cccgctgtcc cttcccgcgg cccgccgcct cgccgcggcc 180
ttcccgccgc tcccgctcct cctctccctc ctcgccgcgc tccgcctcct cccctcgccg 240
ccgccgccgc gcccccttcga cgcgctcatc aggtcgtacg cctccctccc tcgcccctcc 300
ctcgccgccg cggcgctcgc gttcgccgcg tcggccgggt acgccccctc cgtcccggcc 360
tacaacgccg tcctcctcgc gctctccgac gcctcgctcc cctccgcccg ccgcttcctc 420
tcctccatgc tccgccacgg cgtggcgccc aacgtgtaca cctacaacat cctcgtccgc 480
gcgctctgcg cccgcggccg cctggaggag gcggtcggcg tcgtgggcga catgcgtggc 540
gcgggctgcg cgcccaacgc cgtcacctac aacacgctcg tcgcggcgtt ctgcagggcc 600
ggggagttgg acggcgcgga gagggtggtc agcttgatga gggaggaggg caatgcgaag 660
ccgaatctgg tgaccttcaa ctcgatggtg aatgggctgt gtaaagcggg gaggatggag 720
ggtgcacgca aggtgttcga tgaaatggtg agggaggggt tggcaccgga tgtggtcagc 780
tacaacacct tgttaagtgg ttactgcaag gtgggttgct tacatgagtc attggcggtg 840
ttttcagaga tgacacagag agggcttgtg ccagatgtcg tgacgtttac gtcgctaatc 900
catgcaacat gtaaggctgg taacttggag caggcagtgg ctctggtggc gcagatgagg 960
gagaggggcc ttcggatgaa cgaggtcact ttcacggcac ttattgatgg tttctgcaag 1020
aaggggttct tggatgatgc attgcttgca gttgaggaga tgaggaaatg tgggatccag 1080
ccttcagtgg tatgttacaa tgcacttatt aatgggtact gcaagttagg aagaatggat 1140
ctagcaagag agctaatccg tgaaatggag gctaaaagag tgaaacccga tgttgtgacc 1200
tatagtacga ttatcagcgg atactgtaag gttggcaatt tggattctgc attccaattg 1260
aatcagaaaa tgctcaaaaa gggtgtgctt ccagatgcaa tcacctactc atcactcata 1320
aggggtcttt gtgaagagaa aaggctcaat gatgcttgtg agctatttga gaacatgctt 1380
caacttggtg tgcaacctga cgaatttact tatacaacac tcattgatgg ccactgcaag 1440
gaaggaaatg ttgagaaggc tctttctctg catgatgaga tgataaggaa gggagttctc 1500
cctgatgttg tgacgtacag tgtgctcata aatgggctta gcaagtcagc acgtacaaag 1560
gaggcacatc ggttactctt taaactgtat catgaagatc cggttccaga caatattaag 1620
tatgatgctc tgatgctttg ttgcagcaaa gctgagttta agagtgtagt ggccctcctg 1680
aagggatttt gcatgaaagg cttgatgaag gaagctgata aagtatacca gtcgatgttg 1740
gacagaaact ggaagcttga tgggtctgtg tacagtatac ttattcatgg gcattgcagg 1800
ggaggaaatg ttaggaaggc tctcagcttt cataaacaaa tgttgcggag tgggttttcc 1860
cctaattcaa caagcaccat ttcattggtt aggggtttat ttgaagaggg gatggttgtg 1920
gaagcagata atgccattca ggacttactg acttgttgtc cactagcaga tgcagaagca 1980
tcaaaggctc ttattgacct caatcggaag gaagggatgg actacttcca agctcagggt 2040

```
gaaatctggt attcagaatc ctccccctct gtggaatact ggaattacat gatgaccata   2100

tgtcactttg gagtttggag cacttatttt tccatgcttc gcttaacaaa atga         2154


<210> SEQ ID NO 84
<211> LENGTH: 717
<212> TYPE: PRT
<213> ORGANISM: Oryza sativa

<400> SEQUENCE: 84

Met Ala Asp Ala Ala Ala Ala Ala Ala Gly Gly Gly Gly Ser His Arg
1               5                   10                  15

Ser Val His His Ala His Leu Ala Ala Leu Leu Asn Pro Ser Pro Arg
            20                  25                  30

Ser Pro Pro His Pro His Pro Leu Gln Leu His Arg Arg His Leu Pro
        35                  40                  45

Leu Ser Leu Pro Ala Ala Arg Arg Leu Ala Ala Ala Phe Pro Pro Leu
    50                  55                  60

Pro Leu Leu Leu Ser Leu Leu Ala Ala Leu Arg Leu Leu Pro Ser Pro
65                  70                  75                  80

Pro Pro Pro Arg Pro Phe Asp Ala Leu Ile Arg Ser Tyr Ala Ser Leu
                85                  90                  95

Pro Arg Pro Ser Leu Ala Ala Ala Ala Leu Ala Phe Ala Ala Ser Ala
            100                 105                 110

Gly Tyr Ala Pro Ser Val Pro Ala Tyr Asn Ala Val Leu Leu Ala Leu
        115                 120                 125

Ser Asp Ala Ser Leu Pro Ser Ala Arg Arg Phe Leu Ser Ser Met Leu
    130                 135                 140

Arg His Gly Val Ala Pro Asn Val Tyr Thr Tyr Asn Ile Leu Val Arg
145                 150                 155                 160

Ala Leu Cys Ala Arg Gly Arg Leu Glu Glu Ala Val Gly Val Val Gly
                165                 170                 175

Asp Met Arg Gly Ala Gly Cys Ala Pro Asn Ala Val Thr Tyr Asn Thr
            180                 185                 190

Leu Val Ala Ala Phe Cys Arg Ala Gly Glu Leu Asp Gly Ala Glu Arg
        195                 200                 205

Val Val Ser Leu Met Arg Glu Glu Gly Asn Ala Lys Pro Asn Leu Val
    210                 215                 220

Thr Phe Asn Ser Met Val Asn Gly Leu Cys Lys Ala Gly Arg Met Glu
225                 230                 235                 240

Gly Ala Arg Lys Val Phe Asp Glu Met Val Arg Glu Gly Leu Ala Pro
                245                 250                 255

Asp Val Val Ser Tyr Asn Thr Leu Leu Ser Gly Tyr Cys Lys Val Gly
            260                 265                 270

Cys Leu His Glu Ser Leu Ala Val Phe Ser Glu Met Thr Gln Arg Gly
        275                 280                 285

Leu Val Pro Asp Val Val Thr Phe Thr Ser Leu Ile His Ala Thr Cys
    290                 295                 300

Lys Ala Gly Asn Leu Glu Gln Ala Val Ala Leu Val Ala Gln Met Arg
305                 310                 315                 320

Glu Arg Gly Leu Arg Met Asn Glu Val Thr Phe Thr Ala Leu Ile Asp
                325                 330                 335

Gly Phe Cys Lys Lys Gly Phe Leu Asp Asp Ala Leu Leu Ala Val Glu
            340                 345                 350

Glu Met Arg Lys Cys Gly Ile Gln Pro Ser Val Val Cys Tyr Asn Ala
```

```
        355                 360                 365

Leu Ile Asn Gly Tyr Cys Lys Leu Gly Arg Met Asp Leu Ala Arg Glu
    370                 375                 380

Leu Ile Arg Glu Met Glu Ala Lys Arg Val Lys Pro Asp Val Val Thr
385                 390                 395                 400

Tyr Ser Thr Ile Ile Ser Gly Tyr Cys Lys Val Gly Asn Leu Asp Ser
                405                 410                 415

Ala Phe Gln Leu Asn Gln Lys Met Leu Lys Lys Gly Val Leu Pro Asp
            420                 425                 430

Ala Ile Thr Tyr Ser Ser Leu Ile Arg Gly Leu Cys Glu Glu Lys Arg
        435                 440                 445

Leu Asn Asp Ala Cys Glu Leu Phe Glu Asn Met Leu Gln Leu Gly Val
    450                 455                 460

Gln Pro Asp Glu Phe Thr Tyr Thr Thr Leu Ile Asp Gly His Cys Lys
465                 470                 475                 480

Glu Gly Asn Val Glu Lys Ala Leu Ser Leu His Asp Glu Met Ile Arg
                485                 490                 495

Lys Gly Val Leu Pro Asp Val Val Thr Tyr Ser Val Leu Ile Asn Gly
            500                 505                 510

Leu Ser Lys Ser Ala Arg Thr Lys Glu Ala His Arg Leu Leu Phe Lys
        515                 520                 525

Leu Tyr His Glu Asp Pro Val Pro Asp Asn Ile Lys Tyr Asp Ala Leu
    530                 535                 540

Met Leu Cys Cys Ser Lys Ala Glu Phe Lys Ser Val Val Ala Leu Leu
545                 550                 555                 560

Lys Gly Phe Cys Met Lys Gly Leu Met Lys Glu Ala Asp Lys Val Tyr
                565                 570                 575

Gln Ser Met Leu Asp Arg Asn Trp Lys Leu Asp Gly Ser Val Tyr Ser
            580                 585                 590

Ile Leu Ile His Gly His Cys Arg Gly Gly Asn Val Arg Lys Ala Leu
        595                 600                 605

Ser Phe His Lys Gln Met Leu Arg Ser Gly Phe Ser Pro Asn Ser Thr
    610                 615                 620

Ser Thr Ile Ser Leu Val Arg Gly Leu Phe Glu Glu Gly Met Val Val
625                 630                 635                 640

Glu Ala Asp Asn Ala Ile Gln Asp Leu Leu Thr Cys Cys Pro Leu Ala
                645                 650                 655

Asp Ala Glu Ala Ser Lys Ala Leu Ile Asp Leu Asn Arg Lys Glu Gly
            660                 665                 670

Met Asp Tyr Phe Gln Ala Gln Gly Glu Ile Trp Tyr Ser Glu Ser Ser
        675                 680                 685

Pro Ser Val Glu Tyr Trp Asn Tyr Met Met Thr Ile Cys His Phe Gly
    690                 695                 700

Val Trp Ser Thr Tyr Phe Ser Met Leu Arg Leu Thr Lys
705                 710                 715


<210> SEQ ID NO 85
<211> LENGTH: 1950
<212> TYPE: DNA
<213> ORGANISM: Zea mays

<400> SEQUENCE: 85

atggcgatcc cccgtcgcct atcttgcctt cccacggttg ccgcggccac caagtggtcg      60

gccgggaatc tcgccataga catcggcaca atcggcgcga gaccctcaac ggcagccctg     120
```

```
gctgccgccg cgacggcggc cgccgccgcc ggccgcgcct cggagtgcca gtccctcctc    180
ctccgcatgt cgcgccgccg cggcgcctct cgacgcgaga tcgtctcttc cctcctcgcc    240
tcgtccccca ctccgcagcc gcaggtgttc gacctcctca tccgcaccta cacccagtcg    300
cggaagcccc gggaggcctt tgaggccttc cgcctcctcc tcgaccaccg cgtccccgtc    360
ccagcctctg cgtccaacgc tctccttgcc gtgctctccc gcgccgggtg gcctcacctc    420
gcccaggagg cctaccgcct cgtcctctcg tctgactcgg aggtaaacgc ctacacgctt    480
aacatcatgg tccacagcta ctgtaaaacc ctagagttcg atggggctga cactgtcatc    540
tccgagatgg agaagagatg cgtgttcccg gatgtggtta cacacaatgt gttgattgat    600
gccagattcc gtgctggaga tgtggatgca gcgatcgcat tggttgattc catggccaat    660
agggggttga agcctgggat tgtgacatac aattcggttt tgaaggggtt gtgtaagcac    720
agaaggtttg ataaggcaaa ggaggtgttc aggacaatgg accagtgcag tgttgcacca    780
gatgttcgga gtttcaatat tttgatcgga ggattttgta gggttgggga ggttaaggag    840
gcagtgaagt tttacaagga gatgcaacat cgttatgtta caccagatgt ggtcagcttt    900
agctgtttga ttggattatt ctcgaggaga ggggagatgg accatgcagg ggcatacttg    960
agggaaatga aggggcttgg attggtgcct gatggtgtga tttacacaat ggtcataggt   1020
gggttttgta gggctggatc aatgtcagag gctctaagag ttagggatga gatggttggc   1080
tttggatgtc tgccagatgt ggtaacatac aataccctgt tgaatgggct ctgtaagcag   1140
cacaggttgc ttgacgcgga gaaacttttg aatgagatgg aggagagagg ggttacacca   1200
gatttatgca ctttcacaac tttgattcat gggtactgta ggcaaggtaa ctttgagaat   1260
gcattgcaat tgtttgacac actgttgcgc cagcgtttga ggccagatgt cgtgacatac   1320
aatagtttga ttgatgggat gtgcagaaaa ggtgatctgg ccaaagctaa tgagctatgg   1380
gatgatatgc atgctcgaga aatcttaccc aatcacatta cctacagtat cctaatagac   1440
agccactgtg agaagggaca agttgaggat gcattcggtt ttctggatga aatggtcaag   1500
aagggaaatt tgcctaatat caggacctat aattccatca tcaagggtta ttgccgatca   1560
ggtaatgtaa aaaaggggca gcagtttttg caaaagatga ggcaagataa cgtattccca   1620
gatctgatta ctttcaacac cctgatccat ggttatataa aagaagaaaa catgcatgga   1680
gctttcaatg tgtttaatat aatggagaag gaaatggtac ggccagatgc tgtcacgtat   1740
aatatgatca taaatgggtt ttctgaacaa ggcaatatgc aagatgctgg tcgtgttttc   1800
aagggaatgg gtgacagtgg aattgaaccg gatagatata catacatgtc attgataaat   1860
ggtcatgtta cagctggcaa ctcgaagcag gcgttccaac ttcatgacga gatgatccat   1920
agagggtttg ctcccgatga caaattttga                                    1950
```

<210> SEQ ID NO 86
<211> LENGTH: 649
<212> TYPE: PRT
<213> ORGANISM: Zea mays

<400> SEQUENCE: 86

```
Met Ala Ile Pro Arg Arg Leu Ser Cys Leu Pro Thr Val Ala Ala Ala
1               5                   10                  15

Thr Lys Trp Ser Ala Gly Asn Leu Ala Ile Asp Ile Gly Thr Ile Gly
            20                  25                  30

Ala Arg Pro Ser Thr Ala Ala Leu Ala Ala Ala Ala Thr Ala Ala Ala
        35                  40                  45
```

```
Ala Ala Gly Arg Ala Ser Glu Cys Gln Ser Leu Leu Leu Arg Met Ser
    50                  55                  60

Arg Arg Arg Gly Ala Ser Arg Arg Glu Ile Val Ser Ser Leu Leu Ala
65                  70                  75                  80

Ser Ser Pro Thr Pro Gln Pro Gln Val Phe Asp Leu Leu Ile Arg Thr
                85                  90                  95

Tyr Thr Gln Ser Arg Lys Pro Arg Glu Ala Phe Glu Ala Phe Arg Leu
            100                 105                 110

Leu Leu Asp His Arg Val Pro Val Pro Ala Ser Ala Ser Asn Ala Leu
        115                 120                 125

Leu Ala Val Leu Ser Arg Ala Gly Trp Pro His Leu Ala Gln Glu Ala
    130                 135                 140

Tyr Arg Leu Val Leu Ser Ser Asp Ser Glu Val Asn Ala Tyr Thr Leu
145                 150                 155                 160

Asn Ile Met Val His Ser Tyr Cys Lys Thr Leu Glu Phe Asp Gly Ala
                165                 170                 175

Asp Thr Val Ile Ser Glu Met Glu Lys Arg Cys Val Phe Pro Asp Val
            180                 185                 190

Val Thr His Asn Val Leu Ile Asp Ala Arg Phe Arg Ala Gly Asp Val
        195                 200                 205

Asp Ala Ala Ile Ala Leu Val Asp Ser Met Ala Asn Arg Gly Leu Lys
    210                 215                 220

Pro Gly Ile Val Thr Tyr Asn Ser Val Leu Lys Gly Leu Cys Lys His
225                 230                 235                 240

Arg Arg Phe Asp Lys Ala Lys Glu Val Phe Arg Thr Met Asp Gln Cys
                245                 250                 255

Ser Val Ala Pro Asp Val Arg Ser Phe Asn Ile Leu Ile Gly Gly Phe
            260                 265                 270

Cys Arg Val Gly Glu Val Lys Glu Ala Val Lys Phe Tyr Lys Glu Met
        275                 280                 285

Gln His Arg Tyr Val Thr Pro Asp Val Val Ser Phe Ser Cys Leu Ile
    290                 295                 300

Gly Leu Phe Ser Arg Arg Gly Glu Met Asp His Ala Gly Ala Tyr Leu
305                 310                 315                 320

Arg Glu Met Lys Gly Leu Gly Leu Val Pro Asp Gly Val Ile Tyr Thr
                325                 330                 335

Met Val Ile Gly Gly Phe Cys Arg Ala Gly Ser Met Ser Glu Ala Leu
            340                 345                 350

Arg Val Arg Asp Glu Met Val Gly Phe Gly Cys Leu Pro Asp Val Val
        355                 360                 365

Thr Tyr Asn Thr Leu Leu Asn Gly Leu Cys Lys Gln His Arg Leu Leu
    370                 375                 380

Asp Ala Glu Lys Leu Leu Asn Glu Met Glu Glu Arg Gly Val Thr Pro
385                 390                 395                 400

Asp Leu Cys Thr Phe Thr Thr Leu Ile His Gly Tyr Cys Arg Gln Gly
                405                 410                 415

Asn Phe Glu Asn Ala Leu Gln Leu Phe Asp Thr Leu Leu Arg Gln Arg
            420                 425                 430

Leu Arg Pro Asp Val Val Thr Tyr Asn Ser Leu Ile Asp Gly Met Cys
        435                 440                 445

Arg Lys Gly Asp Leu Ala Lys Ala Asn Glu Leu Trp Asp Asp Met His
    450                 455                 460
```

```
Ala Arg Glu Ile Leu Pro Asn His Ile Thr Tyr Ser Ile Leu Ile Asp
465                 470                 475                 480

Ser His Cys Glu Lys Gly Gln Val Glu Asp Ala Phe Gly Phe Leu Asp
                485                 490                 495

Glu Met Val Lys Lys Gly Asn Leu Pro Asn Ile Arg Thr Tyr Asn Ser
            500                 505                 510

Ile Ile Lys Gly Tyr Cys Arg Ser Gly Asn Val Lys Lys Gly Gln Gln
        515                 520                 525

Phe Leu Gln Lys Met Arg Gln Asp Asn Val Phe Pro Asp Leu Ile Thr
    530                 535                 540

Phe Asn Thr Leu Ile His Gly Tyr Ile Lys Glu Glu Asn Met His Gly
545                 550                 555                 560

Ala Phe Asn Val Phe Asn Ile Met Glu Lys Glu Met Val Arg Pro Asp
                565                 570                 575

Ala Val Thr Tyr Asn Met Ile Ile Asn Gly Phe Ser Glu Gln Gly Asn
            580                 585                 590

Met Gln Asp Ala Gly Arg Val Phe Lys Gly Met Gly Asp Ser Gly Ile
        595                 600                 605

Glu Pro Asp Arg Tyr Thr Tyr Met Ser Leu Ile Asn Gly His Val Thr
    610                 615                 620

Ala Gly Asn Ser Lys Gln Ala Phe Gln Leu His Asp Glu Met Ile His
625                 630                 635                 640

Arg Gly Phe Ala Pro Asp Asp Lys Phe
                645
```

<210> SEQ ID NO 87
<211> LENGTH: 1950
<212> TYPE: DNA
<213> ORGANISM: Sorghum bicolor

<400> SEQUENCE: 87

```
atggcgattc cccggcgcct ctttcgcctt cccgcggccg ccgcagccac caattggtcg      60

gccggaactc tcgccgcaga catcggcgga accggcgcga gaccctcaac ggccgccctg     120

gctgccgcag cgacggacgc cgccgccgcc ggccgcgcct cggagtgcca gtccctcctc     180

ctccgcatgt cgcgccgccg cggtgcctcc cgacgcgaga tcgtctcctc cctcctcgcc     240

tcgtcccccca ccccacagcc gcaggtgttc gacctcctca tccgcaccta cacccagtcc     300

cgcaagcccc gggaggcctt cgaggccttc cgcctcctcc ttgaccaccg cgtccccgtc     360

cccgcctccg cgtccaacgc cctccttgcc gcgctctccc gggccgggtg gcctcacctc     420

gccgaggagg cctaccgcct cgtcctctcg tccgactctg aggtaaacgc ctacacgctt     480

aacatcatgg tccacagcta ctgtaaaagc ctagagttcg ataaggctga cactgtcatc     540

tccgagatgg agaagagatg cgtgtttccg gatgtggtta cacataatgt gttgattgat     600

gccagattcc gtgccggaga tgtggatgca gcaattgcat tggttgattc gatggctaat     660

aaggggttga agcctgggat tgtgaccttc aattcggttt tgaaggggtt gtgtaagcac     720

aggagattcg ataaggcaaa ggaggtgttc agggcaatgg accagtgcag tgttgcgcca     780

gatgttcgga gtttcaatat tttgatcgga ggattttgta gggttgggga ggttgaggag     840

gcgatgaagt tttacaagga gatgcaacag cgtggtgtta caccagatgt ggtcagcttt     900

agctgtctga tcggattatt ctcaacgagg gggaagatgg accatgcggc agcatacttg     960

agggaaatga aggggcttgg gttggtgcca gatggtgtga tttacacaat ggtcataggt    1020

gggttttgta gggctggatc aatgtcagag gctctacgag ttagggatga gatggttggc    1080
```

```
cttggatgtc tgccagatgt cgtaacatac aataccctgt tgaatgggct ctgtaagcag   1140

cacaggttgc ttgacgcaga ggagcttttg aatgagatga aggagagagg ggttacacca   1200

gatttatgca ctttcacaac tttgattcat gggtattgta gggatggtaa ttttgagaaa   1260

gcattgcaat tgtttgacac actgttgcac cagcgtttga ggccagatgt cgtggcatac   1320

aatagcttga ttgatggaat gtgcagaaaa ggtgatctgg ccaaagctaa tgagctatgg   1380

gatgatatgc atgctcgaga aatatttccc aatcatgtta cctacagcat cctaatagac   1440

agccactgtg agaagggaca agttgaagaa gcattcggtt ttctggatga aatggtcagt   1500

aagggcaatt taccaaacat catgacctat aattccatca tcaagggtta ttgccgatca   1560

ggtaatgtaa aaaaggggca gcagtttttg caaaagatga tgcaagataa catattgcca   1620

gatctgatta ctttcaacac cctgatccat ggttatataa aagaagaaaa catgcatgga   1680

gctttcaatg tgtttaatat aatggagaag gaaatggtac aaccagatgc tgtcacatat   1740

aatatgatca taaatgggtt ttctgaacaa ggcaatatgg aagaagctgg ccgtgttttc   1800

aagaaaatgg gtgccagtgg aattgaaccg gatagatata catacatgtc tctgataaat   1860

ggtcatgtta cagctggcaa ctcgaaggag gcattccagc ttcatgatga gatgatgcat   1920

agagggtttg ctcctgacga caaattctga                                   1950
```

```
<210> SEQ ID NO 88
<211> LENGTH: 649
<212> TYPE: PRT
<213> ORGANISM: Sorghum bicolor

<400> SEQUENCE: 88

Met Ala Ile Pro Arg Arg Leu Phe Arg Leu Pro Ala Ala Ala Ala Ala
1               5                   10                  15

Thr Asn Trp Ser Ala Gly Thr Leu Ala Ala Asp Ile Gly Gly Thr Gly
            20                  25                  30

Ala Arg Pro Ser Thr Ala Ala Leu Ala Ala Ala Ala Thr Asp Ala Ala
        35                  40                  45

Ala Ala Gly Arg Ala Ser Glu Cys Gln Ser Leu Leu Leu Arg Met Ser
    50                  55                  60

Arg Arg Arg Gly Ala Ser Arg Arg Glu Ile Val Ser Ser Leu Leu Ala
65                  70                  75                  80

Ser Ser Pro Thr Pro Gln Pro Gln Val Phe Asp Leu Leu Ile Arg Thr
                85                  90                  95

Tyr Thr Gln Ser Arg Lys Pro Arg Glu Ala Phe Glu Ala Phe Arg Leu
            100                 105                 110

Leu Leu Asp His Arg Val Pro Val Pro Ala Ser Ala Ser Asn Ala Leu
        115                 120                 125

Leu Ala Ala Leu Ser Arg Ala Gly Trp Pro His Leu Ala Glu Glu Ala
    130                 135                 140

Tyr Arg Leu Val Leu Ser Ser Asp Ser Glu Val Asn Ala Tyr Thr Leu
145                 150                 155                 160

Asn Ile Met Val His Ser Tyr Cys Lys Ser Leu Glu Phe Asp Lys Ala
                165                 170                 175

Asp Thr Val Ile Ser Glu Met Glu Lys Arg Cys Val Phe Pro Asp Val
            180                 185                 190

Val Thr His Asn Val Leu Ile Asp Ala Arg Phe Arg Ala Gly Asp Val
        195                 200                 205

Asp Ala Ala Ile Ala Leu Val Asp Ser Met Ala Asn Lys Gly Leu Lys
```

```
    210                 215                 220

Pro Gly Ile Val Thr Phe Asn Ser Val Leu Lys Gly Leu Cys Lys His
225                 230                 235                 240

Arg Arg Phe Asp Lys Ala Lys Glu Val Phe Arg Ala Met Asp Gln Cys
                245                 250                 255

Ser Val Ala Pro Asp Val Arg Ser Phe Asn Ile Leu Ile Gly Gly Phe
            260                 265                 270

Cys Arg Val Gly Glu Val Glu Glu Ala Met Lys Phe Tyr Lys Glu Met
        275                 280                 285

Gln Gln Arg Gly Val Thr Pro Asp Val Val Ser Phe Ser Cys Leu Ile
    290                 295                 300

Gly Leu Phe Ser Thr Arg Gly Lys Met Asp His Ala Ala Ala Tyr Leu
305                 310                 315                 320

Arg Glu Met Lys Gly Leu Gly Leu Val Pro Asp Gly Val Ile Tyr Thr
                325                 330                 335

Met Val Ile Gly Gly Phe Cys Arg Ala Gly Ser Met Ser Glu Ala Leu
            340                 345                 350

Arg Val Arg Asp Glu Met Val Gly Leu Gly Cys Leu Pro Asp Val Val
        355                 360                 365

Thr Tyr Asn Thr Leu Leu Asn Gly Leu Cys Lys Gln His Arg Leu Leu
    370                 375                 380

Asp Ala Glu Glu Leu Leu Asn Glu Met Lys Glu Arg Gly Val Thr Pro
385                 390                 395                 400

Asp Leu Cys Thr Phe Thr Thr Leu Ile His Gly Tyr Cys Arg Asp Gly
                405                 410                 415

Asn Phe Glu Lys Ala Leu Gln Leu Phe Asp Thr Leu Leu His Gln Arg
            420                 425                 430

Leu Arg Pro Asp Val Val Ala Tyr Asn Ser Leu Ile Asp Gly Met Cys
        435                 440                 445

Arg Lys Gly Asp Leu Ala Lys Ala Asn Glu Leu Trp Asp Asp Met His
    450                 455                 460

Ala Arg Glu Ile Phe Pro Asn His Val Thr Tyr Ser Ile Leu Ile Asp
465                 470                 475                 480

Ser His Cys Glu Lys Gly Gln Val Glu Glu Ala Phe Gly Phe Leu Asp
                485                 490                 495

Glu Met Val Ser Lys Gly Asn Leu Pro Asn Ile Met Thr Tyr Asn Ser
            500                 505                 510

Ile Ile Lys Gly Tyr Cys Arg Ser Gly Asn Val Lys Lys Gly Gln Gln
        515                 520                 525

Phe Leu Gln Lys Met Met Gln Asp Asn Ile Leu Pro Asp Leu Ile Thr
    530                 535                 540

Phe Asn Thr Leu Ile His Gly Tyr Ile Lys Glu Glu Asn Met His Gly
545                 550                 555                 560

Ala Phe Asn Val Phe Asn Ile Met Glu Lys Glu Met Val Gln Pro Asp
                565                 570                 575

Ala Val Thr Tyr Asn Met Ile Ile Asn Gly Phe Ser Glu Gln Gly Asn
            580                 585                 590

Met Glu Glu Ala Gly Arg Val Phe Lys Lys Met Gly Ala Ser Gly Ile
        595                 600                 605

Glu Pro Asp Arg Tyr Thr Tyr Met Ser Leu Ile Asn Gly His Val Thr
    610                 615                 620

Ala Gly Asn Ser Lys Glu Ala Phe Gln Leu His Asp Glu Met Met His
625                 630                 635                 640
```

Arg Gly Phe Ala Pro Asp Asp Lys Phe
645

<210> SEQ ID NO 89
<211> LENGTH: 2190
<212> TYPE: DNA
<213> ORGANISM: Arabidopsis thaliana

<400> SEQUENCE: 89

```
atgattgttc accgtataat accttcccgc gtaaaagacc ctctcactcg atttaaacct     60

ctcaaaaact tgacaacttc ttcatctccc gtattcgaac cctcttcttc ttcttcttct    120

tcttcttctt cggcttcgtt ttctgtttca gattctttct tggtggagaa gatttgtttt    180

agtttgaagc aaggtaacaa taatgtgaga aaccacctga ttcggttaaa ccctttagcc    240

gtcgttgagg ttttataccg ctgccgcaat gatttaactt taggtcaaag attcgtggat    300

caattaggtt tccattttcc gaatttcaag catacgtctt tgtctttaag cgctatgatt    360

catattctcg tgaggagtgg aagattatca gatgcacaga gttgtcttct taggatgatt    420

aggaggagtg gtgtttctag actagagatt gtgaattcct tggattctac gtttagtaat    480

tgtggttcca atgattcggt ttttgatttg ttgattagga cttatgttca ggctaggaaa    540

cttagagaag cacatgaggc ttttacattg ctgagaagca aaggttttac ggtttctatc    600

gatgcgtgta acgctcttat cgggagcttg gtgaggatcg ggtgggttga actggcttgg    660

ggtgtttatc aggagatttc tcggagtggt gttggtatta atgtctatac tctcaatatc    720

atggttaatg ctttgtgcaa agatggtaaa atggaaaaag tcggaacctt tttatcacaa    780

gtgcaagaga aaggggttta tccggatatt gtaacatata atacattgat tagtgcctac    840

tctagtaaag gtctcatgga agaggcattt gagttgatga atgctatgcc gggcaaaggg    900

tttagtcctg gtgtttatac ttataatact gtgataaatg gactgtgtaa gcatgggaaa    960

tatgagagag ccaaggaagt tttcgcggag atgttaagat ccgggttgag tcctgactcc   1020

actacctaca gatcgttgct gatggaggct tgtaagaagg gagatgtggt tgaaacggaa   1080

aaggttttca gtgatatgag atctagagat gttgttcctg atttggtttg ctttagctcg   1140

atgatgagtc tttttactcg gagtggaaat ctcgataagg cattaatgta ttttaacagt   1200

gtgaaggagg ctggtctgat tcctgacaat gtgatctata ccattcttat ccaagggtat   1260

tgtagaaaag gtatgatctc tgtagctatg aatttgagaa atgaaatgct tcagcagggt   1320

tgtgctatgg atgttgttac ctacaacacc attttgcatg gcttatgcaa acggaaaatg   1380

ttgggtgaag cggataaatt gttcaacgaa atgactgaaa gggctttgtt tccagattct   1440

tatactttaa ctatactgat tgatggacat tgtaagctcg ggaatctgca gaacgcaatg   1500

gagctctttc aaaagatgaa ggaaaagaga atcagactcg atgttgtgac atacaacact   1560

ctgttagatg ggtttggtaa agtaggcgat atcgatacag caaaagagat atgggcagat   1620

atggtatcaa aagagatact tcccactcca atatcttaca gcattttggt taacgcgttg   1680

tgcagtaaag gccatctggc tgaggcattt cgagtttggg atgaaatgat cagtaaaaat   1740

ataaagccaa cggtaatgat ttgtaactct atgataaagg gatattgtcg ttctggtaat   1800

gcctcagatg gagaaagctt tttagagaag atgatctcgg aaggttttgt gccggattgc   1860

atcagttaca acacattaat atatggtttt gttagagaag aaaacatgag caaagctttt   1920

ggtttggtaa agaagatgga ggaggagcaa ggaggattag tacctgatgt atttacatat   1980

aattcgatct tacatgggtt ttgtagacaa aatcagatga aagaagccga ggttgtgcta   2040
```

```
aggaagatga tcgagagagg tgtcaatccc gataggtcaa cgtatacttg tatgatcaat   2100

ggatttgttt ctcaagataa cttaaccgag gcatttcgga ttcacgatga gatgctgcaa   2160

agaggattct ctcctgatga taaattctga                                    2190


<210> SEQ ID NO 90
<211> LENGTH: 729
<212> TYPE: PRT
<213> ORGANISM: Arabidopsis thaliana

<400> SEQUENCE: 90

Met Ile Val His Arg Ile Ile Pro Ser Arg Val Lys Asp Pro Leu Thr
1               5                   10                  15

Arg Phe Lys Pro Leu Lys Asn Leu Thr Thr Ser Ser Ser Pro Val Phe
            20                  25                  30

Glu Pro Ser Ser Ser Ser Ser Ser Ser Ser Ser Ser Ala Ser Phe Ser
        35                  40                  45

Val Ser Asp Ser Phe Leu Val Glu Lys Ile Cys Phe Ser Leu Lys Gln
    50                  55                  60

Gly Asn Asn Asn Val Arg Asn His Leu Ile Arg Leu Asn Pro Leu Ala
65                  70                  75                  80

Val Val Glu Val Leu Tyr Arg Cys Arg Asn Asp Leu Thr Leu Gly Gln
                85                  90                  95

Arg Phe Val Asp Gln Leu Gly Phe His Phe Pro Asn Phe Lys His Thr
            100                 105                 110

Ser Leu Ser Leu Ser Ala Met Ile His Ile Leu Val Arg Ser Gly Arg
        115                 120                 125

Leu Ser Asp Ala Gln Ser Cys Leu Leu Arg Met Ile Arg Arg Ser Gly
    130                 135                 140

Val Ser Arg Leu Glu Ile Val Asn Ser Leu Asp Ser Thr Phe Ser Asn
145                 150                 155                 160

Cys Gly Ser Asn Asp Ser Val Phe Asp Leu Leu Ile Arg Thr Tyr Val
                165                 170                 175

Gln Ala Arg Lys Leu Arg Glu Ala His Glu Ala Phe Thr Leu Leu Arg
            180                 185                 190

Ser Lys Gly Phe Thr Val Ser Ile Asp Ala Cys Asn Ala Leu Ile Gly
        195                 200                 205

Ser Leu Val Arg Ile Gly Trp Val Glu Leu Ala Trp Gly Val Tyr Gln
    210                 215                 220

Glu Ile Ser Arg Ser Gly Val Gly Ile Asn Val Tyr Thr Leu Asn Ile
225                 230                 235                 240

Met Val Asn Ala Leu Cys Lys Asp Gly Lys Met Glu Lys Val Gly Thr
                245                 250                 255

Phe Leu Ser Gln Val Gln Glu Lys Gly Val Tyr Pro Asp Ile Val Thr
            260                 265                 270

Tyr Asn Thr Leu Ile Ser Ala Tyr Ser Ser Lys Gly Leu Met Glu Glu
        275                 280                 285

Ala Phe Glu Leu Met Asn Ala Met Pro Gly Lys Gly Phe Ser Pro Gly
    290                 295                 300

Val Tyr Thr Tyr Asn Thr Val Ile Asn Gly Leu Cys Lys His Gly Lys
305                 310                 315                 320

Tyr Glu Arg Ala Lys Glu Val Phe Ala Glu Met Leu Arg Ser Gly Leu
                325                 330                 335

Ser Pro Asp Ser Thr Thr Tyr Arg Ser Leu Leu Met Glu Ala Cys Lys
```

```
            340                 345                 350

Lys Gly Asp Val Val Glu Thr Glu Lys Val Phe Ser Asp Met Arg Ser
        355                 360                 365

Arg Asp Val Val Pro Asp Leu Val Cys Phe Ser Ser Met Met Ser Leu
    370                 375                 380

Phe Thr Arg Ser Gly Asn Leu Asp Lys Ala Leu Met Tyr Phe Asn Ser
385                 390                 395                 400

Val Lys Glu Ala Gly Leu Ile Pro Asp Asn Val Ile Tyr Thr Ile Leu
                405                 410                 415

Ile Gln Gly Tyr Cys Arg Lys Gly Met Ile Ser Val Ala Met Asn Leu
            420                 425                 430

Arg Asn Glu Met Leu Gln Gln Gly Cys Ala Met Asp Val Val Thr Tyr
        435                 440                 445

Asn Thr Ile Leu His Gly Leu Cys Lys Arg Lys Met Leu Gly Glu Ala
    450                 455                 460

Asp Lys Leu Phe Asn Glu Met Thr Glu Arg Ala Leu Phe Pro Asp Ser
465                 470                 475                 480

Tyr Thr Leu Thr Ile Leu Ile Asp Gly His Cys Lys Leu Gly Asn Leu
                485                 490                 495

Gln Asn Ala Met Glu Leu Phe Gln Lys Met Lys Glu Lys Arg Ile Arg
            500                 505                 510

Leu Asp Val Val Thr Tyr Asn Thr Leu Leu Asp Gly Phe Gly Lys Val
        515                 520                 525

Gly Asp Ile Asp Thr Ala Lys Glu Ile Trp Ala Asp Met Val Ser Lys
    530                 535                 540

Glu Ile Leu Pro Thr Pro Ile Ser Tyr Ser Ile Leu Val Asn Ala Leu
545                 550                 555                 560

Cys Ser Lys Gly His Leu Ala Glu Ala Phe Arg Val Trp Asp Glu Met
                565                 570                 575

Ile Ser Lys Asn Ile Lys Pro Thr Val Met Ile Cys Asn Ser Met Ile
            580                 585                 590

Lys Gly Tyr Cys Arg Ser Gly Asn Ala Ser Asp Gly Glu Ser Phe Leu
        595                 600                 605

Glu Lys Met Ile Ser Glu Gly Phe Val Pro Asp Cys Ile Ser Tyr Asn
    610                 615                 620

Thr Leu Ile Tyr Gly Phe Val Arg Glu Glu Asn Met Ser Lys Ala Phe
625                 630                 635                 640

Gly Leu Val Lys Lys Met Glu Glu Glu Gln Gly Gly Leu Val Pro Asp
                645                 650                 655

Val Phe Thr Tyr Asn Ser Ile Leu His Gly Phe Cys Arg Gln Asn Gln
            660                 665                 670

Met Lys Glu Ala Glu Val Val Leu Arg Lys Met Ile Glu Arg Gly Val
        675                 680                 685

Asn Pro Asp Arg Ser Thr Tyr Thr Cys Met Ile Asn Gly Phe Val Ser
    690                 695                 700

Gln Asp Asn Leu Thr Glu Ala Phe Arg Ile His Asp Glu Met Leu Gln
705                 710                 715                 720

Arg Gly Phe Ser Pro Asp Asp Lys Phe
                725
```

<210> SEQ ID NO 91
<211> LENGTH: 1779
<212> TYPE: DNA
<213> ORGANISM: Glycine max

<400> SEQUENCE: 91

```
gtccacgacc tcgttcgtgc ccggaacctc ccagaagccc aatccctcct cctccgaatg      60
atccgaaaac gcggcgtttc gcgcccccaa ctcatcgatt ccctccttcc ttcttctccc     120
agttccactc acaccaacgc caccgttctc gatttgctca tcagaaccta cgttcagtcg     180
cggaagcttc gagaaggctc ggaagccttc cgcttgctga ggcaaaaggg cttctccgtt     240
tccatcaacg cctccaacgc gcttctgggc gcgttggtca aagtggggtg ggtcgacttg     300
gcatggacag tgtacgagga tgttgtcgca agtggcacaa cggtaaatgt ctacactctc     360
aacatcatgg tcaatgcttt gtgtaaagag gccaggttcg acaaggttaa ggtttttcttg    420
tcccaaatgg agggaaaagg tgttttccct gatgttgtaa cttataacac tttaatcaac     480
gcgcattctc gtcagggtaa tgtggcagag gcttttgagc tcctgggctt ttatacttat     540
aatgctattg ttaatgggtt gtgtaagaag ggggattatg tgagagcgag gggtgttttt     600
gatgagatgt tggggatggg gttgagtcct gatgctgcca cttttaatcc cttgcttgtg     660
gaatgttgta ggaaggatga tgcttgtgag gctgagaatg tttttgatga aatgttgcgg     720
tacggggttg ttcctgattt gattagtttt ggatctgtga ttggggtgtt ctccaggaac     780
gggctcttcg ataaggcgtt ggagtatttt gggaagatga agggttctgg attggttgct     840
gatacggtga tttataccat tcttattgac gggtattgca ggaatggcaa tgtggctgag     900
gcattggcca tgcggaacga gatggttgaa aagggttgct ttatggatgt ggttacgtat     960
aatactctgc tgaatgggtt gtgtaggggg aagatgcttg gtgatgccga tgagttgttt    1020
aaggagatgg tggagagggg agtttttccg gattactata cccttaccac tctcattcat    1080
gggtattgta aggatgggaa catgagtagg gcacttggtt tgtttgagac gatgactcaa    1140
aggagcctta agccggatgt tgtgacatat aatacattga tggatggctt ttgcaagatt    1200
ggtgaaatgg agaaagctaa ggagttgtgg cgtgatatgg tgagcagggg gatattgccc    1260
aactatgtat cgtttagcat tttgataaat gggttttgca gtttaggact tatgggtgag    1320
gcattcaggg tgtgggatga aatgatagaa aaaggtgtta agcccacttt ggttacttgc    1380
aacactgtta taaagggcca tttgcgggct ggcaatgtgt taaaggcaaa tgacttcttc    1440
gaaaagatga ttttggaagg agtttctcct gattgcatca cgtataatac tcttataaat    1500
ggttttgtaa aggaagagaa tttcgacagg gcttttgtct tggttaataa catggaagaa    1560
aaagggctac tgccagatgt catcacttat aatgcaattc tcggtggata ttgtaggcaa    1620
ggcagaatgc gggaggctga gatggtgtta cgcaagatga ttgactgtgg catcaatcct    1680
gataaatcaa catacacatc attgataaat gggcatgtat ctctagacaa cttgaaagaa    1740
gcattccgtt tccacgatga aatgctgcaa aggggattt                            1779
```

<210> SEQ ID NO 92
<211> LENGTH: 593
<212> TYPE: PRT
<213> ORGANISM: Glycine max

<400> SEQUENCE: 92

```
Val His Asp Leu Val Arg Ala Arg Asn Leu Pro Glu Ala Gln Ser Leu
1               5                   10                  15

Leu Leu Arg Met Ile Arg Lys Arg Gly Val Ser Arg Pro Gln Leu Ile
            20                  25                  30

Asp Ser Leu Leu Pro Ser Ser Pro Ser Ser Thr His Thr Asn Ala Thr
        35                  40                  45
```

```
Val Leu Asp Leu Leu Ile Arg Thr Tyr Val Gln Ser Arg Lys Leu Arg
    50                  55                  60

Glu Gly Ser Glu Ala Phe Arg Leu Leu Arg Gln Lys Gly Phe Ser Val
65                  70                  75                  80

Ser Ile Asn Ala Ser Asn Ala Leu Leu Gly Ala Leu Val Lys Val Gly
                85                  90                  95

Trp Val Asp Leu Ala Trp Thr Val Tyr Glu Asp Val Val Ala Ser Gly
            100                 105                 110

Thr Thr Val Asn Val Tyr Thr Leu Asn Ile Met Val Asn Ala Leu Cys
        115                 120                 125

Lys Glu Ala Arg Phe Asp Lys Val Lys Val Phe Leu Ser Gln Met Glu
    130                 135                 140

Gly Lys Gly Val Phe Pro Asp Val Val Thr Tyr Asn Thr Leu Ile Asn
145                 150                 155                 160

Ala His Ser Arg Gln Gly Asn Val Ala Glu Ala Phe Glu Leu Leu Gly
                165                 170                 175

Phe Tyr Thr Tyr Asn Ala Ile Val Asn Gly Leu Cys Lys Lys Gly Asp
            180                 185                 190

Tyr Val Arg Ala Arg Gly Val Phe Asp Glu Met Leu Gly Met Gly Leu
        195                 200                 205

Ser Pro Asp Ala Ala Thr Phe Asn Pro Leu Leu Val Glu Cys Cys Arg
    210                 215                 220

Lys Asp Asp Ala Cys Glu Ala Glu Asn Val Phe Asp Glu Met Leu Arg
225                 230                 235                 240

Tyr Gly Val Val Pro Asp Leu Ile Ser Phe Gly Ser Val Ile Gly Val
                245                 250                 255

Phe Ser Arg Asn Gly Leu Phe Asp Lys Ala Leu Glu Tyr Phe Gly Lys
            260                 265                 270

Met Lys Gly Ser Gly Leu Val Ala Asp Thr Val Ile Tyr Thr Ile Leu
        275                 280                 285

Ile Asp Gly Tyr Cys Arg Asn Gly Asn Val Ala Glu Ala Leu Ala Met
    290                 295                 300

Arg Asn Glu Met Val Glu Lys Gly Cys Phe Met Asp Val Val Thr Tyr
305                 310                 315                 320

Asn Thr Leu Leu Asn Gly Leu Cys Arg Gly Lys Met Leu Gly Asp Ala
                325                 330                 335

Asp Glu Leu Phe Lys Glu Met Val Glu Arg Gly Val Phe Pro Asp Tyr
            340                 345                 350

Tyr Thr Leu Thr Thr Leu Ile His Gly Tyr Cys Lys Asp Gly Asn Met
        355                 360                 365

Ser Arg Ala Leu Gly Leu Phe Glu Thr Met Thr Gln Arg Ser Leu Lys
    370                 375                 380

Pro Asp Val Val Thr Tyr Asn Thr Leu Met Asp Gly Phe Cys Lys Ile
385                 390                 395                 400

Gly Glu Met Glu Lys Ala Lys Glu Leu Trp Arg Asp Met Val Ser Arg
                405                 410                 415

Gly Ile Leu Pro Asn Tyr Val Ser Phe Ser Ile Leu Ile Asn Gly Phe
            420                 425                 430

Cys Ser Leu Gly Leu Met Gly Glu Ala Phe Arg Val Trp Asp Glu Met
        435                 440                 445

Ile Glu Lys Gly Val Lys Pro Thr Leu Val Thr Cys Asn Thr Val Ile
    450                 455                 460
```

```
Lys Gly His Leu Arg Ala Gly Asn Val Leu Lys Ala Asn Asp Phe Phe
465                 470                 475                 480

Glu Lys Met Ile Leu Glu Gly Val Ser Pro Asp Cys Ile Thr Tyr Asn
                485                 490                 495

Thr Leu Ile Asn Gly Phe Val Lys Glu Glu Asn Phe Asp Arg Ala Phe
            500                 505                 510

Val Leu Val Asn Asn Met Glu Glu Lys Gly Leu Leu Pro Asp Val Ile
        515                 520                 525

Thr Tyr Asn Ala Ile Leu Gly Gly Tyr Cys Arg Gln Gly Arg Met Arg
    530                 535                 540

Glu Ala Glu Met Val Leu Arg Lys Met Ile Asp Cys Gly Ile Asn Pro
545                 550                 555                 560

Asp Lys Ser Thr Tyr Thr Ser Leu Ile Asn Gly His Val Ser Leu Asp
                565                 570                 575

Asn Leu Lys Glu Ala Phe Arg Phe His Asp Glu Met Leu Gln Arg Gly
            580                 585                 590

Phe
```

<210> SEQ ID NO 93
<211> LENGTH: 726
<212> TYPE: DNA
<213> ORGANISM: Zea mays

<400> SEQUENCE: 93

```
atgcatgcat gcatgtggct gcttgcttgc ttgcttgcat tctgtacaag aagaacttca     60

tcgatcgatc gatcgatcct cgagtccagg actgaaccga accgatctga tctgatctac    120

gcgtacgcac cacgccaaca agcagatcgt tacagacaat taagaaggaa cctagctagc    180

ttgcggcatc taccggcaga cggtggcttt cttcttcccc ttcccggcgg cgttcttgcg    240

ctggaggcgg cgcaggaggt cctccaggtc ctcctcggcg cacggcacgc gcaggccgcc    300

cgcctgcgcg aagccgaact cgtcggcggc gcgctccatg aggtcccgga acgccggctc    360

ccggaggtac ccggtgggca cgacgaaccg gcgccgcgac tcctccccgg cgtacaccgc    420

gaagtagccc ttgggcacgc cgccctcctc ctccgccgcc gccggctggt ccagcagcgc    480

ctcccggagg cccagctcct cgcgcgtcgt cctcgccttc tgcttggccg ccgccgtcgc    540

ggacttggtc gtcgacgagc ggaagtagcc catcaccatc atcgtgtcac tcgtgcgtcg    600

tcggtcggtc ggtcgtactc gtacgtatac gtagcgtggc cgccgggcga gtgcagccgt    660

gaacacgtac gtacgcaaca actaacgccg ggcgagtgcg cagagggctt agctagtagt    720

aggtaa                                                               726
```

<210> SEQ ID NO 94
<211> LENGTH: 241
<212> TYPE: PRT
<213> ORGANISM: Zea mays

<400> SEQUENCE: 94

```
Met His Ala Cys Met Trp Leu Leu Ala Cys Leu Leu Ala Phe Cys Thr
1               5                   10                  15

Arg Arg Thr Ser Ser Ile Asp Arg Ser Ile Leu Glu Ser Arg Thr Glu
            20                  25                  30

Pro Asn Arg Ser Asp Leu Ile Tyr Ala Tyr Ala Pro Arg Gln Gln Ala
        35                  40                  45

Asp Arg Tyr Arg Gln Leu Arg Arg Asn Leu Ala Ser Leu Arg His Leu
    50                  55                  60
```

```
Pro Ala Asp Gly Gly Phe Leu Leu Pro Leu Pro Gly Gly Val Leu Ala
65                  70                  75                  80

Leu Glu Ala Ala Gln Glu Val Leu Gln Val Leu Leu Gly Ala Arg His
                85                  90                  95

Ala Gln Ala Ala Arg Leu Arg Glu Ala Glu Leu Val Gly Gly Ala Leu
            100                 105                 110

His Glu Val Pro Glu Arg Arg Leu Pro Glu Val Pro Gly Gly His Asp
        115                 120                 125

Glu Pro Ala Pro Arg Leu Leu Pro Gly Val His Arg Glu Val Ala Leu
    130                 135                 140

Gly His Ala Ala Leu Leu Leu Arg Arg Arg Arg Leu Val Gln Gln Arg
145                 150                 155                 160

Leu Pro Glu Ala Gln Leu Leu Ala Arg Arg Pro Arg Leu Leu Leu Gly
                165                 170                 175

Arg Arg Arg Arg Gly Leu Gly Arg Arg Arg Ala Glu Val Ala His His
            180                 185                 190

His His Arg Val Thr Arg Ala Ser Ser Val Gly Arg Ser Tyr Ser Tyr
        195                 200                 205

Val Tyr Val Ala Trp Pro Pro Gly Glu Cys Ser Arg Glu His Val Arg
    210                 215                 220

Thr Gln Gln Leu Thr Pro Gly Glu Cys Ala Glu Gly Leu Ala Ser Ser
225                 230                 235                 240

Arg
```

<210> SEQ ID NO 95
<211> LENGTH: 405
<212> TYPE: DNA
<213> ORGANISM: Sorghum bicolor

<400> SEQUENCE: 95

```
atgatggtga tgggctactt ccggtcgacg aacaagtccg cgacgtcggc agcgggcggc     60

aagaacaaga agaaggcgaa gaacagctgt gcgccggcgg cgcgcgagga ggcggccgga    120

ctgcgggagg cgctgctgga ccagccggcg gcggcggagg aggacggcgg cgttcctaag    180

ggctacttcg cggtgtacgc cggggaggag tcccgccggt tcgtcgtgcc cacggggtac    240

ctccgggagc cggcgttccg ggacctcatg gagcgcgccg ccgacgagtt cggcttcgcg    300

caggccggcg gcctgcgcgt gccctgcgcc gaggaggact tcgaggacct cctgcgccgt    360

ctccagcgca agaacggcgg cgccgtcggg aagggcaaga aataa                    405
```

<210> SEQ ID NO 96
<211> LENGTH: 134
<212> TYPE: PRT
<213> ORGANISM: Sorghum bicolor

<400> SEQUENCE: 96

```
Met Met Val Met Gly Tyr Phe Arg Ser Thr Asn Lys Ser Ala Thr Ser
1               5                   10                  15

Ala Ala Gly Gly Lys Asn Lys Lys Lys Ala Lys Asn Ser Cys Ala Pro
            20                  25                  30

Ala Ala Arg Glu Glu Ala Ala Gly Leu Arg Glu Ala Leu Leu Asp Gln
        35                  40                  45

Pro Ala Ala Ala Glu Glu Asp Gly Gly Val Pro Lys Gly Tyr Phe Ala
    50                  55                  60

Val Tyr Ala Gly Glu Glu Ser Arg Arg Phe Val Val Pro Thr Gly Tyr
```

```
65                  70                  75                  80

Leu Arg Glu Pro Ala Phe Arg Asp Leu Met Glu Arg Ala Ala Asp Glu
                85                  90                  95

Phe Gly Phe Ala Gln Ala Gly Gly Leu Arg Val Pro Cys Ala Glu Glu
            100                 105                 110

Asp Phe Glu Asp Leu Leu Arg Arg Leu Gln Arg Lys Asn Gly Gly Ala
        115                 120                 125

Val Gly Lys Gly Lys Lys
    130


<210> SEQ ID NO 97
<211> LENGTH: 537
<212> TYPE: DNA
<213> ORGANISM: Arabidopsis thaliana

<400> SEQUENCE: 97

atggaagcca agaagtcaaa caagatcaga gagatcgtta agcttcaaca gcttctcaag      60

aaatggcgaa aacaagcaat tgcatcaaaa gcagccaaca acaacaacga agacaacaat     120

agcagtggcg ggggaagcaa gagcatcaag tttctgaaga ggacactgtc atttacagat     180

gtaacagctg tgcctaaagg gtatctagct gtttcggtcg ggttagagaa gaagaggtac     240

acaataccaa ccgagtacct cagccatcaa gctttctatg ttcttctgcg tgaggcagaa     300

gaagagttcg ggtttcaaca agccggtgtc ttgaggattc cttgtgaagt ttctgttttt     360

gagagcatat tgaagataat ggaggagaag aacgaagggt acctggtgac gccaataaca     420

gctaagcagg aatgtaagtt caatgcagca gcagatgata agacgagtta ccagcatcca     480

tcagactgtc ctaagactcc ttcacaccaa cctcacaaca gcccaatgtg cagatag       537


<210> SEQ ID NO 98
<211> LENGTH: 178
<212> TYPE: PRT
<213> ORGANISM: Arabidopsis thaliana

<400> SEQUENCE: 98

Met Glu Ala Lys Lys Ser Asn Lys Ile Arg Glu Ile Val Lys Leu Gln
1               5                   10                  15

Gln Leu Leu Lys Lys Trp Arg Lys Gln Ala Ile Ala Ser Lys Ala Ala
            20                  25                  30

Asn Asn Asn Asn Glu Asp Asn Asn Ser Ser Gly Gly Gly Ser Lys Ser
        35                  40                  45

Ile Lys Phe Leu Lys Arg Thr Leu Ser Phe Thr Asp Val Thr Ala Val
    50                  55                  60

Pro Lys Gly Tyr Leu Ala Val Ser Val Gly Leu Glu Lys Lys Arg Tyr
65                  70                  75                  80

Thr Ile Pro Thr Glu Tyr Leu Ser His Gln Ala Phe Tyr Val Leu Leu
                85                  90                  95

Arg Glu Ala Glu Glu Glu Phe Gly Phe Gln Gln Ala Gly Val Leu Arg
            100                 105                 110

Ile Pro Cys Glu Val Ser Val Phe Glu Ser Ile Leu Lys Ile Met Glu
        115                 120                 125

Glu Lys Asn Glu Gly Tyr Leu Val Thr Pro Ile Thr Ala Lys Gln Glu
    130                 135                 140

Cys Lys Phe Asn Ala Ala Ala Asp Asp Lys Thr Ser Tyr Gln His Pro
145                 150                 155                 160

Ser Asp Cys Pro Lys Thr Pro Ser His Gln Pro His Asn Ser Pro Met
```

165 170 175

Cys Arg

<210> SEQ ID NO 99
<211> LENGTH: 504
<212> TYPE: DNA
<213> ORGANISM: Glycine max

<400> SEQUENCE: 99
atggatagcg atggaggctc caaattgaat gggattaggc agattgtgaa gctaaaggaa 60
atgctccaga agtggcaaag tgtgacatta ggcaccaaac cttccaattc cctttctgat 120
catgtgacta atgatgatgg gagcatatca ccattgatca acaaaagtgt attgaatgtg 180
atgaattgcg aatcagacaa tgaggacagt tgccaaagcc ctgcagaacc gcttccacca 240
cctgatgttc cgaaagggta cttggcagtg tatgttggac ctgagcttag gaggttcatc 300
atccccacca gttaccttag ccaccctctc ttcaaagttt tgctggaaaa ggctgcagac 360
gaattcgggt ttgatcagag tggtggcctc accatcccat gtgagattga gaccttcaag 420
taccttctca agtgcatgga gaatgagcag aaagagcaac tcggtgacag cgcccctgga 480
agctcagggt ctgtcgaaga gtaa 504

<210> SEQ ID NO 100
<211> LENGTH: 167
<212> TYPE: PRT
<213> ORGANISM: Glycine max

<400> SEQUENCE: 100

Met Asp Ser Asp Gly Gly Ser Lys Leu Asn Gly Ile Arg Gln Ile Val
1 5 10 15

Lys Leu Lys Glu Met Leu Gln Lys Trp Gln Ser Val Thr Leu Gly Thr
20 25 30

Lys Pro Ser Asn Ser Leu Ser Asp His Val Thr Asn Asp Asp Gly Ser
35 40 45

Ile Ser Pro Leu Ile Asn Lys Ser Val Leu Asn Val Met Asn Cys Glu
50 55 60

Ser Asp Asn Glu Asp Ser Cys Gln Ser Pro Ala Glu Pro Leu Pro Pro
65 70 75 80

Pro Asp Val Pro Lys Gly Tyr Leu Ala Val Tyr Val Gly Pro Glu Leu
85 90 95

Arg Arg Phe Ile Ile Pro Thr Ser Tyr Leu Ser His Pro Leu Phe Lys
100 105 110

Val Leu Leu Glu Lys Ala Ala Asp Glu Phe Gly Phe Asp Gln Ser Gly
115 120 125

Gly Leu Thr Ile Pro Cys Glu Ile Glu Thr Phe Lys Tyr Leu Leu Lys
130 135 140

Cys Met Glu Asn Glu Gln Lys Glu Gln Leu Gly Asp Ser Ala Pro Gly
145 150 155 160

Ser Ser Gly Ser Val Glu Glu
165

<210> SEQ ID NO 101
<211> LENGTH: 1638
<212> TYPE: DNA
<213> ORGANISM: Oryza sativa

<400> SEQUENCE: 101

```
atgagaagcc caccggagag cgggtcgcgc accggtcgag gcgaagaaat tgcggcgcgg      60
caactaaacc ctaccgcctc tgcctcgccg ccacgctccc ttattatgga cggggcctgc     120
tgcgacggcg gtggctcgcc ggagtccggc ggggcgtcct cgtcggcgtc gtcgtacggc     180
tccgcgtccc ggctgcagaa gggggtgcgc ctgcggcggc ggcggcagag gctccggaga     240
ccgctgcttg cgactggagg ggatgggagg ggcgccgccg acggcgcgca ggacctcgcg     300
ctgcctctcg ggatgtcctt cgcggcggtt cttgcccagg tccttaatag aagcagttgc     360
tctgaaggaa gattacaacc tgatttcctt tcaaagatgt gcacgtcagc agtgaaagag     420
tccttgacaa atatatatgg tgatagattc gacaacttca cgaaaaactt tgagaaatca     480
tttggaagta cattgaggac acttcattta attaatgaga cacctgtcta tgagcaagat     540
aactctcggt tttctcacga agatggtact tctgctgctg aaatcaaatt gagtggtgct     600
gattcaaaaa ggccggtaca tgatatccag gagagtacat cgttaagttc aatggataat     660
caaatcattc ttcatgcggg caccgatcag cagttggtta aactacctca taataaagct     720
agtccagaat ttgataggca cattcttaat gtatttgaga gatctctgaa tgagcagact     780
cgttcaaatg agctcaagga acttgaaata ggactaaaca tgaggaaatt gcaattgaag     840
caatctcaga tagctctcag ctcatactca cacatgctag agaagatcaa aatttctatg     900
ggatttcaga aagcttcttt cagagaggaa aaatttagga cgcaaatgga ggacacaaga     960
catgctgaac tcctcaggag gcttatagat ttgctcctta ccgcagtggt atttatgtct    1020
gtctgttttg gttatggaac ctatatttat tcgtacaagc ggataactgc tgttactgca    1080
gcttgtgcag cggcttcaag ggaacctaaa tcttggtgga tgccaaattc agtatcagct    1140
ttcaattcgg gtttgctgtt tttcaggtgt catttaatag cagcaacaag gatgtcattt    1200
ggcatgttaa tgattctctt gattgcttgg ttgatattcc agcgttctgc aatgactgga    1260
ccaaacatgc caataacgtt caatgttatg ttattgggag ttctctgtgg ttctgtcgga    1320
aggttctgcg ttgacacact aggcggggat ggaaatgtct ggctcttttt ctgggagatt    1380
ctctgcttca tccatttatt tgggaacagc aggccatctc ttttataccg catgctttat    1440
ggtcctattt cagtgactga cagaacgaag gcgtctgatt taccatatcg ggtttgccga    1500
tacacatttt atactgtcct gtcggttatt ctcccatgct tggctggttt gctgccattt    1560
gcttccctgt cagactggaa tgagcttgtg gtagaatata tgaagtccaa attcattaga    1620
attaatactg aggtttga                                                  1638
```

<210> SEQ ID NO 102
<211> LENGTH: 545
<212> TYPE: PRT
<213> ORGANISM: Oryza sativa

<400> SEQUENCE: 102

```
Met Arg Ser Pro Pro Glu Ser Gly Ser Arg Thr Gly Arg Gly Glu Glu
1               5                   10                  15

Ile Ala Ala Arg Gln Leu Asn Pro Thr Ala Ser Ala Ser Pro Pro Arg
            20                  25                  30

Ser Leu Ile Met Asp Gly Ala Cys Cys Asp Gly Gly Gly Ser Pro Glu
        35                  40                  45

Ser Gly Gly Ala Ser Ser Ser Ala Ser Ser Tyr Gly Ser Ala Ser Arg
    50                  55                  60

Leu Gln Lys Gly Val Arg Leu Arg Arg Arg Arg Gln Arg Leu Arg Arg
65                  70                  75                  80
```

-continued

```
Pro Leu Leu Ala Thr Gly Gly Asp Gly Arg Gly Ala Ala Asp Gly Ala
                85                  90                  95

Gln Asp Leu Ala Leu Pro Leu Gly Met Ser Phe Ala Ala Val Leu Ala
            100                 105                 110

Gln Val Leu Asn Arg Ser Ser Cys Ser Glu Gly Arg Leu Gln Pro Asp
        115                 120                 125

Phe Leu Ser Lys Met Cys Thr Ser Ala Val Lys Glu Ser Leu Thr Asn
    130                 135                 140

Ile Tyr Gly Asp Arg Phe Asp Asn Phe Thr Lys Asn Phe Glu Lys Ser
145                 150                 155                 160

Phe Gly Ser Thr Leu Arg Thr Leu His Leu Ile Asn Glu Thr Pro Val
                165                 170                 175

Tyr Glu Gln Asp Asn Ser Arg Phe Ser His Glu Asp Gly Thr Ser Ala
            180                 185                 190

Ala Glu Ile Lys Leu Ser Gly Ala Asp Ser Lys Arg Pro Val His Asp
        195                 200                 205

Ile Gln Glu Ser Thr Ser Leu Ser Ser Met Asp Asn Gln Ile Ile Leu
    210                 215                 220

His Ala Gly Thr Asp Gln Gln Leu Val Lys Leu Pro His Asn Lys Ala
225                 230                 235                 240

Ser Pro Glu Phe Asp Arg His Ile Leu Asn Val Phe Glu Arg Ser Leu
                245                 250                 255

Asn Glu Gln Thr Arg Ser Asn Glu Leu Lys Glu Leu Glu Ile Gly Leu
            260                 265                 270

Asn Met Arg Lys Leu Gln Leu Lys Gln Ser Gln Ile Ala Leu Ser Ser
        275                 280                 285

Tyr Ser His Met Leu Glu Lys Ile Lys Ile Ser Met Gly Phe Gln Lys
    290                 295                 300

Ala Ser Phe Arg Glu Glu Lys Phe Arg Thr Gln Met Glu Asp Thr Arg
305                 310                 315                 320

His Ala Glu Leu Leu Arg Arg Leu Ile Asp Leu Leu Leu Thr Ala Val
                325                 330                 335

Val Phe Met Ser Val Cys Phe Gly Tyr Gly Thr Tyr Ile Tyr Ser Tyr
            340                 345                 350

Lys Arg Ile Thr Ala Val Thr Ala Ala Cys Ala Ala Ala Ser Arg Glu
        355                 360                 365

Pro Lys Ser Trp Trp Met Pro Asn Ser Val Ser Ala Phe Asn Ser Gly
    370                 375                 380

Leu Leu Phe Phe Arg Cys His Leu Ile Ala Ala Thr Arg Met Ser Phe
385                 390                 395                 400

Gly Met Leu Met Ile Leu Leu Ile Ala Trp Leu Ile Phe Gln Arg Ser
                405                 410                 415

Ala Met Thr Gly Pro Asn Met Pro Ile Thr Phe Asn Val Met Leu Leu
            420                 425                 430

Gly Val Leu Cys Gly Ser Val Gly Arg Phe Cys Val Asp Thr Leu Gly
        435                 440                 445

Gly Asp Gly Asn Val Trp Leu Phe Phe Trp Glu Ile Leu Cys Phe Ile
    450                 455                 460

His Leu Phe Gly Asn Ser Arg Pro Ser Leu Leu Tyr Arg Met Leu Tyr
465                 470                 475                 480

Gly Pro Ile Ser Val Thr Asp Arg Thr Lys Ala Ser Asp Leu Pro Tyr
                485                 490                 495

Arg Val Cys Arg Tyr Thr Phe Tyr Thr Val Leu Ser Val Ile Leu Pro
```

```
            500                 505                 510

Cys Leu Ala Gly Leu Leu Pro Phe Ala Ser Leu Ser Asp Trp Asn Glu
        515                 520                 525

Leu Val Val Glu Tyr Met Lys Ser Lys Phe Ile Arg Ile Asn Thr Glu
    530                 535                 540

Val
545
```

<210> SEQ ID NO 103
<211> LENGTH: 1575
<212> TYPE: DNA
<213> ORGANISM: Zea mays

<400> SEQUENCE: 103

```
atggacacgg gctgcctcca accaccctgc aacccctcct cgtcggaggc gtcgggaggc     60

gacgcctccg acgcctgcgg ctccgcctct gcctcccggt cctcctccgc ccgccgcagc    120

aagggggtgc ggctccggct ccggctgcgg cgaaggcggc aggagccggg ccccgccgct    180

acgcctgggg gtgagggtca gggtggcgcc ggcgtgcagg tgcaggacga cctcgcgctg    240

cccctcggga tgtcgttcgc ggccgtcctc gcgcaggttg tgaatacaaa gaatcgttca    300

ggcgaaagat tacagcctgc acttctttcc aagatctgta catcggcagt gaaggaatca    360

ttgagaaata tatatggtaa caagttagac agttttatga gaaactttga gaaatcattc    420

agcagcacat tgacaacgct tcatcttgtt aatgagatgc ctgtctatgg acaaggtcca    480

gttcctcaat gttcttctaa gcatgaagac tctgaagctt caagcaagtt gagcactggt    540

ggtacacaaa atctaacgcg tgaaatcaag caggagcgtt tgaattcagt ggaaagtcag    600

cttgttcttt atgctggcgg ctatcagcag atgactcgcc gcgctcatag cttatcttct    660

cctgaagctg atcagcgcat ccttaatgca tttgagagat ctttgaaaga acaaactcgg    720

tcaaatgagc tcaaggaatt tgagataagc cttagcatga gaaagttgaa gctaaaacag    780

tctcaactag aacttaactc ctattcacac atgttagaca agattaagtt atccttggga    840

tttcagaaag cttccttcca agtggaaaaa ttcaagactc agatgcagga cacgaggcat    900

gcacaaataa tgaggacact catagatttt cttgttagtg cagtgattat tatgtcagta    960

tgctttgggt atggaactta tacttattca taccaaagga taactgatat tacagcagca   1020

tgttcagcca cttcaaaggg atctaaatca tggtggatgc caaattcagt gtcaaacttc   1080

aatactgggt tgctcttcat aagatgtcat gtaatagctg caacacggat gttctttggt   1140

atagtaatga ttttggcagt tgtttggtta gcgttccagc gctctgcggt gtctgtatca   1200

agtatgccag taacttttaa catcattctg ttgggagtta tttgtggcta cgctggaagg   1260

ttctgtacca acacacttgg tggtgatggg aacatgtggc ttatatgctg ggaggtactt   1320

tgttccgtcc atttgattgg aaattgttat ccatcggtct tgtaccgtgt tctccatggt   1380

cctatatctg tatctcatag caaggagtct gtctggttcc cgtattggat tcgccgttgg   1440

atgttttatg ctgtgctggg gtttttttatc ccagccttga atggcttact gccatttgct   1500

tctctttctg actggaataa ccatttcact aaggagctaa aatccatctt cattgatgag   1560

agaatcgaag cctga                                                     1575
```

<210> SEQ ID NO 104
<211> LENGTH: 524
<212> TYPE: PRT
<213> ORGANISM: Zea mays

<400> SEQUENCE: 104

```
Met Asp Thr Gly Cys Leu Gln Pro Pro Cys Asn Pro Ser Ser Ser Glu
1               5                   10                  15

Ala Ser Gly Gly Asp Ala Ser Asp Ala Cys Gly Ser Ala Ser Ala Ser
            20                  25                  30

Arg Ser Ser Ser Ala Arg Arg Ser Lys Gly Val Arg Leu Arg Leu Arg
        35                  40                  45

Leu Arg Arg Arg Arg Gln Glu Pro Gly Pro Ala Ala Thr Pro Gly Gly
    50                  55                  60

Glu Gly Gln Gly Gly Ala Gly Val Gln Val Gln Asp Asp Leu Ala Leu
65                  70                  75                  80

Pro Leu Gly Met Ser Phe Ala Ala Val Leu Ala Gln Val Val Asn Thr
                85                  90                  95

Lys Asn Arg Ser Gly Glu Arg Leu Gln Pro Ala Leu Leu Ser Lys Ile
            100                 105                 110

Cys Thr Ser Ala Val Lys Glu Ser Leu Arg Asn Ile Tyr Gly Asn Lys
        115                 120                 125

Leu Asp Ser Phe Met Arg Asn Phe Glu Lys Ser Phe Ser Ser Thr Leu
    130                 135                 140

Thr Thr Leu His Leu Val Asn Glu Met Pro Val Tyr Gly Gln Gly Pro
145                 150                 155                 160

Val Pro Gln Cys Ser Ser Lys His Glu Asp Ser Glu Ala Ser Ser Lys
                165                 170                 175

Leu Ser Thr Gly Gly Thr Gln Asn Leu Thr Arg Glu Ile Lys Gln Glu
            180                 185                 190

Arg Leu Asn Ser Val Glu Ser Gln Leu Val Leu Tyr Ala Gly Gly Tyr
        195                 200                 205

Gln Gln Met Thr Arg Arg Ala His Ser Leu Ser Ser Pro Glu Ala Asp
    210                 215                 220

Gln Arg Ile Leu Asn Ala Phe Glu Arg Ser Leu Lys Glu Gln Thr Arg
225                 230                 235                 240

Ser Asn Glu Leu Lys Glu Phe Glu Ile Ser Leu Ser Met Arg Lys Leu
                245                 250                 255

Lys Leu Lys Gln Ser Gln Leu Glu Leu Asn Ser Tyr Ser His Met Leu
            260                 265                 270

Asp Lys Ile Lys Leu Ser Leu Gly Phe Gln Lys Ala Ser Phe Gln Val
        275                 280                 285

Glu Lys Phe Lys Thr Gln Met Gln Asp Thr Arg His Ala Gln Ile Met
    290                 295                 300

Arg Thr Leu Ile Asp Phe Leu Val Ser Ala Val Ile Ile Met Ser Val
305                 310                 315                 320

Cys Phe Gly Tyr Gly Thr Tyr Thr Tyr Ser Tyr Gln Arg Ile Thr Asp
                325                 330                 335

Ile Thr Ala Ala Cys Ser Ala Thr Ser Lys Gly Ser Lys Ser Trp Trp
            340                 345                 350

Met Pro Asn Ser Val Ser Asn Phe Asn Thr Gly Leu Leu Phe Ile Arg
        355                 360                 365

Cys His Val Ile Ala Ala Thr Arg Met Phe Phe Gly Ile Val Met Ile
    370                 375                 380

Leu Ala Val Val Trp Leu Ala Phe Gln Arg Ser Ala Val Ser Val Ser
385                 390                 395                 400

Ser Met Pro Val Thr Phe Asn Ile Ile Leu Leu Gly Val Ile Cys Gly
                405                 410                 415
```

```
Tyr Ala Gly Arg Phe Cys Thr Asn Thr Leu Gly Gly Asp Gly Asn Met
            420                 425                 430

Trp Leu Ile Cys Trp Glu Val Leu Cys Ser Val His Leu Ile Gly Asn
        435                 440                 445

Cys Tyr Pro Ser Val Leu Tyr Arg Val Leu His Gly Pro Ile Ser Val
    450                 455                 460

Ser His Ser Lys Glu Ser Val Trp Phe Pro Tyr Trp Ile Arg Arg Trp
465                 470                 475                 480

Met Phe Tyr Ala Val Leu Gly Phe Phe Ile Pro Ala Leu Asn Gly Leu
                485                 490                 495

Leu Pro Phe Ala Ser Leu Ser Asp Trp Asn Asn His Phe Thr Lys Glu
            500                 505                 510

Leu Lys Ser Ile Phe Ile Asp Glu Arg Ile Glu Ala
        515                 520
```

<210> SEQ ID NO 105
<211> LENGTH: 1179
<212> TYPE: DNA
<213> ORGANISM: Sorghum bicolor

<400> SEQUENCE: 105

```
atgagaaact ttgagaaatc attcagcagc acattaacaa cgcttcatct tgttaatgag     60

atgcctgtct atggacaagg tccagttcct caatgttctt ctaagcatga agactctgat    120

gctgcaagca agttgagcac tgatggtcca caaaatccaa cgcaagaaat caagcaggac    180

ctttcaaatt cagtggaaag tcagcttgtt ctgtatgctg gtggcaatca gcagctgact    240

cgtcgtactc atagcatatc ttctcctgaa gctaatcggc ggatccttaa tgcatttgaa    300

agatctttga aagaacaaac tcggtcaaat gagctcaagg aatttgagat aagccttagc    360

atgagaaagt tgcaacttaa acagtctcaa ctagaactta actcctactc gcacatgtta    420

gacaagatta agttatcctt gggatttcag aaagcttcct tccaaacgga gaaattcaag    480

actcagatgc aggacacgag gcatgcacaa ataatgagga cactcataga tttccttgtt    540

agtgcagtta ttattatgtc agtatgtttt gggtacggaa cttatattta ttcataccaa    600

aggataactg atattacagc agcatgtgca gccacttcaa ggggatctaa atcatggtgg    660

gtgccaaatt cagtgtcaaa cttcaattcc gggttgctct tcatgagatg tcatgtagta    720

gctgcaacac ggatgttctt tggcatagta atgattctgg caattgtttg gttagcattc    780

cagcgttctg cagtgtctgg atcaagtatg ccagtaactt tcaacatcat actgttggga    840

attatttgtg gctttgctgg aaggttctgt accaacacac ttggtggcga tgggaacatg    900

tggcttatat gctgggaggt tctttgttcc atccatttac ttggaaattg ttatccatcg    960

gtcttgtacc gtgttcttca tggtcctata tctgtatctg acagcaagga gtctgtctgg   1020

ttcccgtatt ggattcgccg ctggatcttt tatgctgcgc tggggttttt tatcccagcc   1080

ttgaatggct tactgccatt tgcttctctt tctgactgga ataaccattt cactaaggag   1140

ctaaaatcca tctttattgg tgagaaaatt gaagcttga                           1179
```

<210> SEQ ID NO 106
<211> LENGTH: 392
<212> TYPE: PRT
<213> ORGANISM: Sorghum bicolor

<400> SEQUENCE: 106

```
Met Arg Asn Phe Glu Lys Ser Phe Ser Ser Thr Leu Thr Thr Leu His
```

```
1               5                   10                  15

Leu Val Asn Glu Met Pro Val Tyr Gly Gln Gly Pro Val Pro Gln Cys
            20                  25                  30

Ser Ser Lys His Glu Asp Ser Asp Ala Ala Ser Lys Leu Ser Thr Asp
        35                  40                  45

Gly Pro Gln Asn Pro Thr Gln Glu Ile Lys Gln Asp Leu Ser Asn Ser
    50                  55                  60

Val Glu Ser Gln Leu Val Leu Tyr Ala Gly Gly Asn Gln Gln Leu Thr
65                  70                  75                  80

Arg Arg Thr His Ser Ile Ser Ser Pro Glu Ala Asn Arg Arg Ile Leu
                85                  90                  95

Asn Ala Phe Glu Arg Ser Leu Lys Glu Gln Thr Arg Ser Asn Glu Leu
            100                 105                 110

Lys Glu Phe Glu Ile Ser Leu Ser Met Arg Lys Leu Gln Leu Lys Gln
        115                 120                 125

Ser Gln Leu Glu Leu Asn Ser Tyr Ser His Met Leu Asp Lys Ile Lys
    130                 135                 140

Leu Ser Leu Gly Phe Gln Lys Ala Ser Phe Gln Thr Glu Lys Phe Lys
145                 150                 155                 160

Thr Gln Met Gln Asp Thr Arg His Ala Gln Ile Met Arg Thr Leu Ile
                165                 170                 175

Asp Phe Leu Val Ser Ala Val Ile Ile Met Ser Val Cys Phe Gly Tyr
            180                 185                 190

Gly Thr Tyr Ile Tyr Ser Tyr Gln Arg Ile Thr Asp Ile Thr Ala Ala
        195                 200                 205

Cys Ala Ala Thr Ser Arg Gly Ser Lys Ser Trp Trp Val Pro Asn Ser
    210                 215                 220

Val Ser Asn Phe Asn Ser Gly Leu Leu Phe Met Arg Cys His Val Val
225                 230                 235                 240

Ala Ala Thr Arg Met Phe Phe Gly Ile Val Met Ile Leu Ala Ile Val
                245                 250                 255

Trp Leu Ala Phe Gln Arg Ser Ala Val Ser Gly Ser Ser Met Pro Val
            260                 265                 270

Thr Phe Asn Ile Ile Leu Leu Gly Ile Ile Cys Gly Phe Ala Gly Arg
        275                 280                 285

Phe Cys Thr Asn Thr Leu Gly Gly Asp Gly Asn Met Trp Leu Ile Cys
    290                 295                 300

Trp Glu Val Leu Cys Ser Ile His Leu Leu Gly Asn Cys Tyr Pro Ser
305                 310                 315                 320

Val Leu Tyr Arg Val Leu His Gly Pro Ile Ser Val Ser Asp Ser Lys
                325                 330                 335

Glu Ser Val Trp Phe Pro Tyr Trp Ile Arg Arg Trp Ile Phe Tyr Ala
            340                 345                 350

Ala Leu Gly Phe Phe Ile Pro Ala Leu Asn Gly Leu Leu Pro Phe Ala
        355                 360                 365

Ser Leu Ser Asp Trp Asn Asn His Phe Thr Lys Glu Leu Lys Ser Ile
    370                 375                 380

Phe Ile Gly Glu Lys Ile Glu Ala
385                 390
```

<210> SEQ ID NO 107
<211> LENGTH: 1695
<212> TYPE: DNA
<213> ORGANISM: Arabidopsis thaliana

<400> SEQUENCE: 107

```
atggaagccc tcctcctccc tccttcgccg gaaccccaaa atcaaatcac caatccggcg     60
aattcaaagc caaatcatca atctggtgac gtacataaag atgagacgat gatgatgaag    120
aagaagaagg atacgaatcc atcgaatttg gaaaagagaa aactcaaggg aaagaagaaa    180
gagattatgg acaacgacga agcttcttcg tcctattgtt ctacatcttc tacctctaat    240
tcaaattcta ctaaaagggt tacgagagtg gttcatagat tacgaaaccc tatgcggtta    300
ggtatggctc gacgaagcgt tggtgaacga caagctgaaa aattggcgaa gcctctgggc    360
ttttcacttg ccgcttttgc taatatggtt attgcgagaa agaatgccgc aggtcagaat    420
gtttatgttg atgatcttgt tgagatcttt gctactcttg tcgaagaatc attagccaat    480
gtttatggta ataagcttgg ttcctttgcg accaactttg agcaaacatt cagcagtact    540
ctaaagatcc ttaaattgac caatgaatgt gcaaatccac atcagtcaaa caataatgat    600
ggtgggagtt gtaatttaga tcgctctacc atagacggat gctcagacac cgagctattt    660
gagagggaga cttcatctgc tacgtctgct tatgaagtga tgcaaggcag tgcaacagca    720
acctctttga tgaatgagct tgccctttc gaagagactc tacaactctc ttgtgtccct    780
cctagaagtt cagcaatggc tttgaccaca gacgaaaggt ttttaaaaga gcaaacacga    840
gcaaacgacc taaagaccgt ggagattggt cttcaaataa gagagttaag gtgcaaagag    900
acggcgctag gattaaaatt tgaatcaaac aacctgggga aagcggcgct agagttggat    960
gtttcgaaag ctgcattcag agcggagaaa ttcaaaaccg aattagaaga tacaagaaaa   1020
gaagagatgg tcacaagaat catggattgg ctcctcgtaa gtgtcttcag catgttggct   1080
tctatggtac ttggcgttta caatttttca ataaagagaa tcgaggatgc tacctcagta   1140
tgcgaccaat ccgaggagaa aagttcgtcg tggtgggttc ctaaacaagt ttcatcgatt   1200
aactcaggct tcaacacctt catctgccgg gttcgagttt gggtgcagat atttttcggt   1260
gtgttaatga tcattgtctt cacttacttt ctaaacaaac gatcatcagg tacgaagcag   1320
acaatgccga taagtttcat cgttcttttc ctcggtatat tttgcggtgt atcgggtaaa   1380
ttgtgtgtgg acacattggg cggtgatggc aaactctggc taatagtttg ggaagtgttt   1440
tgccttttgc aattcgttgc aaatgtcttc acattggctt tgtatggtct aatgttcggt   1500
cctataaacg tgactcaaga gaccagatcg aaccgttgta acagtatgtt tccatattgg   1560
gcaaggcgca gtgtcgtgta tgtggtgatt ctgtttgttc ttccagtcat aaacggtctt   1620
ttgccatttg caacatttgg tgaatggaga gacttcgcta tgtatcacct tcatggtggg   1680
tctgactatg cttga                                                    1695
```

<210> SEQ ID NO 108
<211> LENGTH: 564
<212> TYPE: PRT
<213> ORGANISM: Arabidopsis thaliana

<400> SEQUENCE: 108

```
Met Glu Ala Leu Leu Leu Pro Pro Ser Pro Glu Pro Gln Asn Gln Ile
1               5                   10                  15

Thr Asn Pro Ala Asn Ser Lys Pro Asn His Gln Ser Gly Asp Val His
            20                  25                  30

Lys Asp Glu Thr Met Met Met Lys Lys Lys Lys Asp Thr Asn Pro Ser
        35                  40                  45

Asn Leu Glu Lys Arg Lys Leu Lys Gly Lys Lys Lys Glu Ile Met Asp
```

```
    50                  55                  60

Asn Asp Glu Ala Ser Ser Ser Tyr Cys Ser Thr Ser Ser Thr Ser Asn
65                  70                  75                  80

Ser Asn Ser Thr Lys Arg Val Thr Arg Val Val His Arg Leu Arg Asn
                85                  90                  95

Pro Met Arg Leu Gly Met Ala Arg Arg Ser Val Gly Glu Arg Gln Ala
            100                 105                 110

Glu Lys Leu Ala Lys Pro Leu Gly Phe Ser Leu Ala Ala Phe Ala Asn
        115                 120                 125

Met Val Ile Ala Arg Lys Asn Ala Ala Gly Gln Asn Val Tyr Val Asp
    130                 135                 140

Asp Leu Val Glu Ile Phe Ala Thr Leu Val Glu Glu Ser Leu Ala Asn
145                 150                 155                 160

Val Tyr Gly Asn Lys Leu Gly Ser Phe Ala Thr Asn Phe Glu Gln Thr
                165                 170                 175

Phe Ser Ser Thr Leu Lys Ile Leu Lys Leu Thr Asn Glu Cys Ala Asn
            180                 185                 190

Pro His Gln Ser Asn Asn Asn Asp Gly Gly Ser Cys Asn Leu Asp Arg
        195                 200                 205

Ser Thr Ile Asp Gly Cys Ser Asp Thr Glu Leu Phe Glu Arg Glu Thr
    210                 215                 220

Ser Ser Ala Thr Ser Ala Tyr Glu Val Met Gln Gly Ser Ala Thr Ala
225                 230                 235                 240

Thr Ser Leu Met Asn Glu Leu Ala Leu Phe Glu Glu Thr Leu Gln Leu
                245                 250                 255

Ser Cys Val Pro Pro Arg Ser Ser Ala Met Ala Leu Thr Thr Asp Glu
            260                 265                 270

Arg Phe Leu Lys Glu Gln Thr Arg Ala Asn Asp Leu Lys Thr Val Glu
        275                 280                 285

Ile Gly Leu Gln Ile Arg Glu Leu Arg Cys Lys Glu Thr Ala Leu Gly
    290                 295                 300

Leu Lys Phe Glu Ser Asn Asn Leu Gly Lys Ala Ala Leu Glu Leu Asp
305                 310                 315                 320

Val Ser Lys Ala Ala Phe Arg Ala Glu Lys Phe Lys Thr Glu Leu Glu
                325                 330                 335

Asp Thr Arg Lys Glu Glu Met Val Thr Arg Ile Met Asp Trp Leu Leu
            340                 345                 350

Val Ser Val Phe Ser Met Leu Ala Ser Met Val Leu Gly Val Tyr Asn
        355                 360                 365

Phe Ser Ile Lys Arg Ile Glu Asp Ala Thr Ser Val Cys Asp Gln Ser
    370                 375                 380

Glu Glu Lys Ser Ser Ser Trp Trp Val Pro Lys Gln Val Ser Ser Ile
385                 390                 395                 400

Asn Ser Gly Phe Asn Thr Phe Ile Cys Arg Val Arg Val Trp Val Gln
                405                 410                 415

Ile Phe Phe Gly Val Leu Met Ile Ile Val Phe Thr Tyr Phe Leu Asn
            420                 425                 430

Lys Arg Ser Ser Gly Thr Lys Gln Thr Met Pro Ile Ser Phe Ile Val
        435                 440                 445

Leu Phe Leu Gly Ile Phe Cys Gly Val Ser Gly Lys Leu Cys Val Asp
    450                 455                 460

Thr Leu Gly Gly Asp Gly Lys Leu Trp Leu Ile Val Trp Glu Val Phe
465                 470                 475                 480
```

```
Cys Leu Leu Gln Phe Val Ala Asn Val Phe Thr Leu Ala Leu Tyr Gly
                485                 490                 495

Leu Met Phe Gly Pro Ile Asn Val Thr Gln Glu Thr Arg Ser Asn Arg
            500                 505                 510

Cys Asn Ser Met Phe Pro Tyr Trp Ala Arg Arg Ser Val Val Tyr Val
        515                 520                 525

Val Ile Leu Phe Val Leu Pro Val Ile Asn Gly Leu Leu Pro Phe Ala
    530                 535                 540

Thr Phe Gly Glu Trp Arg Asp Phe Ala Met Tyr His Leu His Gly Gly
545                 550                 555                 560

Ser Asp Tyr Ala


<210> SEQ ID NO 109
<211> LENGTH: 1668
<212> TYPE: DNA
<213> ORGANISM: Glycine max

<400> SEQUENCE: 109

atggctgaga ttcagaattg ttcctcggaa ccagaaccaa ccgcaatcaa cgaatgggag      60

ggtcaagctt cgatgaagag cacaacgcaa agttcagaag cctccgatac gacgtcgtca     120

cgaaaagaga ataaaggtaa aggtaaggct gcggcgttca aacgacggaa ccctagagtt     180

cttgttcgcc gccatagggc taataatgtg gacactattg gccttcctct tggcatgtca     240

ttcgccgctg ttatggctca ggtgatgtat agaagagatg tagcagccga gagtatgtct     300

cccagtcatc tttcgatgat gtgttcatcg gctatcaaag aatctcttgc cagtgttttt     360

ggagacaagc tagatggttt gacgaggaac tttgaacaat ctttttgtag caccttgagt     420

actcttcagt taatttatga atcatccaag agcaatgaag gaaataaatt aaataataca     480

aagatggaaa ttatgagttc taaattgact ctcaataaag aggaatgctc aggtgatatt     540

gttacagagg tcggtcattc aagacatgct gaaatccaag atcaatcaat tagtcatgat     600

tctcctgaag agagcaggga taactttcat atgggttcag ttagtcgcga tctcactttg     660

tatgggcaat caaaccaaat ggtttccttt tctcaaatat cttttggatc tgtaaataat     720

cctatggtta gtatttttga gaagtccatc atggagcagt gtcgttctaa tgacctcaag     780

acacttgaac ttggccttaa aatgaaggaa ttgaaattga aagaggatga attggctctc     840

aaccttgatt cgaataattt aaacagatca aaattagtca tgggagaatc aaagcaatct     900

ttcaaagagg aaaagttcaa gacccagtta gaagatacga ggcatggtga actcaaaaag     960

aagtgcattg actgtcttat tactggtttg cttatcatgt catcctcact tttgtatggt    1020

gcctatgttt attcctacga gcggattact aaagctactg aatcatgtac accatcaacc    1080

caggcaatgg ttgtgtctgc atactactcc agcattgcct ttgctcaatt ggcagttgaa    1140

tcttcctcct ggtggactcc caagtcaatg gtcttattca attcaaagtt gcatattttg    1200

tggtgtcaag ttcaagttat gagccgaatg gcatttggca tcttgatgat tttgctgtt     1260

gcatatttgc tcttgcagcg gtcgaccaca acatcacaga ctatgccagt cactttcatc    1320

cttttaatgt tgggaatttt ttgtggctat tgtggcaagc tatgtgtaga gacattgggt    1380

gggagtggta ttgtgtggct cttatactgg gagattatgt gcttgctgca tttcttatct    1440

ctttgctgga catccgcttt gttccggatc cttcatggac cagtcactcc atcacaaaca    1500

atggaggaga atacaattct tcggtattgg attcgcagag ttctgttcta tgctgctatg    1560

cttgtgtttc taccgttgtt ttgtggtctc atgccatttg ctagcctagg tcaatggaaa    1620
```

gaacatttta cattgaaggg gtcagatttt aatggatccg aatggtaa 1668

<210> SEQ ID NO 110
<211> LENGTH: 555
<212> TYPE: PRT
<213> ORGANISM: Glycine max

<400> SEQUENCE: 110

```
Met Ala Glu Ile Gln Asn Cys Ser Ser Glu Pro Glu Pro Thr Ala Ile
1               5                   10                  15

Asn Glu Trp Glu Gly Gln Ala Ser Met Lys Ser Thr Thr Gln Ser Ser
            20                  25                  30

Glu Ala Ser Asp Thr Thr Ser Ser Arg Lys Glu Asn Lys Gly Lys Gly
        35                  40                  45

Lys Ala Ala Ala Phe Lys Arg Arg Asn Pro Arg Val Leu Val Arg Arg
    50                  55                  60

His Arg Ala Asn Asn Val Asp Thr Ile Gly Leu Pro Leu Gly Met Ser
65                  70                  75                  80

Phe Ala Ala Val Met Ala Gln Val Met Tyr Arg Arg Asp Val Ala Ala
                85                  90                  95

Glu Ser Met Ser Pro Ser His Leu Ser Met Met Cys Ser Ser Ala Ile
            100                 105                 110

Lys Glu Ser Leu Ala Ser Val Phe Gly Asp Lys Leu Asp Gly Leu Thr
        115                 120                 125

Arg Asn Phe Glu Gln Ser Phe Cys Ser Thr Leu Ser Thr Leu Gln Leu
    130                 135                 140

Ile Tyr Glu Ser Ser Lys Ser Asn Glu Gly Asn Lys Leu Asn Asn Thr
145                 150                 155                 160

Lys Met Glu Ile Met Ser Ser Lys Leu Thr Leu Asn Lys Glu Glu Cys
                165                 170                 175

Ser Gly Asp Ile Val Thr Glu Val Gly His Ser Arg His Ala Glu Ile
            180                 185                 190

Gln Asp Gln Ser Ile Ser His Asp Ser Pro Glu Glu Ser Arg Asp Asn
        195                 200                 205

Phe His Met Gly Ser Val Ser Arg Asp Leu Thr Leu Tyr Gly Gln Ser
    210                 215                 220

Asn Gln Met Val Ser Phe Ser Gln Ile Ser Phe Gly Ser Val Asn Asn
225                 230                 235                 240

Pro Met Val Ser Ile Phe Glu Lys Ser Ile Met Glu Gln Cys Arg Ser
                245                 250                 255

Asn Asp Leu Lys Thr Leu Glu Leu Gly Leu Lys Met Lys Glu Leu Lys
            260                 265                 270

Leu Lys Glu Asp Glu Leu Ala Leu Asn Leu Asp Ser Asn Asn Leu Asn
        275                 280                 285

Arg Ser Lys Leu Val Met Gly Glu Ser Lys Gln Ser Phe Lys Glu Glu
    290                 295                 300

Lys Phe Lys Thr Gln Leu Glu Asp Thr Arg His Gly Glu Leu Lys Lys
305                 310                 315                 320

Lys Cys Ile Asp Cys Leu Ile Thr Gly Leu Leu Ile Met Ser Ser Ser
                325                 330                 335

Leu Leu Tyr Gly Ala Tyr Val Tyr Ser Tyr Glu Arg Ile Thr Lys Ala
            340                 345                 350

Thr Glu Ser Cys Thr Pro Ser Thr Gln Ala Met Val Val Ser Ala Tyr
        355                 360                 365
```

```
Tyr Ser Ser Ile Ala Phe Ala Gln Leu Ala Val Glu Ser Ser Ser Trp
    370                 375                 380

Trp Thr Pro Lys Ser Met Val Leu Phe Asn Ser Lys Leu His Ile Leu
385                 390                 395                 400

Trp Cys Gln Val Gln Val Met Ser Arg Met Ala Phe Gly Ile Leu Met
                405                 410                 415

Ile Phe Ala Val Ala Tyr Leu Leu Leu Gln Arg Ser Thr Thr Thr Ser
            420                 425                 430

Gln Thr Met Pro Val Thr Phe Ile Leu Leu Met Leu Gly Ile Phe Cys
        435                 440                 445

Gly Tyr Cys Gly Lys Leu Cys Val Glu Thr Leu Gly Gly Ser Gly Ile
    450                 455                 460

Val Trp Leu Leu Tyr Trp Glu Ile Met Cys Leu Leu His Phe Leu Ser
465                 470                 475                 480

Leu Cys Trp Thr Ser Ala Leu Phe Arg Ile Leu His Gly Pro Val Thr
                485                 490                 495

Pro Ser Gln Thr Met Glu Glu Asn Thr Ile Leu Arg Tyr Trp Ile Arg
            500                 505                 510

Arg Val Leu Phe Tyr Ala Ala Met Leu Val Phe Leu Pro Leu Phe Cys
        515                 520                 525

Gly Leu Met Pro Phe Ala Ser Leu Gly Gln Trp Lys Glu His Phe Thr
    530                 535                 540

Leu Lys Gly Ser Asp Phe Asn Gly Ser Glu Trp
545                 550                 555
```

<210> SEQ ID NO 111
<211> LENGTH: 945
<212> TYPE: DNA
<213> ORGANISM: Oryza sativa

<400> SEQUENCE: 111

```
atgctacaca agtctatccc taacggcggc cggatcgcac gccgtatcat ccccacccac      60

tgcgacggcc ttgtcgccgt cgccacctgc ggcggggcca cgttcgtgtg caacccggcc     120

acccaggagc tcgtcgtgtt gccgcccggc accagcggcc gcagccgccg cggcccgtcc     180

ccagtgtcta ccgaatcgac ggcggcgatc ggcttcgatc cgtggcggaa caggtacgtc     240

gtcgccagat gcttctacta ccgcaagtcc ggcaaccact atccgccggt ctacaacgtc     300

gggcacgaga tcttcacgct cggcggcggc gccggcgacg gatggctggc ggactgcagg     360

acccgccgcg cgccatcagc cccgacggga gacccgccgc ctgcacgcgc ggcggcgggg     420

cctccttcta ctggttcatc gacgagcatg agccgtgcgc gctgctgcgg ttcagcctgc     480

gggacgaggc gttcgacgtg gtccccgtgc cccccgggct gcacgggctt cacgtacgac     540

gaccgcctgg cggacctcgc cggcgagctg tgctacgtgc atcgtgtccg cacgggggtt     600

gccacccacg aagtttggat ggcggcggcg gcggtcgacg acgacgagcc ggagtggtgg     660

ctgcgatacc gagtggacct gtgggggtac gcgtggggct tggtcgccgg cgaacgctgg     720

ttccacagct tcggcgccac ggccggcgat gacggcgtgg acgaggaggc gacgttggtg     780

accatgttgt acaaggagct gtgctggcac agggagcgga gcaaaccggt ggtgaaagac     840

gtgaacgtgc gagggagccg gtacagctgt gagccgactc cgactataca ccatgtcatc     900

cgttacgtgg agagcctcgt ctccattaca gcacctaact actga                     945
```

<210> SEQ ID NO 112

<211> LENGTH: 314
<212> TYPE: PRT
<213> ORGANISM: Oryza sativa

<400> SEQUENCE: 112

Met Leu His Lys Ser Ile Pro Asn Gly Gly Arg Ile Ala Arg Arg Ile
1               5                   10                  15

Ile Pro Thr His Cys Asp Gly Leu Val Ala Val Ala Thr Cys Gly Gly
            20                  25                  30

Ala Thr Phe Val Cys Asn Pro Ala Thr Gln Glu Leu Val Val Leu Pro
        35                  40                  45

Pro Gly Thr Ser Gly Arg Ser Arg Arg Gly Pro Ser Pro Val Ser Thr
    50                  55                  60

Glu Ser Thr Ala Ala Ile Gly Phe Asp Pro Trp Arg Asn Arg Tyr Val
65                  70                  75                  80

Val Ala Arg Cys Phe Tyr Tyr Arg Lys Ser Gly Asn His Tyr Pro Pro
                85                  90                  95

Val Tyr Asn Val Gly His Glu Ile Phe Thr Leu Gly Gly Gly Ala Gly
            100                 105                 110

Asp Gly Trp Leu Ala Asp Cys Arg Thr Arg Arg Ala Pro Ser Ala Pro
        115                 120                 125

Thr Gly Asp Pro Pro Pro Ala Arg Ala Ala Ala Gly Pro Pro Ser Thr
    130                 135                 140

Gly Ser Ser Thr Ser Met Ser Arg Ala Arg Cys Cys Gly Ser Ala Cys
145                 150                 155                 160

Gly Thr Arg Arg Ser Thr Trp Ser Pro Cys Pro Pro Gly Cys Thr Gly
                165                 170                 175

Phe Thr Tyr Asp Asp Arg Leu Ala Asp Leu Ala Gly Glu Leu Cys Tyr
            180                 185                 190

Val His Arg Val Arg Thr Gly Val Ala Thr His Glu Val Trp Met Ala
        195                 200                 205

Ala Ala Ala Val Asp Asp Asp Glu Pro Glu Trp Trp Leu Arg Tyr Arg
    210                 215                 220

Val Asp Leu Trp Gly Tyr Ala Trp Gly Leu Val Ala Gly Glu Arg Trp
225                 230                 235                 240

Phe His Ser Phe Gly Ala Thr Ala Gly Asp Asp Gly Val Asp Glu Glu
                245                 250                 255

Ala Thr Leu Val Thr Met Leu Tyr Lys Glu Leu Cys Trp His Arg Glu
            260                 265                 270

Arg Ser Lys Pro Val Val Lys Asp Val Asn Val Arg Gly Ser Arg Tyr
        275                 280                 285

Ser Cys Glu Pro Thr Pro Thr Ile His His Val Ile Arg Tyr Val Glu
    290                 295                 300

Ser Leu Val Ser Ile Thr Ala Pro Asn Tyr
305                 310